US006979551B2

(12) United States Patent
Issakani et al.

(10) Patent No.: US 6,979,551 B2
(45) Date of Patent: Dec. 27, 2005

(54) ASSAYS FOR IDENTIFYING UBIQUITIN AGENTS AND FOR IDENTIFYING AGENTS THAT MODIFY THE ACTIVITY OF UBIQUITIN AGENTS

(75) Inventors: Sarkiz D. Issakani, San Jose, CA (US); Jianing Huang, Foster City, CA (US); Julie Sheung, San Francisco, CA (US); Todd R. Pray, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 446 days.

(21) Appl. No.: 10/152,156

(22) Filed: May 20, 2002

(65) Prior Publication Data

US 2003/0108947 A1 Jun. 12, 2003

Related U.S. Application Data

(63) Continuation-in-part of application No. 10/108,767, filed on Mar. 26, 2002, and a continuation-in-part of application No. 10/109,460, filed on Mar. 26, 2002, now abandoned, and a continuation-in-part of application No. 10/091,139, filed on Mar. 4, 2002, now abandoned, and a continuation-in-part of application No. 10/091,174, filed on Mar. 4, 2002, now abandoned, and a continuation-in-part of application No. 09/826,312, filed on Apr. 3, 2001, now Pat. No. 6,737,244, and a continuation-in-part of application No. 09/542,497, filed on Apr. 3, 2001, now Pat. No. 6,740,495.

(60) Provisional application No. 60/291,836, filed on May 18, 2001.

(51) Int. Cl.[7] .............................................. G01N 33/53
(52) U.S. Cl. ..................... 435/7.92; 435/7.1; 435/7.4; 435/7.6; 435/7.9; 435/7.91; 435/7.93; 435/7.94; 435/7.95; 435/21; 435/14; 435/28; 436/546; 436/544; 436/164; 436/172; 436/805
(58) Field of Search ................................ 435/7.92, 7.1, 435/7.4, 7.6, 7.9, 7.71, 7.93, 7.95, 21, 14, 28; 436/546, 544, 164, 172, 805

(56) References Cited

U.S. PATENT DOCUMENTS 5,976,849 A    11/1999  Hustad et al.

*Primary Examiner*—Christopher L. Chin
*Assistant Examiner*—Pensee T. Do
(74) *Attorney, Agent, or Firm*—Townsend and Townsend and Crew LLP

(57) ABSTRACT

Provided are methods and compositions for assaying for ubiquitin agents that are enzymatic components of ubiquitin-mediated proteolysis and, more particularly, methods and compositions for assaying for agents that modulate the activity of such ubiquitin agents.

33 Claims, 55 Drawing Sheets

FIGURE 8A

```
ATGTCCAGCTCGCCGCTGTCCAAGAAACGTCGCGTGTCCGGGCCTGATCCAAAGCCGGGTTCTAACTGCTCCCCTGCCCA
GTCCGTGTTGCCCCAAGTGCCCTCGGCGCCAACCAACGGAATGGCGAAGAACGGCAGTGAAGCAGACATCGATGAGGGCC
TTTACTCCCGGCAGCTGTATGTGTTGGGCCATGAGGCGATGAAGCGGCTCCAGACATCCAGCGTTCTGGTGTCAGGCCTG
CGGGGCCTGGGGGTAGAGATCGCGAAGAACATCATCCTTGGCGGGGTCAAGGCCGTGACCCTCCATGACCAGGGCACGGC
CCAGTGGGCTGACCTCTCCTCCCAGTTCTACCTGCGAGAGGAGGACATAGGGAAAAACCGCGCTGAGGTGTCACAGCCCC
GCCTTGCTGAACTCAATAGCTACGTGCCTGTCACCGCCTACACTGGGCCGCTGGTTGAGGACTTCCTCAGTGGCTTCCAG
GTGGTGGTCCTCACTAACAGCCCCTGGAGGACCAGCTGCGCGTGGGCGAGTTCTGTCATAGCCGTGGCATCAAGCTGGT
AGTGGCAGACACGAGAGGCTTGTTTGGGCAACTCTTCTGCGACTTTGGAGAGGAAATGATCCTCACAGATTCCAACGGGG
AGCAGCCCCTCAGCACCATGGTTTCTATGGTCACCAAGGACAACCCTGGTGTGGTTACCTGCCTGGATGAGGCCCGACAT
GGGTTTGAGAGTGGCGATTTTGTTTCCTTCTCCGAAGTACAGGGCATGACTGAGCTCAATGGAAACCAGCCCATAGAGAT
CAAAGTCCTGGGTCCTTACACCTTTAGCATCTGTGACACCTCCAACTTCTCCGATTACATCCGTGGAGGCATTGTCAGCC
AGGTCAAAGTACCTAAGAAGATAAGCTTTAAATCCTTGTCAGCCTCGCTGGCAGAGCCTGACTTTGTGATGACGGACTTC
GCCAAGTTTTCTCGCCCCGCTCAGCTTCACATTGGCTTCCAGGCCTTGCACAAGTTCTGTGCACAGCACAGCCGGCCACC
TAGACCCCGAACGAGGAGGATGCAGCAGAGCTGGTGACCCTAGCACGCGCTGTGAACTCTAAAGCCTCGTCGGCAGTGC
AGCAAGATAGCCTGGATGAGGACCTCATCCGGAACCTGGCCTTTGTGGCAGCCGGGGACCTGGCGCCCATCAATGCCTTC
ATTGGGGGCCTGGCTGCCCAGGAAGTCATGAAGGCCTGCTCTGGGAAGTTTATGCCCATCATGCAGTGGCTGTACTTTGA
TGCCCTTGAGTGTCTCCCGGAGGACAAAGAATCCCTCACAGAGGACAAGTGCCTCCCGCGCCAGAACCGTTATGATGGGC
AGGTGGCTGTGTTTGGCTCAGACCTGCAAGAGAAGCTGGGCAGGCAGAAGTACTTCCTGGTGGGTGCAGGGGCTATTGGC
TGTGAGCTGCTCAAGAACTTTGCCATGATTGGGCTGGGCTGTGGTGAGAACGGAGAAATAATTGTCACAGACATGGACAC
CATTGAGAAATCTAATCTGAACCGACAGTTTCTATTCCGGCCCTGGGATGTCACGAAGTTAAAATCTGACACAGCTGCTG
CAGCTGTGCACCAGATGAATCCACATATCCGGGTGACAAGCCACCAGAACCGTGTGGGTCCTGACACTGAACGTATCTAC
GACGACGATTTCTTCCAAACTCTGGATGGCGTGGCCAACGCCTTAGCAACGTGGATGCCCGCATGTACATGGACCGCCG
CTGCGTGTACTACCGGAAGCCGCTGCTCGAATCAGGCACCCTGGGCACCAAGGGCAACGTCCAGGTGGTGATCCCCTTCC
TGACAGAGTCCTACAGCTCCAGCCAAGACCCACCTGAGAAGTCCATCCCCATCTGTACCCTGAAGAACTTCCCCAACGCC
ATCGAACACACTCTTCAGTGGGCTCGGGATGAATTTGAAGGCCTCTTCAAGCAGCCAGCGGAAAATGTCAACCAGTACCT
CACAGACCCTAAGTTTGTGGAGCGGACATTGCGGCTGGCGGGTACCCAGCCACTGGAGGTGCTGGAGGCTGTGCAGCGCA
GCCTGGTGCTGCAGCTACCGCAGAGCTGGGCAGACTGTGTGACCTGGGCCTGCCACCACTGGCACACCCAGTATTCTAAC
AATATCCGGCAGCTGTTGCACAACTTCCCTCCCGACCAGCTCACAAGCTCGGGAGCTCCTTCTGGTCTGGGCCCAAACG
TTGTCCTCACCCACTCACCTTTGATGTTAGCAACCCTCTGCATCTGGACTATGTGATGGCTGCTGCCAACCTGTTTGCCC
AGACCTACGGGCTGGCAGGCTCTCAGGACCGAGCTGCTGTGGCCACACTCCTGCAGTCTGTACAGGTCCCCGAGTTTACC
CCCAAGTCTGGCGTCAAAATCCACGTTTCTGACCAGGAGCTGCAGAGCGCCAATGCTTCTGTTGACGACAGCCGTTTAGA
GGAGCTCAAGGCTACGCTGCCTAGCCCCGACAAGCTCCCTGGATTCAAGATGTACCCCATTGACTTTGAGAAGGATGATG
ATAGTAACTTTCACATGGACTTCATTGTGGCCGCATCCAACCTCCGGGCCGAAAACTATGACATTCCCCCTGCAGACCGG
CACAAGAGCAAGCTGATTGCAGGGAAGATCATCCCAGCCATTGCCACGACCACAGCAGCTGTCGTTGGCCTTGTGTGTCT
GGAGCTGTACAAGGTAGTGCAGGGACACCGACACCTCGACTCCTACAAGAATGGTTTCCTCAACCTGGCCCTGCCGTTTT
TCGGTTTCTCTGAACCTCTGGCTGCACCACGTCACCAGTACTATAACCAAGAGTGGACATTGTGGGATCGCTTTGAGGTT
CAGGGACTGCAGCCCAACGGTGAGGAGATGACCCCTCAAACAATTCCTCGACTACTTTAAGACAGAGCACAAATTGGAGAT
TACCATGCTGTCCCAGGGTGTGTCCATGCTCTATTCCTTCTTTATGCCAGCTGCGAAGCTCAAGGAACGGTTGGACCAGC
CGATGACAGAGATTGTAAGCCGTGTGTCGAAGCGAAAGCTGGGCCGCCACGTGCGGGCGCTGGTGCTTGAGCTGTGCTGC
AACGACGAGAGCGGCGAGGACGTCGAAGTCCCCTACGTCCGATATACCATCCGTTAA
```

FIGURE 8B

MSSSPLSKKRRVSGPDPKPGSNCSPAQSVLPQVPSAPTNGMAKNGSEADIDEGLYSRQLYVLGHEAMKRLQTSSVLVSGL
RGLGVEIAKNIILGGVKAVTLHDQGTAQWADLSSQFYLREEDIGKNRAEVSQPRLAELNSYVPVTAYTGPLVEDFLSGFQ
VVVLTNSPLEDQLRVGEFCHSRGIKLVVADTRGLFGQLFCDFGEEMILTDSNGEQPLSTMVSMVTKDNPGVVTCLDEARH
GFESGDFVSFSEVQGMTELNGNQPIEIKVLGPYTFSICDTSNFSDYIRGGIVSQVKVPKKISFKSLSASLAEPDFVMTDF
AKFSRPAQLHIGFQALHKFCAQHSRPPRPRNEEDAAELVTLARAVNSKASSAVQQDSLDEDLIRNLAFVAAGDLAPINAF
IGGLAAQEVMKACSGKFMPIMQWLYFDALECLPEDKESLTEDKCLPRQNRYDGQVAVFGSDLQEKLGRQKYFLVGAGAIG
CELLKNFAMIGLGCGENGEIIVTDMDTIEKSNLNRQFLFRPWDVTKLKSDTAAAAVHQMNPHIRVTSHQNRVGPDTERIY
DDDFFQTLDGVANALDNVDARMYMDRRCVYYRKPLLESGTLGTKGNVQVVIPFLTESYSSSQDPPEKSIPICTLKNFPNA
IEHTLQWARDEFEGLFKQPAENVNQYLTDPKFVERTLRLAGTQPLEVLEAVQRSLVLQLPQSWADCVTWACHHWHTQYSN
NIRQLLHNFPPDQLTSSGAPFWSGPKRCPHPLTFDVSNPLHLDYVMAAANLFAQTYGLAGSQDRAAVATLLQSVQVPEFT
PKSGVKIHVSDQELQSANASVDDSRLEELKATLPSPDKLPGFKMYPIDFEKDDDSNFHMDFIVAASNLRAENYDIPPADR
HKSKLIAGKIIPAIATTTAAVVGLVCLELYKVVQGHRHLDSYKNGFLNLALPFFGFSEPLAPPPHQYYNQEWTLWDRFEV
QGLQPNGEEMTLKQFLDYFKTEHKLEITMLSQGVSMLYSFFMPAAKLKERLDQPMTEIVSRVSKRKLGRHVRALVLELCC
NDESGEDVEVPYVRYTIRZ

FIGURE 9A

ATGGCGCTGAAACGGATTAATAAGGAACTTAGTGATTTGGCCCGTGACCCTCCAGCACAATGTTCTGCAGGTCCAGTTGG
GGATGATATGTTTCATTGGCAAGCCACAATTATGGGACCTAATGACAGCCCATATCAAGGCGGTGTATTCTTTTTGACAA
TTCATTTTCCTACAGACTACCCCTTCAAACCACCTAAGGTTGCATTTACAACAAGAATTTATCATCCAAATATTAACAGT
AATGGCAGCATTTGTCTCGATATTCTAAGATCACAGTGGTCGCCTGCTTTAACAATTTCTAAAGTTCTTTTATCCATTTG
TTCACTGCTATGTGATCCAAACCCAGATGACCCCCTAGTGCCAGAGATTGCACGGATCTATAAAACAGACAGAGATAAGT
ACAACAGAATATCTCGGGAATGGACTCAGAAGTATGCCATGTGA

FIGURE 9B

MALKRINKELSDLARDPPAQCSAGPVGDDMFHWQATIMGPNDSPYQGGVFFLTIHFPTDYPPKPPKVAFTTRIYHPNINS
NGSICLDILRSQWSPALTISKVLLSICSLLCDPNPDDPLVPEIARIYKTDRDKYNRISREWTQKYAMZ

FIGURE 10

MKVKIKCWNGVATWLWVANDENCGICRMAFNGCCPDCKVPGDDCPLVWGQCSHCFHMHCILKWLHAQQVQQHCPMCRQTW
KFKE

FIGURE 11

MAAAMDVDTPSGTNSGAGKKRFEVKKWNAVALWAWDIVVDNCAICRNHIMDLCIECQANQASATSEECTVAWGVCNHAFHF
HCISRWLKTRQVCPLDNREWEFQKYGH

FIGURE 12A

ATGGCCGACGTGGAAGACGGAGAGGAAACCTGCGCCCTGGCCTCTCACTCCGGGAGCTCAGGCTCAACGTCGGGAGGCGA
CAAGATGTTCTCCCTCAAGAAGTGGAACCCGGTGGCCATGTGGAGCTGGGACGTGGAGTGCGATACGTGCGCCATCTGCA
GGGTCCAGGTGATGGATGCCTGTCTTAGATGTCAAGCTGAAAACAAACAAGAGGACTGTGTTGTGGTCTGGGGAGAATGT
AATCATTCCTTCCACAACTGCTGCATGTCCCTGTGGGTGAAACAGAACAATCGCTGCCCTCTCTGCCAGCAGGACTGGGT
GGTCCAAAGAATCGGCAAATGA

FIGURE 12B

MADVEDGEETCALASHSGSSGSTSGGDKMFSLKKWNPVAMWSWDVECDTCAICRVQVMDACLRCQAENKQEDCVVVWGEC
NHSFHNCCMSLWVKQNNRCPLCQQDWVVQRIGK

FIGURE 13A

```
ATGGCGACGTCTAATCTGTTAAAGAATAAAGGTTCTCTTCAGTTTGAAGACAAATGGGATTTTATGCGCCCGATTGTTTT
GAAGCTTTTACGCCAGGAATCTGTTACAAAACAGCAGTGGTTTGATCTGTTTTCGGATGTGCATGCAGTCTGTCTTTGGG
ATGATAAAGGCCCAGCAAAAATTCATCAGGCTTTAAAAGAAGATATTCTTGAGTTTATTAAGCAGGCACAGGCACGAGTA
CTGAGCCATCAAGATGATACGGCTTTGCTAAAAGCATATATTGTTGAATGGCGAAAGTTCTTTACACAATGTGATATTTT
ACCAAAACCTTTTTGTCAACTAGAGATTACTTTAATGGGTAAACAGGGCAGCAATAAAAAATCAAATGTGGAAGACAGTA
TTGTTCGAAAGCTTATGCTTGATACATGGAATGAGTCAATCTTTTCAAACATAAAAAACAGACTCCAAGATAGTGCAATG
AAGCTGGTACATGCTGAGAGATTGGGAGAAGCTTTTGATTCTCAGCTGGTTATTGGAGTAAGAGAATCCTATGTTAACCT
TTGTTCTAATCCTGAGGATAAACTTCAAATTTATAGGGACAATTTTGAGAAGGCATACTTGGATTCAACAGAGAGATTTT
ATAGAACACAAGCACCCTCGTATTTACAACCAAATGGTGTACAGAATTATATGAAATATGCAGATGCTAAATTAAAAGAA
GAAGAAAAACGAGCACTACGTTATTTAGAAACAAGACGAGAATGTAACTCCGTTGAAGCACTCATGGAATGCTGTGTAAA
TGCCCTGGTGACATCATTTAAAGAGACTATCTTAGCTGAGTGCCAAGGCATGATCAAGAGAAATGAAACTGAAAATTAC
ATTTAATGTTTTCATTGATGGACAAAGTTCCTAATGGTATAGAGCCAATGTTGAAAGACTTGGAGGAACATATCATTAGT
GCTGCCTGGCAGATATGGTAGCAGCTGCTGAAACTATTACTACTGACTCTGAGAAATACGTTGAGCAGTTACTTACACT
ATTTAATAGATTTAGTAAACTCGTCAAAGAAGCTTTTCAAGATCATCCACGATTTCTTACTGCAAGAGATAAGGCGTATA
AAGCAGTTGTTAATGATGCTACCATATTTAAACTTGAATTACCTTTGAAGCAGAAGGGGGTGGGATTAAAAACTCAGCCT
GAATCAAAATGCCCTGAGCTGCTTGCCAATTACTGTGACATGTTGCTAAGAAAAACACCATTAAGCAAAAAACTAACCTC
TGAAGAGATTGAAGCAAAGCTTAAAGAAGTGCTCTTGGTACTTAAGTATGTACAGAACAAAGATGTTTTTATGAGGTATC
ATAAAGCTCATTTGACACGACGTCTTATATTAGACATCTCTGCCGATAGTGAAATTGAAGAAAACATGGTAGAGTGGCTA
AGAGAAGTTGGTATGCCAGCGGATTATGTAAACAAGCTTGCTAGAATGTTTCAGGACATAAAAGTATCTGAAGATTTGAA
CCAAGCTTTTAAGGAAATGCACAAAAATAATAAATTGGCATTACCAGCTGATTCAGTTAATATAAAAATTCTGAATGCTG
GCGCCTGGTCAAGAAGTTCTGAGAAAGTCTTTGTCTCACTTCCTACTGAACTGGAGGACTTGATACCGGAAGTAGAAGAA
TTCTACAAAAAAAATCATAGTGGTAGAAAATTACATTGGCATCATCTCATGTCAAATGGAATTATAACATTTAAGAATGA
AGTTGGTCAATATGATTTGGAGGTAACCACGTTTCAGCTCGCTGTATTGTTTGCATGGAACCAAAGACCCAGAGAGAAAA
TCAGCTTTGAAAATCTTAAGCTTGCAACTGAACTCCCTGATGCTGAACTTAGGAGGACTTTATGGTCTTTAGTAGCTTTC
CCAAAACTCAAACGGCAAGTTTTTGTATGACCCTCAAGTCAACTCACCCAAAGACTTTACAGAAGGTACCCTCTTCTC
AGTGAACCAGGAGTTCAGTTTAATAAAAATGCAAAGGTTCAGAAAGGGGTAAAATCAACTTGATTGGACGTTTGCAGC
TCACTACAGAAAGGATGAGAGAAGAAGAGAATGAAGGAATAGTTCAACTACGAATACTAAGAACCCAGGAAGCTATCATA
CAAATAATGAAAATGAGAAAGAAAATTAGTAATGCTCAGCTGCAGACTGAATTAGTAGAAATTTTGAAAAACATGTTCTT
GCCACAAAAGAAAATGATAAAAGAGCAAATAGAGTGGCTAATAGAGCACAAATACATCAGAAGAGATGAATCTGATATCA
ACACTTTCATATATATGGCATAA
```

FIGURE 13B

```
MRSFAWGSSGDHVGDKSEEAPGAWDEVSAVGALLQRPPHPGAGPTGPGPWWELRPPVKAWPGRERHHFSRRLVSRESKLK
NMATSNLLKNKGSLQFEDKWDFMRPIVLKLLRQESVTKQQWFDLFSDVHAVCLWDDKGPAKIHQALKEDILEFIKQAQAR
VLSHQDDTALLKAYIVEWRKFFTQCDILPKPPCQLEITLMGKQGSNKKSNVEDSIVRKLMLDTWNESIFSNIKNRLQDSA
MKLVHAERLGEAFDSQLVIGVRESYVNLCSNPEDKLQIYRDNFEKAYLDSTERFYRTQAPSYLQPNGVQNYMKYADAKLK
EEEKRALRYLETRRECNSVEALMECCVNALVTSFKETILAECQGMIKRNETEKLHLMFSLMDKVPNGIEPMLKDLEEHII
SAGLADMVAAAETITTDSEKYVEQLLTLFNRFSKLVKEAFQDDPRFLTARDKAYKAVVNDATIFKLELPLKQKGVGLKTQ
PESKCPELLANYCDMLLRKTPLSKKLTSEEIEAKLKEVLLVLKYVQNKDVFMRYHKAHLTRRLILDISADSEIEENMVEW
LREVGMPADYVNKLARMFQDIKVSEDLNQAFKEMHKNNKLALPADSVNIKILNAGAWSRSSEKVFVSLPTELEDLIPEVE
EFYKKNHSGRKLHWHHLMSNGIITFKNEVGQYDLEVTTFQLAVLFAWNQRPREKISFENLKLATELPDAELRRTLWSLVA
FPKLKRQVFLYDPQVNSPKDFTEGTLFSVNQEFSLIKNAKVQKRGKINLIGRLQLTTERMREEENEGIVQLRILRTQEAI
IQIMKMRKKISNAQLQTELVEILKNMFLPQKKMIKEQIEWLIEHKYIRRDESDINTFIYMA
```

FIGURE 14A

```
ATGGCGGCGGCAGTTGTGGTGGCGGAGGGGGACAGCGACTCCCGGCCCGGACAGGAGTTGTTAGTGGCCTGGAACACCGT
GAGCACCGGCCTGGTGCCGCCGGCTGCGCTGGGGCTGGTGTCTTCCCGGACCAGCGGTGCAGTCCCGCCAAAGGAAGAGG
AGCTCCGGGCGGCGGTGGAGGTTCTGAGGGGCCACGGGCTACACTCGGTCCTGGAGGAGTGGTTCGTGGAGGTGCTGCAG
AACGATCTGCAGGCCAACATCTCCCCTGAGTTCTGGAATGCCATCTCCCAATGCGAGAACTCTGCGGATGAGCCCAGTG
CCTTTTGCTACTCCTTGACGCTTTTGGCCTGCTGCTGGAGAGCCGCCTGGATCCCTACCTGCGTAGCCTAGAGCTGCTGGAGA
AATGGACTCGCCTGGGCTTGCTGATGGGCACTGGTGCTCAGGGGCTGCGAGAAGAAGTCCACACTATGTTGCGCGGAGTC
TTGTTCTTTAGCACCCCCAGAACCTTCCAAGAGATGATCCAGCGTCTGTATGGGTGCTTCTTGAGAGTCTATATGCAGAG
TAAGAGGAAGGGGGAAGGGGGCACAGACCCGGAACTGGAAGGGGAGCTGGACAGCCGGTATGCCCGTCGCCGGTACTACC
GGCTCCTGCAGAGCCCGCTGTGTGCAGGGTGCAGCAGTGACAAGCAAGCAAGTGCTGGTGTCGCCAGGCTCTGGAGCAGTTC
CATCAGCTCAGCCAGGTCTTACACAGGCTCAGTCTGCTGGAGCGGGTCAGTGCCGAGGCTGTGACCACCACCCTGCACCA
GGTGACCCGGGAGAGGATGGAGGACCGTTGCCGGGGCGAGTACGAGCGCTCCTTCCTGCGTGAGTTCCACAAGTGGATCG
AGCGGGTGGTCGGCTGGCTCGGCAAGGTGTTCCTGCAGGACGGCCCCGCCAGGCCCGCATCTCCCGAGGCCGGCAACACC
CTGCGCCGCTGGCGCTGCCACGTGCAAAGGTTCTTCTACCGCATCTACGCCAGCCTGCGCATCGAGGAGCTCTTCAGCAT
CGTCCGAGACTTCCCAGACTCCCGGCCAGCCATCGAGGACCTCAAGTACTGCCTGGAGAGGACGGACCAGAGGCAGCAGC
TGCTCGTGTCCCTCAAGGCTGCCCTGGAGACTCGGCTCCTGCATCCAGGCGTCAACACGTGTGACATCATCACCCTCTAT
ATCTCTGCCATCAAGGCGCTGCGCGTGCTGGACCCTTCCATGGTCATCCTGGAGGTGGCCTGTGAGCCTATCCGCCGCTA
CCTGAGGACGCGGGAGGACACAGTGCGGCAGATTGTGGCTGGGCTGACGGGGGACTCGGACGGGACAGGGGACCTGGCTG
TTGAGCTGTCCAAGACCGACCCGGCGAGCCTGGAGACAGGCCAGGACAGTGAGGATGACTCAGGCGAGCCAGAGGACTGG
GTCCCGGACCCTGTGGATGCCGATCCAGGGAAGTCGAGCTCCAAGCGGCGTTCATCGGACATCATCAGCCTGCTGGTCAG
CATCTACGGCAGCAAGGACCTCTTCATCAATGAGTACCGCTCGCTGCTGGCCGACCGCCTGCTGCACCAGTTCAGCTTCA
GCCCCGAGCGGGAGATCCGCAACGTGGAGCTGCTGAAGCTGCGCTTTGGCGAGGCCCCAATGCACTTCTGTGAAGTCATG
CTGAAGGACATGGCGGACTCCCGCCGCATCAATGCCAACATCCGGGAGGAGGATGAGAAGCGGCCAGCAGAGGAGCAGCC
ACCGTTCGGGGTCTACGCTGTCATCCTGTCCAGTGAGTTCTGGCCGCCCTTCAAGGACGAGAAGCTGGAGGTCCCCGAGG
ATATCAGGGCAGCCCTGGAGGCTTACTGCAAGAAGTATGAGCAGCTCAAGGCCATGCGGACCCTCAGTTGGAAGCACACC
CTGGGCCTGGTGACCATGGACGTGGAGCTGGCCGACCGCACGCTGTCTGTGGCGGTCACCCCAGTACAGGCGGTGATCTT
GCTGTATTTTCAGGACCAAGCCAGCTGGACCCTGGAGGAACTGAGCAAGGCGGTGAAAATGCCCGTGGCGCTGCTGCGGC
GGCGGATGTCCGTGTGGCTGCAGCAGGGTGTGCTGCGTGAGGAGCCCCCGGCCACCTTCTCTGTCATTGAGGAGGAGCGG
CCTCAGGACCGGGACAACATGGTGCTCATTGACAGTGACGACGAGTCCGACAGCGGCATGGCCTCCCAGGCCGACCAGAA
GGAGGAGGAGCTGCTGCTCTTCTGGACGTACATCCAGGCCATGCTGACCAACCTGGAGAGCCTCTCACTGGATCGTATCT
ACAACATGCTCCGCATGTTTGTGGTGACTGGGCCTGCACTGGCCGAGATTGACCTGCAGGAGCTGCAGGGCTACCTGCAG
AAGAAGGTGCGGGACCAGCAGCTCGTCTACTCGGCCGGCGTCTACCGCCTGCCCAAGAACTGCAGCTGA
```

FIGURE 14B

```
MAAAVVVAEGDSDSRPGQELLVAWNTVSTGLVPPAALGLVSSRTSGAVPPKEEELRAAVEVLRGHGLIISVLEEWFVEVLQ
NDLQANISPEFWNAISQCENSADEPQCLLLLLDAFGLLESRLDPYLRSLELLEKWTRLGLLMGTGAQGLREEVHTMLRGV
LFFSTPRTFQEMIQRLYGCFLRVYMQSKRKGEGGTDPELEGELDSRYARRRYYRLLQSPLCAGCSSDKQQCWCRQALEQF
HQLSQVLHRLSLLERVSAEAVTTTLHQVTRERMEDRCRGEYERSFLREFHKWIERVVGWLGKVFLQDGPARPASPEAGNT
LRRWRCHVQKFFYRIYASLRIEEELFSIVRDFPDSRPAIEDLKYCLERTDQRQQLLVSLKAALETRLLHPGVNTCDIITLY
ISAIKALRVLDPSMVILEVACEPIRRYLRTREDTVRQIVAGLTGDSDGTGDLAVELSKTDPASLETGQDSEDDSGEPEDW
VPDPVDADPGKSSSKRRSSDIISLLVSIYGSKDLFINEYRSLLADRLLHQFSFSPEREIRNVELLKLRFGEAPMHFCEVM
LKDMADSRRINANIREEDEKRPAEEQPPFGVYAVILSSEFWPPFKDEKLEVPEDIRAALEAYCKKYEQLKAMRTLSWKHT
LGLVTMDVELADRTLSVAVTPVQAVILLYFQDQASWTLEELSKAVKMPVALLRRRMSVWLQQGVLREEPPGTFSVIEEER
PQDRDNMVLIDSDDESDSGMASQADQKEEELLLFWTYIQAMLTNLESLSLDRIYNMLRMFVVTGPALAEIDLQELQGYLQ
KKVRDQQLVYSAGVYRLPKNCS
```

FIGURE 15A

MQIFVKTLTGKTITLEVEPSDTIENVKAKIQDKEGIPPDQQRLIFAGKQLEDGRTLSDYNIQKESTLHLVLRLRGG

FIGURE 15B

MDYKDDDDKQIFVKTLTGKTITLEVEPSDTIENVKAKIQDKEGIPPDQQRLIFAGKQLEDGRTLSDYNIQKESTLHLVLRLRGG

FIGURE 15C

MDYKDDDDKCQIFVKTLTGKTITLEVEPSDTIENVKAKIQDKEGIPPDQQRLIFAGKQLEDGRTLSDYNIQKESTLHLVLRLRGG

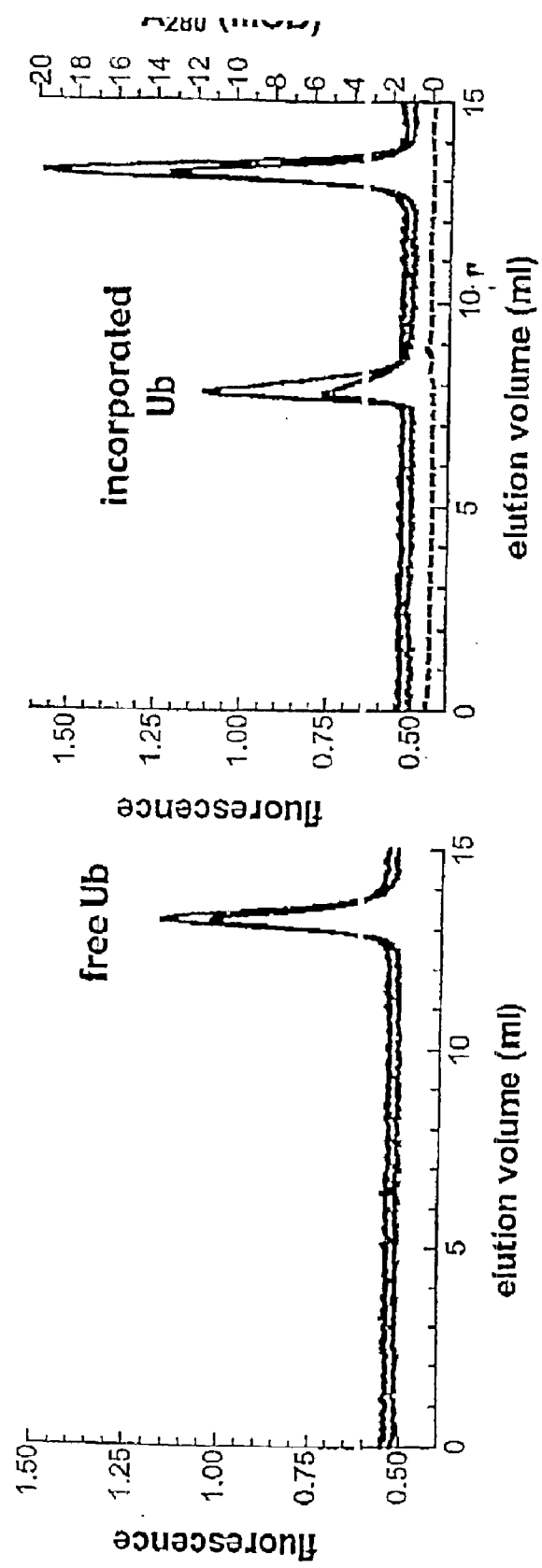

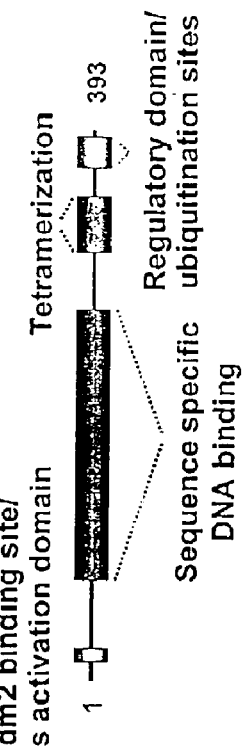
Figure 18

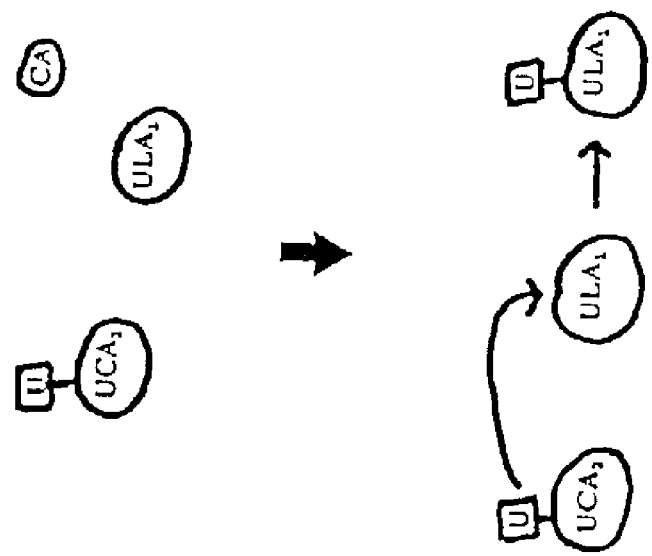
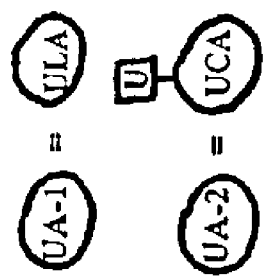
Figure 27

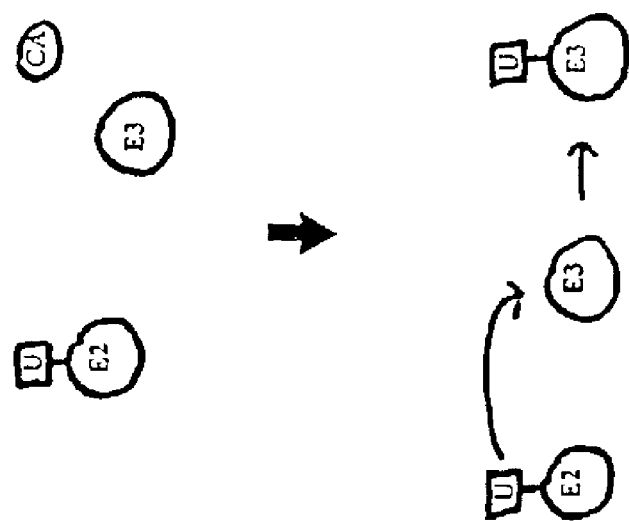
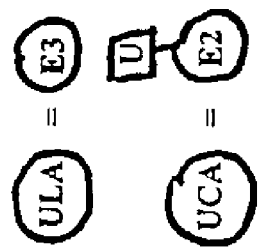
Figure 28

UA-3 = ULA

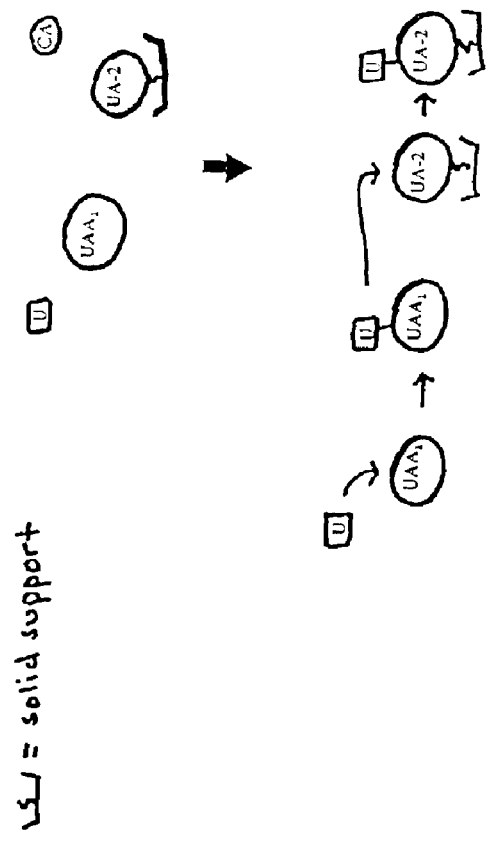

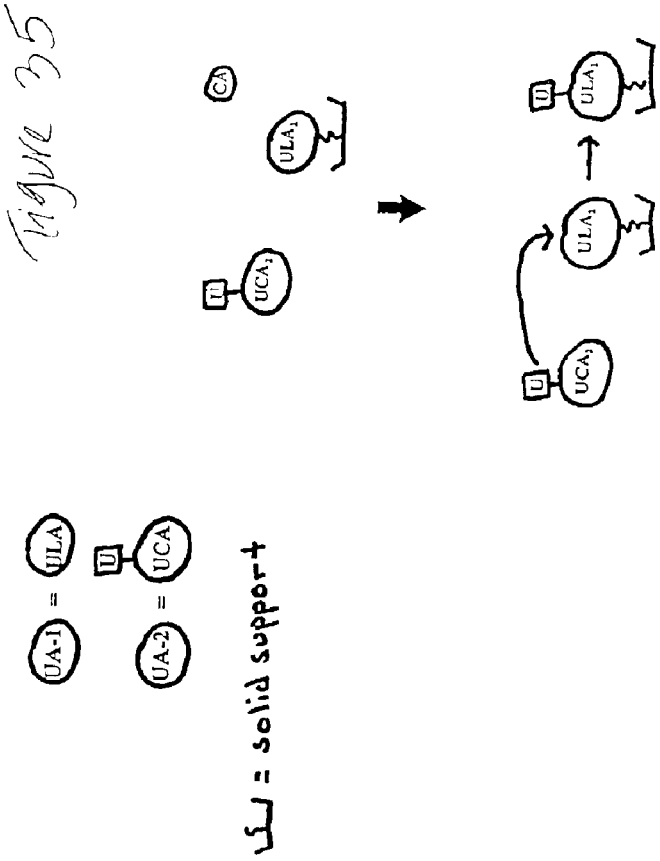

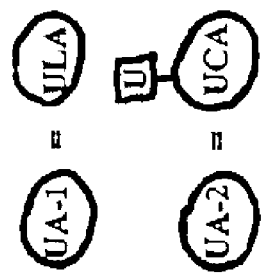
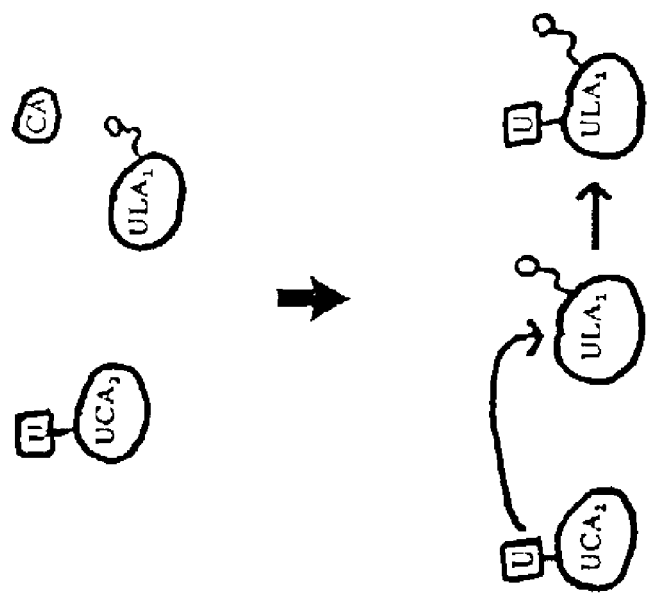
Figure 37

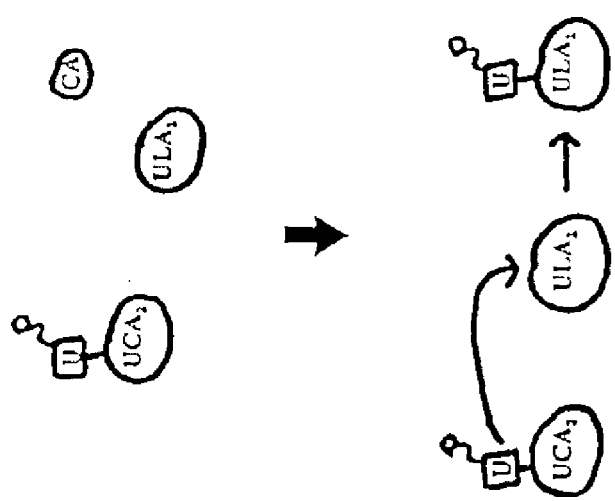
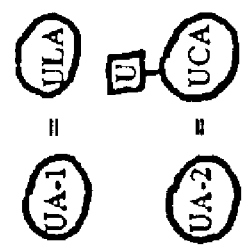
Figure 4D

Figure 41
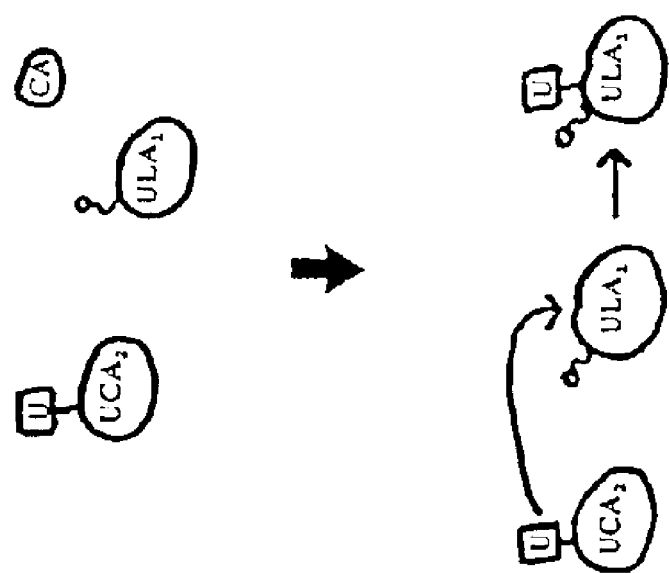
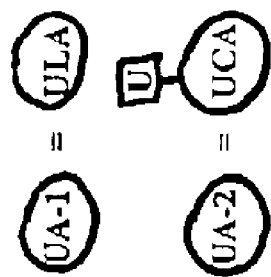

⊡ = attachment moiety

Figure 44
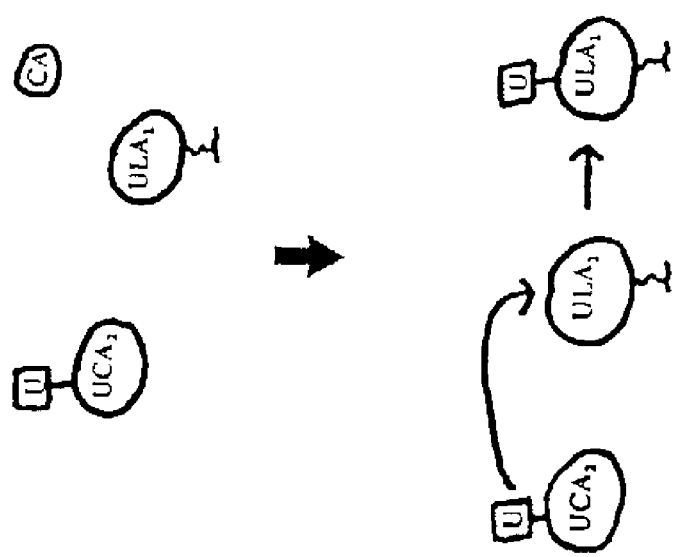
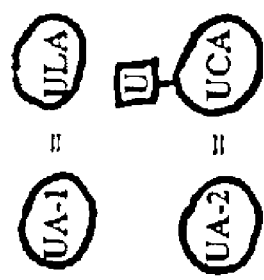
⊡ = attachment moiety

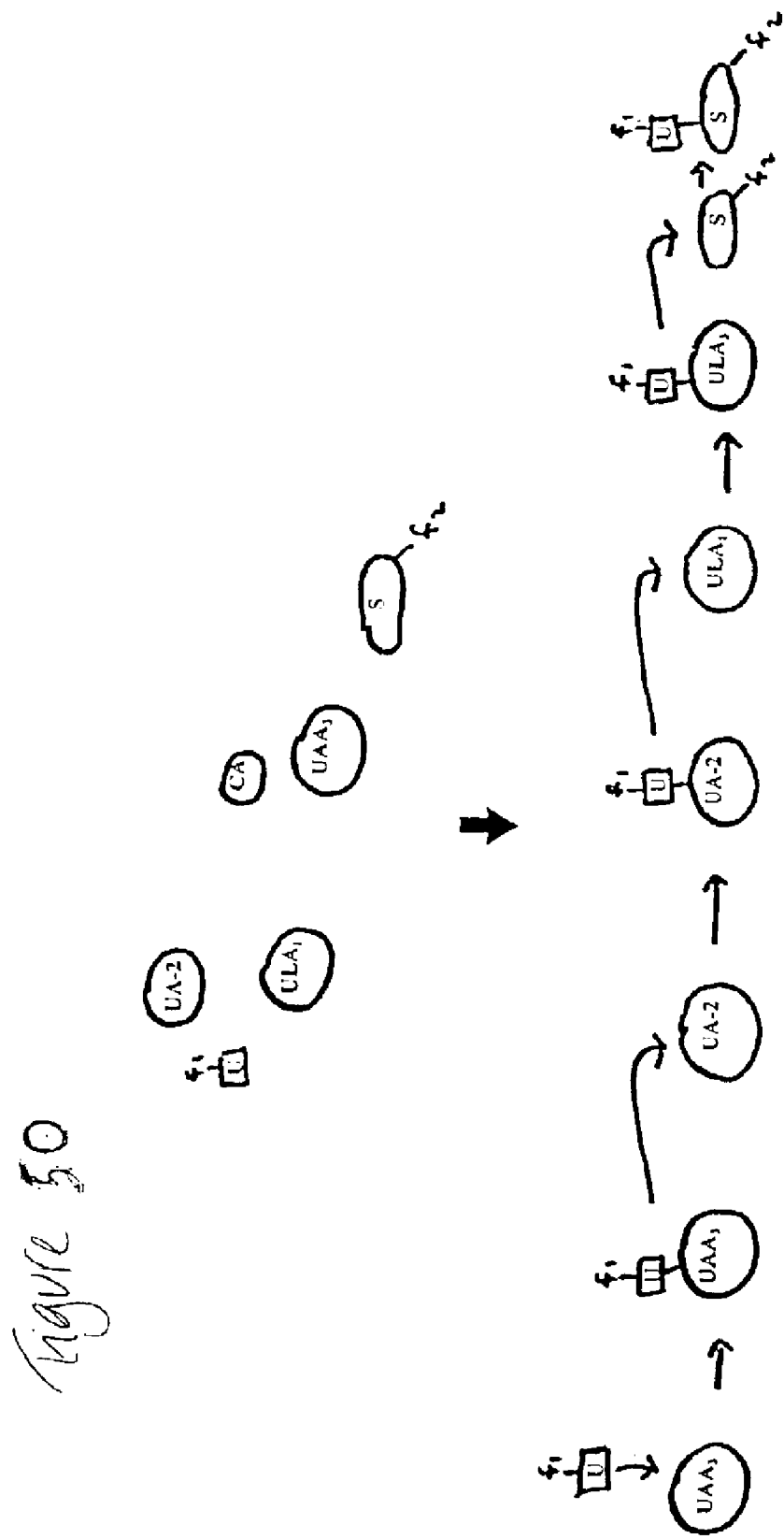

FIGURE 51
UBC7

FIGURE 51A
  1 mtelqsalll rrqlaelnkn pvegfsagli ddndlyrwev liigppdtly eggvfkahlt
 61 fpkdyplrpp kmkfiteiwh pnvdkngdvc isilhepged kygyekpeer wlpihtveti
121 misvismlad pngdspanvd aakewredrn gefkrkvarc vrksqetafe FIGURE 51B
  1 atgacggagc tgcagtcggc actgctactg cgaagacagc tggcagaact caacaaaaat
 61 ccagtggaag gctttctgc aggtttaata gatgacaatg atctctaccg atgggaagtc
121 cttattattg gccctccaga tacactttat gaaggtggtg tttttaaggc tcatcttact
181 ttcccaaaag attatcccct ccgacctcct aaaatgaaat tcattacaga aatctggcac
241 ccaaatgttg ataaaaatgg tgatgtgtgc atttctattc ttcatgagcc tggggaagat
301 aagtatggtt atgaaaagcc agaggaacgc tggctcccta tccacactgt ggaaaccatc
361 atgattagtg tcatttctat gctggcagac cctaatggag actcacctgc taatgttgat
421 gctgcgaaag aatggaggga agataagaaat ggagaattta aagaaaagt tgcccgctgt
481 gtaagaaaaa gccaagagac tgcttttgag tga

FIGURE 52

UBC7 homolog

FIGURE 52A
1    magtalkrlm aeykqltlnp pegivagpmn ecnffeweal imgpedtcfe fgvfpailsf
61   pldyplsppk mrftcemfhp niypdgrvci silhapgddp mgyessaerw spvqsvekil
121  lsvvsmlacp ndesganvda skmwrddreq fykiakqivq kslgl FIGURE 52B1
1    cgcgcggctg aggcgaggtc gctcggcgca gctgttgcgg ggccatggcg
     gggaccgcgc
61   tcaagaggct gatggccgag tacaaacaat taacactgaa tcctccggaa
     ggaattgtag
121  caggccccat gaatgaagag aactttttg aatgggaggc attgatcatg
     ggcccagaag
181  acacctgctt tgagtttggt gttttcctg ccatcctgag tttcccactt
     gattacccgt
241  taagtccccc aaagatgaga tttacctgtg agatgtttca tcccaacatc
     taccctgatg
301  ggagagtctg catttccatc ctccacgcgc caggcgatga cccatgggc
     tacgagagca
361  gcgcggagcg gtggagtcct gtgcagagtg tggagaagat cctgctgtcg
     gtggtgagca
421  tgctggcaga gcccaatgac gaaagtggag ctaacgtgga tgcgtccaaa
     atgtggcgcg
481  atgaccggga gcagttctat aagattgcca agcagatcgt ccagaagtct
     ctgggactgt
541  gagacctggc ctcgcacagg cgcgcacaca ccgccaagca gctcagcatt
     ctccccgc
601  acacttagtg acagtgatgc tctgtgctgg taccaaacaa ggcagacttg
     caagaaccat
661  ggcatctttt ttttttttca aacctttcct acttcaaaca ggcttctctt
     ctgaaatgat
721  gacttaatgt cgaatattga cagcttactg cagttttaca gtattcctca
     caaagggctt
781  caggtagatt atcagagctg tcagcactac ctctccccgc tgaaaccagc
     agttcatggc
841  ttcctgtgga ttccctccct ccctggagtg ttgagggggt tgtacctgcc
     agacttccag
901  gggacgatgg aatacccaga acgctccttc tgaagaaatg gggccctgta
     gctgcagcac
961  aggggaaggg cccggcaccc ttcctgggtc cttcctggtt ccctgtgggc
     cccatgagga
1021 gtccattact tcctttcttc cttcatattt tacaggcaga tgcttttctt
     ataatctaat
1081 tacatctttt catttgttat atattacaaa ccatcacact tagaaatact
     tccaggaaat
1141 gcttttttga agtgtgaatt aataagaaat ggggtaaata gaaagaaat
     ttattgctga
1201 ttggccaggt gcggtggttc gtgcctgtaa tcccagctct ttgggaggcc
     aaggcaggta
1261 gatcacaagg tcaggaaatt gagaccatcc tggctaatac agtgaaaccc
     catgtctgct
1321 aaaattacaa aaattagct gggcgtggtg gtgcacgcct gtagtctcag
     ctactcagga
1381 ggctgaggca ggagaatcgc ttgaacccgg gaggcagagg tagcagtgag
     ctgaagtccc

FIGURE 52B2 (CONTINUED)

```
1441 gccactgcac tccagcctgg gcaacagagc gagactcagt ctcaaaaga
aaaagaaat
1501 ttattgctga tcacaaggac agacagtttt ttcccgacca tactcatcaa
agatttacgt
1561 ttgtatatta gtaactagtg cattactaga gcaggtgcag gtgaggtctt
taaagtttca
1621 atgaaagttt cttctggatc tacagaaaaa atttttttt ttcaatctaa
aaactggaaa
1681 ttctagggtt tttgtacatt ttggatgcac tgggaattta ttagcacaaa
atcattcttt
1741 gcaactcaaa attcagaagg gactctacca tatcttagct cagagcacag
aggagtgcct
1801 tatccccaca cttgactggg ctgtggaggt gggcatgtgg gcccctgggc
ccaggctggg
1861 gacagagccc ttgttttgtg acttaggatt ttgatgtggt tccatgttc
tctaacaggg
1921 ccagctgagc agcacaggcc aggaggccac agtgtaagca ataacagatc
tgccacatgc
1981 agaagcaaat atcaggcctg tcgcacacgg gcggcattta aataggaatt
tctatttttg
2041 aaataaggga tggtctatga ggcatacagt agatttgatg tgatcctttt
ctccctccct
2101 tccataatgg atcgtggtct gtgtgactga acccacacag agtgtcatgg
gtgacagttt
2161 ctggttgaag tagctccacg cctggcttct gtggacagca gattctttc
cttctcacaa
2221 ggggctcatt taaaatttgg aggctgggtg ctgtggctca cgcctgcaat
cccagcactt
2281 tgggagactg aggcgggcgg atcatgaggt caggagatcg cgaccatcct
ggctaacagt
2341 gaaaccctgt ctccactaaa aatacaaaaa attagccggg cgtggtggcg
ggcgcctgta
2401 gtcccagcta ctctgaagac tgaggcagga aatggcgtg aacccaggag
gcggagcttg
2461 cagtgagctg agatcacgcc actgcactcc agcctggca acagagtgag
actctgtctc
2521 aaaaaaaaaa aaaaaaaaa tggaacgcag ggcaagaact cgtatttgga
aggagatggg
2581 ggaaggagc ggtattatac ctatgttgta tttgcaggca aatgagatgg
agccctctct
2641 gtaaagaaga gtcatttgtg caagtagacg gggtctgtgg gtgcaggccc
tggaggggca
2701 cacaattgcc tggaggcttc tgtgagatcg ggagagggag gagaggcagt
ctcttgacaa
2761 aataaagtat ttttattcat ttgtatttat taaatgaaaa aacaatccca
tggtgtccct
2821 gttgtgtggt ggaacctaat gactgttgaa ataaagttct gtgttttccc tgccctgc
```

UBC9

FIGURE 53A
1    msgialsrla qerkawrkdh pfgfvavptk npdgtmnlmn wecaipgkkg tpwegglfkl
61   rmlfkddyps sppkckfepp lfhpnvypsg tvclsileed kdwrpaitik qillgiqell
121  nepniqdpaq aeaytiycqn rveyekrvra qakkfaps FIGURE 53B1
1    ggatgggaag cgagcatggt gagtcctcaa gtcgcagctg ggcctgccac
gtgggagtgg
61   agggtggagg aacgtgtgga gtttcggagt ccagcccagt gcgagacagc
cttgaaaccg
121  tggttggcgg gcgctccact ccgctctggg ctcgaaccct gcctgaccct
agctgtgccc
181  cccactttct ccctgtctgg ccctgctcc cgcccctc acttagagga
gggcacgggg
241  aagggcaaac ggtccagagg gcgggcggct gcgggctcct ctgcatcatg
tgaggagggc
301  gtgggaagg acatcctggt ggggcccgat ctgggctgcc tccagcccgg
gcctgtgtct
361  tggacttagt cgtggacctg gaggccagtg cccggctggc cctgtcaccc
tctcgctgtg
421  acgccagcgc ctgctgactg gggaccag gttccttcgc ctgcttttc
tcaggctgcc
481  ctgaggatct gtgtttggtg aaaaggagcc aaattcacct gcagggcagg
cggctctagc
541  agcttcagaa gcctggtgcc ctggcgacac tggacctgcc ttggcttctt
tgatcccaac
601  cccaccccg atttctgctc tgctgactgg ggaagtcatc gtgccaccca
gaacctgagt
661  gcgggcctct cagagctcct tcgtccgtgg gtctgccggg gactgggcct
tgtctccctg
721  gcgagtgcca ggtgaggctg cggcggctcc gacgcaggtg gagctgctga
cctggcccct
781  ttctgcggct gcgagggact ttgaacatgt cggggatcgc cctcagcaga
ctcgcccagg
841  agaggaaagc atggaggaaa gaccacccat ttggtttcgt ggctgtccca
acaaaaaatc
901  ccgatggcac gatgaacctc atgaactggg agtgcgccat tccaggaaag
aaagggactc
961  cgtgggaagg aggcttgttt aaactacgga tgcttttcaa agatgattat
ccatcttcgc
1021 caccaaaatg taaattcgaa ccaccattat ttcacccgaa tgtgtaccct
tcggggacag
1081 tgtgcctgtc catcttagag gaggacaagg actggaggcc agccatcaca
atcaaacaga
1141 tcctattagg aatacaggaa cttctaaatg aaccaaatat ccaagaccca
gctcaagcag
1201 aggcctacac gatttactgc caaaacagag tggagtacga gaaaagggtc
cgagcacaag
1261 ccaagaagtt tgcgccctca taagcagcga ccttgtggca tcgtcagaag
gaagggattg
1321 gtttggcaag aacttgttta caacatttt gcaaatctaa agttgctcca
tacaatgact
1381 agtcacctgg gggggttggg cgggcgccat cttccattgc cgccgcggt
gtgcggtctc

FIGURE 53B2

```
1441 gattcgctga attgcccgtt tccatacagg gtctcttcct tcggtctttt
gtatttttga
1501 ttgttatgta aaactcgctt ttattttaat attgatgtca gtatttcaac
tgctgtaaaa
1561 ttataaactt ttatacttgg gtaagtcccc caggcgagtt cctcgctctg
ggatgcaggc
1621 atgcttctca ccgtgcagag ctgcacttgg cctcagctgg ctgtatggaa
atgcaccctc
1681 cctcctgcgc tcctctctag aacctgggct gtgctgcttt tgagcctcag
accccagggc
1741 agcatctcgg ttctgcgcca cttcctttgt gtttatatgg cgttttgtct
gtgttgctgt
1801 ttaggtaaat aaactgttta tataaaaaaa aaaaaaaaaa aaaaaaaaaa aaaaaa
```

FIGURE 54

UBCH10

FIGURE 54A

```
1   masqnrdpaa tsvaaarkga epsggaargp vgkrlqqelm tlmmsgdkgi safpesdnlf
61  kwvgtihgaa gtvyedlryk lslefpsgyp ynaptvkflt pcyhpnvdtq gnicldilke
121 kwsalydvrt illsiqsllg epnidsplnt haaelwknpt afkkylqety skqvtsqep
```

FIGURE 54B

```
1   ggcacgagcg agttcctgtc tctctgccaa cgccgcccgg atggcttccc aaaaccgcga
61  cccagccgcc actagcgtcg ccgccgcccg taaggagct gagccgagcg ggggcgccgc
121 ccggggtccg gtgggcaaaa ggctacagca ggagctgatg accctcatga tgtctggcga
181 taaagggatt tctgccttcc ctgaatcaga caacctttc aaatgggtag ggaccatcca
241 tggagcagct ggaacagtat atgaagacct gaggtataag ctctcgctag agttccccag
301 tggctaccct tacaatgcgc cacagtgaa gttcctcacg ccctgctatc accccaacgt
361 ggacaccag ggtaacatat gcctggacat cctgaaggaa aagtggtctg ccctgtatga
421 tgtcaggacc attctgctct ccatccagag ccttctagga gaacccaaca ttgatagtcc
481 cttgaacaca catgctgccg agctctggaa aaaccccaca gcttttaaga agtacctgca
541 agaaacctac tcaaagcagg tcaccagcca ggagccctga cccaggctgc ccagcctgtc
601 cttgtgtcgt ctttttaatt tttcttaga tggtctgtcc ttttgtgat ttctgtatag
661 gactctttat cttgagctgt ggtatttttg ttttgttttt gtctttaaa ttaagcctcg
721 gttgagccct tgtatattaa ataatgcat ttttgtcctt ttttaaaaaa aaaaaaaaaa
781 aaa
```

FIGURE 55

UBC13

FIGURE 55A 1 maglprriik etqrllaepv pgikaepdes naryfhvvia gpqdspfegg tfklelflpe
61 eypmaapkvr fmtkiyhpnv dklgricldi lkdkwspalq irtvllsiqa llsapnpddp
121 landvaeqwk tneaqaieta rawtrlyamn ni

FIGURE 55B 1 actcgtgcgt gaggcgagag gagccggaga cgagaccaga ggccgaactc
gggttctgac
61 aagatggccg ggctgccccg caggatcatc aaggaaaccc agcgtttgct
ggcagaacca
121 gttcctggca tcaaagccga accagatgag agcaacgccc gttattttca
tgtggtcatt
181 gctggccctc aggattcccc ctttgaggga gggacttta aacttgaact
attccttcca
241 gaagaatacc caatggcagc ccctaaagta cgtttcatga ccaaaattta
tcatcctaat
301 gtagacaagt tgggaagaat atgtttagat attttgaaag ataagtggtc
cccagcactg
361 cagatccgca cagttctgct atcgatccag gccttgttaa gtgctcccaa
tccagatgat
421 ccattagcaa atgatgtagc ggagcagtgg aagaccaacg aagcccaagc
catagaaaca
481 gctagagcat ggactaggct atatgccatg aataatattt aaattgatac
gatcatcaag
541 tgtgcatcac ttctcctgtt ctgccaagac ttcctcctct ttgtttgcat
ttaatggaca
601 cagtcttaga aacattacag aataaaaaag cccagacatc ttcagtcctt
tggtgattaa
661 atgcacatta gcaaatctat gtcttgtcct gattcactgt cataaagcat
gagcagaggc
721 tagaagtatc atctggattg ttgtgaaacg tttaaaagca gtggcccctc
cctgctttta
781 ttcatttccc ccatcctggt ttaagtataa agcactgtga atgaaggtag
ttgtcaggtt
841 agctgcaggg gtgtgggtgt ttttatttta ttttatttta ttttattttt
gagggggggag
901 gtagtttaat tttatgggct cctttccccc tttttggtg atctaattgc
attggttaaa
961 agcagctaac caggtcttta gaatatgctc tagccaagtc taactttatt
tagacgctgt
1021 agatggacaa gcttgattgt tggaaccaaa atgggaacat taaacaaaca
tcacagccct
1081 cactaataac attgctgtca agtgtagatt ccccccttca aaaaagctt
gtgaccattt
1141 tgtatggctt gtctggaaac ttctgtaaat cttatgtttt agtaaaatat
tttttgttat
1201 tct

ASSAYS FOR IDENTIFYING UBIQUITIN AGENTS AND FOR IDENTIFYING AGENTS THAT MODIFY THE ACTIVITY OF UBIQUITIN AGENTS

This application is a continuation in part of Ser. No. 10/108,767 filed on Mar. 26, 2002 and is a Continuation in part of Ser. No. 10/109,460 filed on Mar. 26, 2002 which was abandoned and is a continuation in part of Ser. No. 10/091,139 filed on Mar. 4, 2002 which was abandoned and is a continuation in part of Ser. No. 10/091,174 filed on Mar. 4, 2002 which was abandoned and is a continuation in part of Ser. No. 09/826,312 filed on Apr. 3, 2001 now U.S. Pat. No. 6,737,244 and is a continuation in part of Ser. No. 09/542,497 filed on Apr. 3, 2000 now U.S. Pat. No. 6,740,495 and claims benefit of 60/291,836 filed on May 18, 2001.

FIELD OF THE INVENTION

The invention relates to the field of ubiquitin-mediated proteolysis. In particular, the invention relates to methods and compositions for assaying for ubiquitin agents that are enzymatic components of ubiquitin-mediated proteolysis and, more particularly, to methods and compositions for assaying for agents that modulate the activity of such ubiquitin agents.

BACKGROUND OF THE INVENTION

Ubiquitin is a highly conserved 76 amino acid protein expressed in all eukaryotic cells. The levels of many intracellular proteins are regulated by a ubiquitin-mediated proteolytic process. This process involves the covalent ligation of ubiquitin to a target protein, resulting in a polyubiquitinated target protein which is rapidly detected and degraded by the 26S proteasome.

The ubiquitination of these target proteins is known to be mediated by the enzymatic activity of three ubiquitin agents. Ubiquitin is first activated in an ATP-dependent manner by a ubiquitin activating agent, for example, an E1. The C-terminus of a ubiquitin forms a high energy thiolester bond with the ubiquitin activating agent. The ubiquitin is then transferred to a ubiquitin conjugating agent, for example, an E2 (also called ubiquitin moiety carrier protein), also linked to this second ubiquitin agent via a thiolester bond. The ubiquitin is finally linked to its target protein to form a terminal isopeptide bond under the guidance of a ubiquitin ligating agent, for example, an E3. In this process, monomers or oligomers of ubiquitin are attached to the target protein. On the target protein, each ubiquitin is covalently ligated to the next ubiquitin through the activity of a ubiquitin ligating agent.

The enzymatic components of the ubiquitination pathway have received considerable attention (for a review, see Weissman, *Nature Reviews* 2:169–178 (2001)). The members of the E1 ubiquitin activating agents and E2 ubiquitin conjugating agents are structurally related and well characterized enzymes. There are numerous species of E2 ubiquitin conjugating agents, some of which act in preferred pairs with specific E3 ubiquitin ligating agents to confer specificity for different target proteins. While the nomenclature for the E2 ubiquitin conjugating agents is not standardized across species, investigators in the field have addressed this issue and the skilled artisan can readily identify various E2 ubiquitin conjugating agents, as well as species homologues (See Haas and Siepmann, *FASEB J.* 11:1257–1268 (1997)).

Generally, ubiquitin ligating agents contain two separate activities: a ubiquitin ligase activity to attach, via an isopeptide bond, monomers or oligomers of ubiquitin to a target protein, and a targeting activity to physically bring the ligase and substrate together. The substrate specificity of different ubiquitin ligating agents is a major determinant in the selectivity of the ubiquitin-mediated protein degradation process.

In eukaryotes, some ubiquitin ligating agents contain multiple subunits that form a complex called the SCF having ubiquitin ligating activity. SCFs play an important role in regulating G1 progression, and consists of at least three subunits, SKP1, Cullins (having at least seven family members) and an F-box protein (of which hundreds of species are known) which bind directly to and recruit the substrate to the complex. The combinatorial interactions between the SCF's and a recently discovered family of RING finger proteins, the ROC/APC11 proteins, have been shown to be the key elements conferring ligase activity to ubiquitin ligating agents. Particular ROC/Cullin combinations can regulate specific cellular pathways, as exemplified by the function of APC11-APC2, involved in the proteolytic control of sister chromatid separation and exit from telophase into G1 in mitosis (see King et al., supra; Koepp et al., *Cell* 97:431–34 (1999)), and ROC1-Cullin 1, involved in the proteolytic degradation of $I_KB$ in NF-$_K$B/$I_K$B mediated transcription regulation (Tan et al., *Mol. Cell* 3(4):527–533 (1999); Laney et al., *Cell* 97:427–30 (1999)).

The best characterized ubiquitin ligating agent is the APC (anaphase promoting complex), which is multi-component complex that is required for both entry into anaphase as well as exit from mitosis (see King et al., *Science* 274:1652–59 (1996) for review). The APC plays a crucial role in regulating the passage of cells through anaphase by promoting ubiquitin-mediated proteolysis of many proteins. In addition to degrading the mitotic B-type cyclin for inactivation of CDC2 kinase activity, the APC is also required for degradation of other proteins for sister chromatid separation and spindle disassembly. Most proteins known to be degraded by the APC contain a conserved nine amino acid motif known as the "destruction box" that targets them for ubiquitin ubiquitination and subsequent degradation. However, proteins that are degraded during G1, including G1 cyclins, CDK inhibitors, transcription factors and signaling intermediates, do not contain this conserved amino acid motif. Instead, substrate phosphorylation appears to play an important role in targeting their interaction with a ubiquitin ligating agent for ubiquitin ubiquitinati on (see Hershko et al., *Ann. Rev. Biochem.* 67:429–75 (1998)).

Two major classes of E3 ubiquitin ligating agents are known: the HECT (homologous to E6-AP carboxy terminus) domain E3 ligating agents; and the RING finger domain E3 ligating agents. E6AP is the prototype for the HECT domain subclass of E3 ligating agents and is a multi-subunit complex that functions as a ubiquitin ligating agent for the tumor suppressor p53 which is activated by papillomavirus in cervical cancer (Huang et al. (1999) Science 286:1321–1326). Members of this class are homologous to the carboxyl terminus of E6AP and utilize a Cys active site to form a thiolester bond with ubiquitin, analogous to the E1 activating agents and E2 conjugating agents. However, in contrast, the members of the RING finger domain class of E3 ligating agents are thought to interact with an ubiquitin—conjugated-E2 intermediate to activate the complex for the transfer of ubiquitin to an acceptor. Examples of the RING domain class of E3 ligating agents are TRAF6, involved in IKK activation; Cbl, which targets insulin and EGF; Sina/Siah, which targets DCC; Itchy, which is involved in haematopoesis (B, T and mast cells);

IAP, involved with inhibitors of apoptosis; and Mdm2 which is involved in the regulation of p53.

The RING finger domain subclass of E3 ligating agents can be further grouped into two subclasses. In one subclass, the RING finger domain and the substrate recognition domain are contained on different subunits of a complex forming the ubiquitin ligating agent (e.g., the RBx1 and the F-box subunit of the SCF complex). In the second subclass of ubiquitin ligating agents, the ligating agents have the RING finger domain and substrate recognition domain on a single subunit. (e.g., Mdm2 and cbl) (Ty ers et al. (1999) Science 284:601, 603–604; Joazeiro et al. (2000) 102:549–552). A further class of ligating agents are those having a "PHD" domain and are homologs of the RING finger domain ligating agents (Coscoy et al. (2001) J. Cell Biol. 155(7):1265–1273), e.g., MEKK1. The PHD domain ligating agents are a novel class of membrane-bound E3 ligating agents.

Mdm2 belongs to the second subclass of single subunit E3 ligating agents and is involved in regulating the function and stability of p53, an important tumor suppressor. In cells, p53 functions as a DNA-binding transcription factor which induces the expression of genes involved in DNA repair, apoptosis, and the arrest of cell growth. In approximately 50% of all human cancer p53 is inactivate by deletion or mutation. The level of p53 in the cell is maintained at low steady-state levels, and is induced and activated post-translationally by various signal pathways responsive to cellular stress (Lakin et al. (1999) Oncogene 18:7644–7655; Oren, M. (1999) J. Biol. Chem 274:36031–36,034). Stimuli that trigger the stress response and activate p53 include oxygen stress, inappropriate activation of oncogenes and agents that cause damage to DNA (e.g., ionizing radiation, chemicals, and ultra violet light).

The carboxyl terminus of Mdm2 contains a variant of the RING finger domain (Saurin et al. (1996) Trends Biochem. Sci. 21:208–214) that is critical for the activity of this E3 ligating agent. Recent studies have shown that Mdm2 mediates the ubiquitination of itself resulting in the formation of poly-ubiquitin chains on the protein (Zhihong et a. (2001) J.B.C. 276:31,357–31,367; Honda et al. (2000) Oncogene 19:1473–1476; Shengyun et al. (2000) 275:8945–8951). Further, the ubiquitin ligating activity of Mdm2 is dependent on its RING finger domain.

Typically, the ubiquitination of target proteins by E3 in cells results in the formation of poly—ubiquitin chains. An isopeptide bond is formed between the carboxyl terminus of the ubiquitin and the E-amino group of Lys in the target protein. The extension or formation of ubiquitin chains results from the formation of additional isopeptide bonds with the $Lys^{48}$ (and sometimes $Lys^{63}$) of a previously conjugated ubiquitin and the carboxyl-terminal Gly of an additional ubiquitin. The efficient recognition of a ubiquitinated target protein by a proteosome requires at least four ubiquitins linked in this configuration. However, in the case of Mdm2-mediated ubiquitination of p53, neither $Lys^{48}$ or $Lys^{63}$ is involved in the formation of poly-ubiquitin chains. Recent studies show that human Mdm2 mediates multiple mono-ubiquitination of p53 by a mechanism requiring enzyme isomerization (Zhihong et al. (2001) J.Biol.Chem. 276:31,357–31,367). Further, in vitro, the transfer of ubiquitin to p53 can occur independent of E1 when using an E2 pre-conjugated with ubiquitin. These results suggest that the pre-conjugated E2 can bind to Mdm2 and thereafter transfer the ubiquitin to the Mdm2 in the absence of an E1.

Thus, ubiquitin agents, such as the ubiquitin activating agents, ubiquitin conjugating agents, and ubiquitin ligating agents, are key determinants of the ubiquitin-mediated proteolytic pathway that results in the degradation of targeted proteins and regulation of cellular processes. Consequently, agents that modulate the activity of such ubiquitin agents may be used to upregulate or downregulate specific molecules involved in cellular signal transduction. Disease processes can be treated by such up- or down regulation of signal transducers to enhance or dampen specific cellular responses. This principle has been used in the design of a number of therapeutics, including phosphodiesterase inhibitors for airway disease and vascular insufficiency, kinase inhibitors for malignant transformation and Proteasome inhibitors for inflammatory conditions such as arthritis.

Due to the importance of ubiquitin-mediated proteolysis in cellular process, for example cell cycle regulation, there is a need for a fast and simple means for identifying ubiquitin agents that are catalytic components of this enzymatic pathway, and for identifying agents that modulate the activity of these catalytic components. Thus, an object of the present invention is to provide methods of assaying for ubiquitin agents that are catalytic components of ubiquitin-mediated proteolysis and, more particularly, methods of assaying for agents that modulate the activity of the ubiquitin agents.

SUMMARY OF THE INVENTION

In accordance with the above objects, the present invention provides methods and compositions for assaying for ubiquitin agents that are enzymatic components of ubiquitin-mediated proteolysis. More particularly, the present invention provides methods and compositions for assaying for an agent that modulates the activity of a ubiquitin agent that is an enzymatic component of ubiquitin-mediated proteolysis. Specifically, the methods of the present invention are directed to identifying ubiquitin agents such as ubiquitin activating agents, ubiquitin conjugating agents, and ubiquitin ligating agents; and to identifying agents that modulate the activity of these ubiquitin agents. In one aspect, the invention provides assaying methods that do not require a ubiquitin target protein. In the methods of the present invention the ubiquitin agents are combined in different combinations with a ubiquitin moiety to assay for the attachment of the ubiquitin moiety, or the modulation of this attachment, to at least one of the following substrate molecules: a ubiquitin agent, a target protein, or a mono- or poly-ubiquitin moiety which is preferably attached to a ubiquitin agent or target protein.

In aspects of the methods and compositions of the present invention, the ubiquitin activating agent is an E1; the ubiquitin conjugating agent is an E2; and/or the ubiquitin ligating agent is an E3. In other aspects, the target protein is a mammalian target protein, and in further aspects, the target protein is a human target protein. In other aspects, the ubiquitin moiety is a mammalian ubiquitin, and in further aspects, the ubiquitin moiety is a human ubiquitin. In another aspect, the ubiquitin moiety is a ubiquitin derivative. In some aspects, the candidate agent a small molecule, and in further aspects, the candidate agent is a peptide. In some aspects, the ubiquitin moiety comprises a label, and in further aspects, the label comprises an epitope tag. In other aspects, at least a first and a second ubiquitin moiety is used, wherein the first and second ubiquitin moieties comprise different fluorescent labels, and wherein the labels form a fluorescence resonance energy transfer (FRET) pair.

In one aspect, the invention provides a method of assaying for an agent that modulates the attachment of a ubiquitin moiety to at least one ubiquitin agent involving the steps of: a) combining a first ubiquitin agent, a candidate agent, and a ubiquitin moiety; and b) assaying for the attachment of the ubiquitin moiety to the first agent. In an additional aspect, the first ubiquitin agent is an ubiquitin activating agent. In a further aspect, the ubiquitin activating agent is an E1.

In another aspect, the method further comprises including a second ubiquitin agent in the combining step. In a further aspect, the first agent is a ubiquitin conjugating agent and the second agent is a ubiquitin activating agent. In a further aspect, the ubiquitin conjugating agent is an E2 and the ubiquitin activating agent is an E1. Also in a further aspect, the ubiquitin conjugating agent is an E2 and the ubiquitin activating agent is an E1 comprising the ubiquitin moiety.

In another aspect, the first agent is a ubiquitin ligating agent and the second agent is a ubiquitin conjugating agent comprises the ubiquitin moiety. In a further aspect, the ubiquitin ligating agent is an E3 and the ubiquitin conjugating agent is an E2 comprising the ubiquitin moiety.

In another aspect, the method further comprises a third ubiquitin agent in the combining step. In a further aspect, the third agent is a ubiquitin ligating agent. Also in a further aspect, the ubiquitin ligating agent is an E3.

In the methods where the assaying concerns the attachment of the ubiquitin moiety to the first ubiquitin agent, the following additional aspects are provided. In one aspect, the first ubiquitin agent comprises a tag. In a further aspect, the first ubiquitin agent comprises an epitope tag. In another aspect, first ubiquitin agent comprises a label. Also in a further aspect, the first ubiquitin agent comprises an attachment tag. In another aspect, the first ubiquitin agent is attached to a solid support; and in a further aspect, the solid support is a microtiter plate or a bead.

In the methods where the assaying concerns the attachment of the ubiquitin moiety to a second ubiquitin agent, the following additional aspects are provided. In one aspect, the second ubiquitin agent comprises a tag. In a further aspect, the second ubiquitin agent comprises an epitope tag. In another aspect, second ubiquitin agent comprises a label. Also in a further aspect, the second ubiquitin agent comprises an attachment tag. In another aspect, the second ubiquitin agent is attached to a solid support, and in a further aspect, the solid support is a microtiter plate or a bead.

In another aspect, the invention provides a method of assaying for an agent that modulates the attachment of a ubiquitin moiety to at least one ubiquitin agent involving the steps of: a) combining a first ubiquitin agent comprising a ubiquitin ligating agent; a second ubiquitin agent, a candidate agent, a ubiquitin moiety, and a substrate; and b) assaying for the attachment of the ubiquitin moiety to the first agent. In an additional aspect, the second agent is a ubiquitin conjugating agent comprising the ubiquitin moiety.

In an additional aspect, the method further comprises a third ubiquitin agent in the combining step, wherein the third agent is a ubiquitin activating agent; wherein the substrate and the ubiquitin moiety comprise different fluorescent labels, and wherein the labels form a fluorescence resonance energy transfer (FRET) pair.

In the following aspects of the present invention, the ubiquitin ligating agent is preferably an Mdm2 protein and the target protein is preferably p53. In a preferred embodiment, the ubiquitin ligating agent is an Mdm2 fusion protein, and more preferably an Mdm2-GST fusion protein.

In one aspect of the present methods, the Mdm2 protein comprises a first FRET label and the ubiquitin moiety comprises a second FRET label. In another aspect, the Mdm2 protein comprises an attachment tag. In another aspect, the Mdm2 protein is provided on a solid support; and in a further aspect, the solid support comprises a microtiter plate or a bead. In another aspect, the Mdm2 protein is a mammalian Mdm2, and in a further aspect, the Mdm2 is a human Mdm2.

In another aspect, the p53 protein comprises a first FRET label and the ubiquitin moiety comprises a second FRET label. In another aspect, the p53 protein comprises an attachment tag. In another aspect, the p53 protein is provided on a solid support; and in a further aspect, the solid support comprises a microtiter plate or a bead.

In one aspect, the invention provides a method of assaying for a candidate agent that modulates the attachment of a ubiquitin moiety to an Mdm2 protein involving the steps of: a) combining a first ubiquitin agent comprising at least one ubiquitin moiety, an Mdm2 protein, and a candidate agent; and b) assaying for the attachment of the ubiquitin moiety to the Mdm2 protein. In an additional aspect, the first ubiquitin agent is a ubiquitin conjugating agent.

In an additional aspect, the method further comprises combining a ubiquitin activating agent comprising the ubiquitin moiety, thereby forming the ubiquitin conjugating agent comprising the ubiquitin moiety, in step a).

In an additional aspect, the method further comprises combining a ubiquitin activating agent and the ubiquitin moiety, thereby forming the ubiquitin conjugating agent comprising the ubiquitin moiety.

In another aspect, the invention provides a method of assaying for a candidate agent that modulates the attachment of a ubiquitin moiety to a p53 protein involving the steps of: a) combining a conjugating agent comprising at least one ubiquitin moiety, an Mdm2 protein, a p53 protein, and a candidate agent; and b) assaying for the attachment of the ubiquitin moiety to the p53 protein.

In an additional aspect, the method further comprises combining a ubiquitin conjugating agent and the ubiquitin moiety, thereby forming the ubiquitin conjugating agent comprising the ubiquitin moiety.

In an additional aspect, the method further comprises combining a ubiquitin activating agent comprising the ubiquitin moiety, thereby forming the ubiquitin conjugating agent comprising the ubiquitin moiety, in step a).

In an additional aspect, the method further comprises combining a ubiquitin activating agent and the ubiquitin moiety, thereby forming the ubiquitin conjugating agent comprising the ubiquitin moiety.

In another aspect, the invention provides a method of assaying for a candidate agent that modulates the attachment of a ubiquitin moiety to an Mdm2 protein involving the steps of: a) combining a ubiquitin activating agent, a ubiquitin conjugating agent, an Mdm2 protein, a candidate agent, and a ubiquitin moiety; and b) assaying for the attachment of the ubiquitin moiety to the Mdm2 protein.

In another aspect, the invention provides a method of assaying for a candidate agent that modulates the attachment of a ubiquitin moiety to a p53 protein involving the steps of: a) combining a ubiquitin activating agent, a ubiquitin conjugating agent, an Mdm2 protein, a p53 protein, a candidate agent, and a ubiquitin moiety; and b) assaying for the attachment of the ubiquitin moiety to the p53 protein.

In another aspect, the invention provides a method of assaying for a candidate agent that modulates the attachment of a second ubiquitin moiety to a p53 protein involving the steps of: a) combining a ubiquitin activating agent, a ubiquitin conjugating agent, an Mdm2 protein, a p53 protein comprising a first ubiquitin moiety, wherein the first ubiquitin moiety is labeled with a first FRET label, a candidate agent, and a second ubiquitin moiety labeled with a second FRET label; and b) assaying for the attachment of the second ubiquitin moiety to the p53 protein by detecting a FRET reaction.

In another aspect, the invention provides a method of assaying for a candidate agent that modulates the attachment of a first ubiquitin moiety to a p53 protein involving the steps of: a) combining a ubiquitin conjugating agent comprising a first ubiquitin moiety labeled with a first FRET, an Mdm2 protein, a p53 protein comprising a second ubiquitin moiety, wherein the first ubiquitin moiety is labeled with a second FRET label, and a candidate agent; and b) assaying for the attachment of the first ubiquitin moiety to the p53 protein by detecting a FRET reaction.

In another aspect, the invention provides a method of assaying for a candidate agent that modulates the attachment of a first ubiquitin moiety to a p53 protein involving the steps of: a) combining a ubiquitin activating agent comprising a first ubiquitin moiety labeled with a first FRET, a ubiquitin conjugating agent, an Mdm2 protein, a p53 protein comprising a second ubiquitin moiety, wherein the first ubiquitin moiety is labeled with a second FRET label, and a candidate agent; and b) assaying for the attachment of the first ubiquitin moiety to the p53 protein by detecting a FRET reaction.

Other aspects of the invention will become apparent to the skilled artisan from the following description of the invention.

BRIEF DESCRIPTION OF THE DRAWINGS

FIG. 3 shows relative amounts of attachment of ubiquitin moiety to an E3 resulting from combining E1, E2, E3, and ubiquitin moiety.

FIG. 5 shows the concentration-dependent effect of two candidate agents that modulate the attachment of ubiquitin moiety to an using two different E3 ubiquitin ligating agents.

FIG. 6 shows the proportions of attachment of ubiquitin moiety to an E3 and attachment of ubiquitin moiety to an E2, in the presence and absence of two candidate agents that modulate the attachment of ubiquitin moiety to an E3 by combining ubiquitin moiety, and E1, E2, and E3 ubiquitin agents and by combining ubiquitin moiety and E1 and E2 ubiquitin agents.

FIG. 7 shows the concentration-dependent effects of two candidate agents that modulate the attachment of ubiquitin moiety to an E3 and the attachment of ubiquitin moiety to an E2.

FIGS. 8A and 8B show the nucleic acid sequence encoding rabbit E1 ubiquitin activating agent and the amino acid sequence of rabbit E1, respectively.

FIGS. 9A and 9B show the nucleic acid sequence encoding the E2 Ubch5c and the amino acid sequence of the E2 Ubch5c, respectively.

FIG. 10 shows the amino acid sequence of the RING finger protein APC11.

FIG. 11 shows the amino acid sequence of the RING finger protein ROC1.

FIGS. 12A and 12B show the nucleic acid sequence encoding the RING finger protein ROC2 and the amino acid sequence of ROC2, respectively.

FIGS. 13A and 13B show the nucleic acid sequence encoding the Cullin CUL5 and the amino acid sequence of CUL5, respectively.

FIGS. 14A and 14B show the nucleic acid sequence encoding the Cullin APC2 and the amino acid sequence of APC2, respectively.

FIGS. 15A, 15B and 15C show the amino acid sequences of human ubiquitin moiety, Flag-ubiquitin moiety and Flag-Cys-ubiquitin moiety, respectively. The Flag and Flag-Cys portions of the sequence are shown in bold.

FIGS. 16A and 16B show the E3-dependent incorporation of Flag-Ala-Cys-ubiquitin moiety labeled with FRET fluorophores into E3-ubiquitin moiety complex. Isolation by HPLC shows emissions from free ubiquitin moiety and ubiquitin moiety a ttached to the E3 ubiquitin ligating agent. The traces show fluorescent emission at the wavelength described below, under excitation at 336 nm, the optimal excitation wavelength for IAEDANS. FIG. 16A shows the fluorescence signals of IAEDANS (490 nm; larger peak) and fluorescein (515 nm; smaller peak) labeled ubiquitin moiety following combination with E1 and E2 only. The free ubiquitin moiety was isolation using high performance liquid chromatography (HPLC). FIG. 16B shows the fluorescence signals of IAEDANS (490 nm; larger peak at each elution volume) and fluorescein (515 nm; smaller peak at each elution volume) labeled ubiquitin moiety following combination with E1 and E2 and E3 (Roc1/Cul1). The dashed line shows optical density of the protein solution (scale on right), revealing the high sensitivity of the fluorophores despite a very low concentration of protein.

FIG. 18 shows a schematic representation of GST-Mdm2 and His-p53.

FIG. 27 schematically depicts a preferred embodiment for assaying for the attachment of ubiquitin moiety to a first ubiquitin agent that is a ubiquitin ligating agent (ULA$_1$) where the assay comprises:

1) combining a second ubiquitin agent that is a ubiquitin conjugating agent and comprising a ubiquitin moiety UCA$_2$-U+ULA$_1$+CA; and
2) assaying for the attachment of the ubiquitin moiety to ULA$_1$. In another preferred embodiment, the ubiquitin moiety comprises a label. In yet another preferred embodiment, ULA$_1$ comprises a label. In a preferred embodiment the ubiquitin ligating agent comprises an Mdm2 protein.

FIG. 28 schematically depicts a preferred embodiment for assaying for the attachment of ubiquitin moiety to a a ubiquitin ligating agent that is an E3 where the assay comprises:
1) combining a ubiquitin conjugating agent that is an E2 and comp rising a ubiquitin moiety+E3+CA; and
2) assaying for the attachment of the ubiquitin moiety to E3. In a preferred embodiment, the E3 is an Mdm2 protein.

Figure 29:
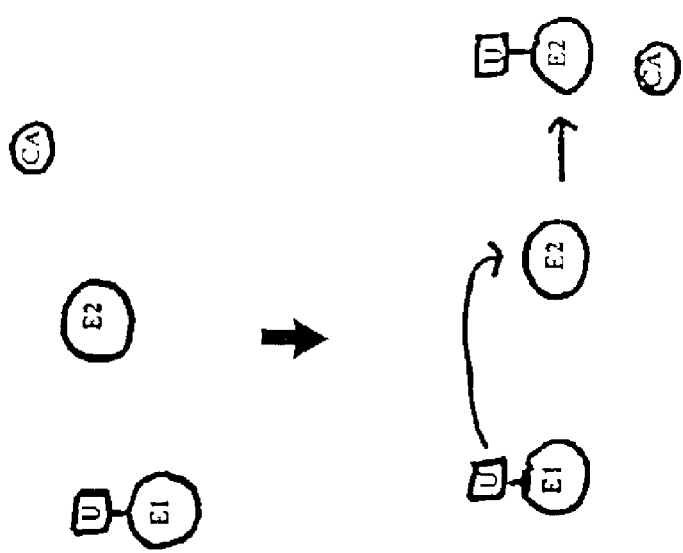

FIG. 29 schematically depicts a preferred embodiment for assaying for the attachment of ubiquitin moiety to a ubiquitin conjugating agent that is an E2 where the assay comprises:
1) combining a ubiquitin activating agent that is an E1 and comprising a ubiquitin moiety+E2+CA; and
2) assaying for the attachment of the ubiquitin moiety to E2.

Figure 30:
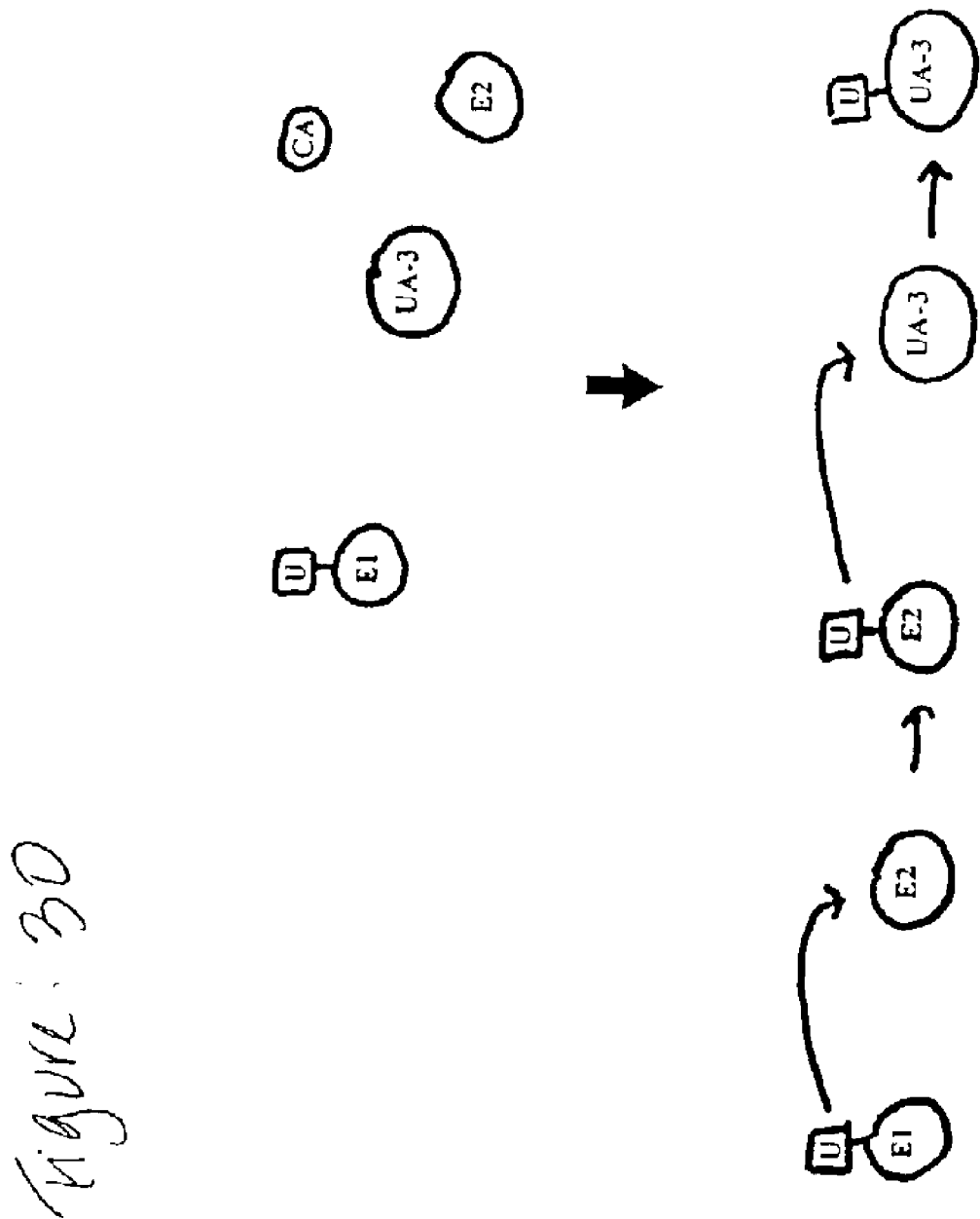

FIG. 30 schematically depicts a preferred embodiment for assaying for the attachment of ubiquitin moiety to a third ubiquitin agent (UA-3) where the assay comprises:
1) combining a ubiquitin activating agent that is an E1 and comprising a ubiquitin moiety+a ubiquitin conjugating agent that is an E2+UA-3+CA; and
2) assaying for the attachment of the ubiquitin moiety to UA-3. In a preferred embodiment, UA-3 comprises an Mdm2 protein.

Figure 31:
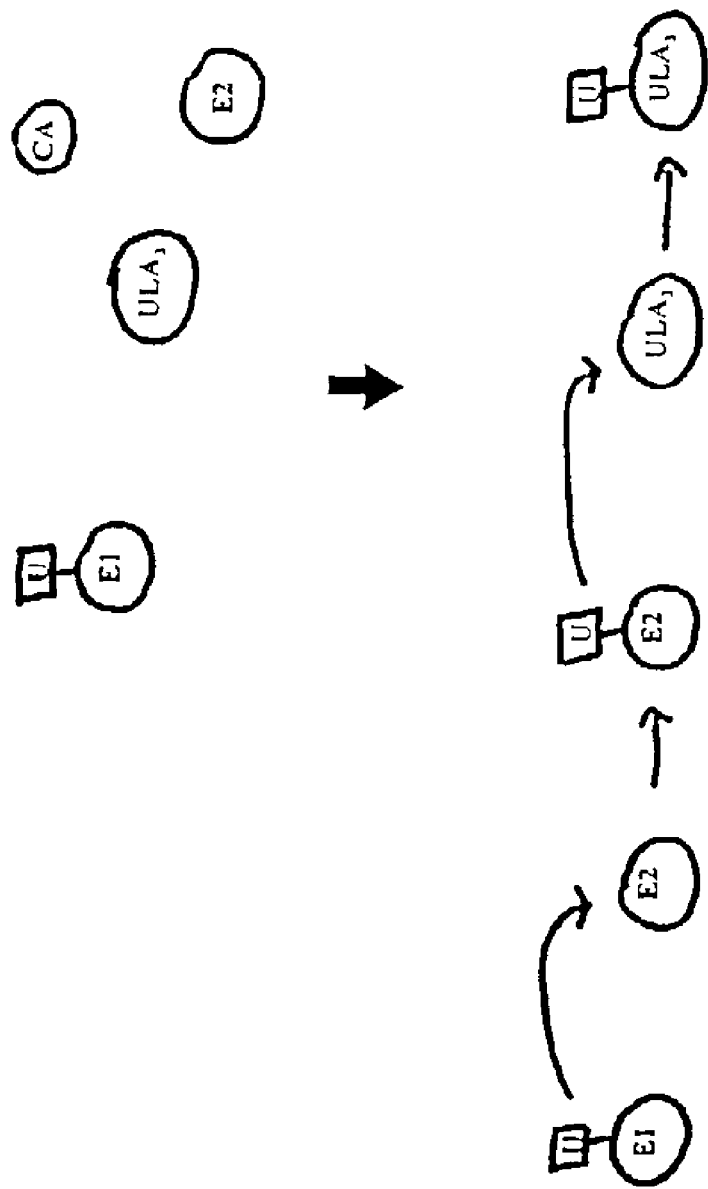

FIG. 31 schematically depicts a preferred embodiment for assaying for the attachment of ubiquitin moiety to a third ubiquitin agent that is a ubiquitin ligating agent (ULA$_3$) where the assay comprises:
1) combining a ubiquitin activating agent that is an E1 and comprising a ubiquitin moiety+a ubiquitin conjugating agent that is an E2+ULA$_3$+CA; and
2) assaying for the attachment of the ubiquitin moiety to ULA$_3$. In a preferred embodiment the ubiquitin ligating agent comprises an Mdm2 protein.

Figure 32:
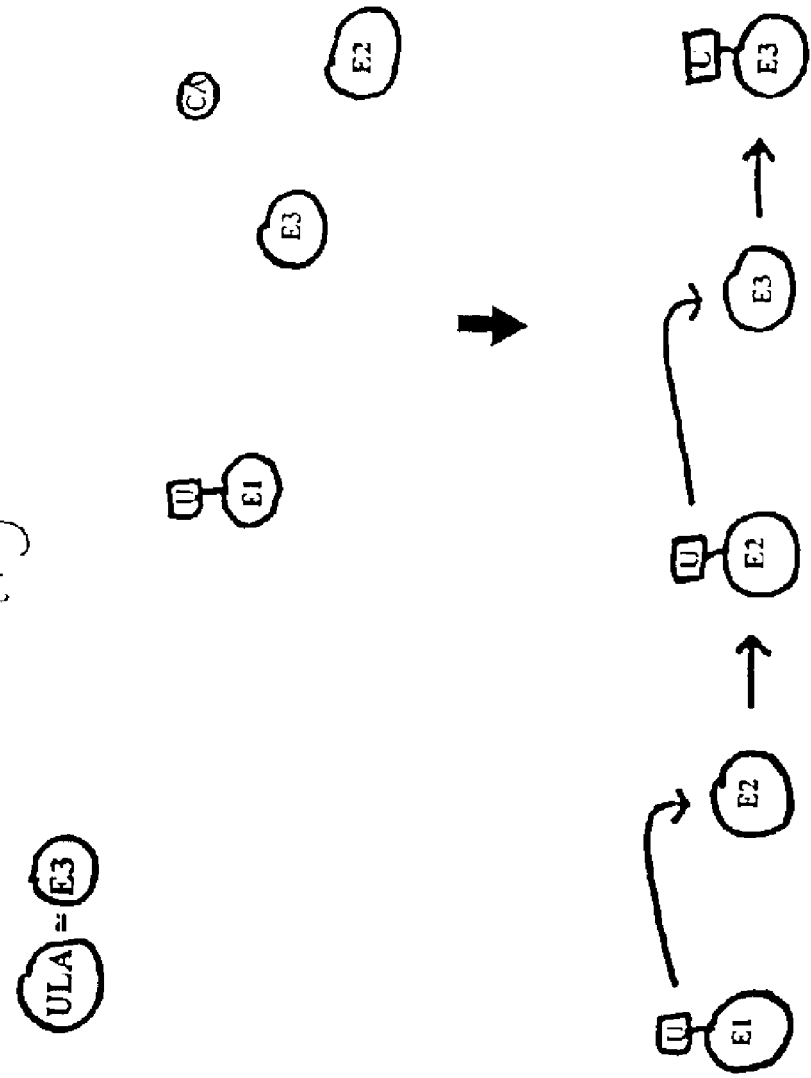

FIG. 32 schematically depicts a preferred embodiment for assaying for the attachment of ubiquitin moiety to a ubiquitin ligating agent that is an E3 where the assay comprises:
1) combining an E1 comprising a ubiquitin moiety+an E2+an E3+CA; and
2) assaying for the attachment of the ubiquitin moiety to E3. In a preferred embodiment, the E3 is Mdm2.

Figure 33:
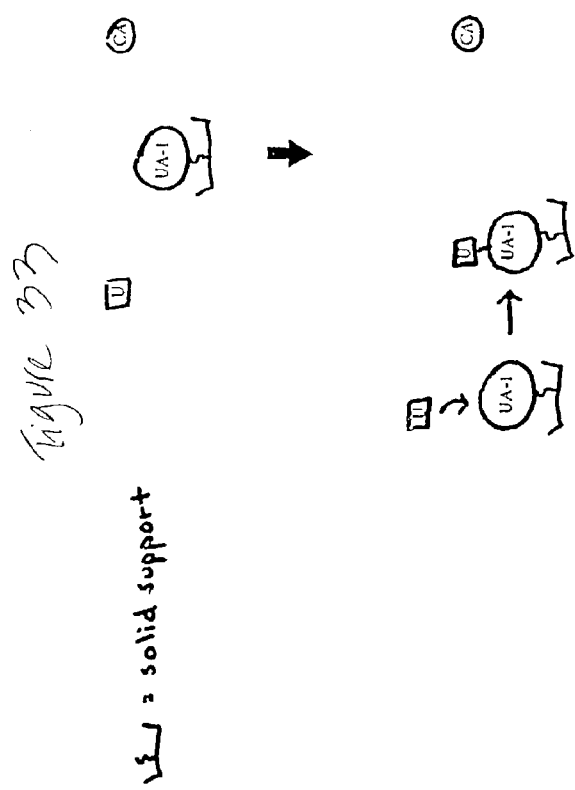

FIG. 33 schematically depicts a preferred embodiment for assaying for the attachment of ubiquitin moiety to a first ubiquitin agent (UA-1) that is attached to a solid support where the assay comprises:
1) combining a UA-1 (that is attached to a solid support)+CA+U; and
2) assaying for the attachment of the ubiquitin moiety to UA-1. In another preferred embodiment UA-1 is a UAA. In another preferred embodiment, UAA is an E1. In another preferred embodiment, the solid support is a microtiter plate. In another preferred embodiment, the solid support is a bead.

Figure 34:
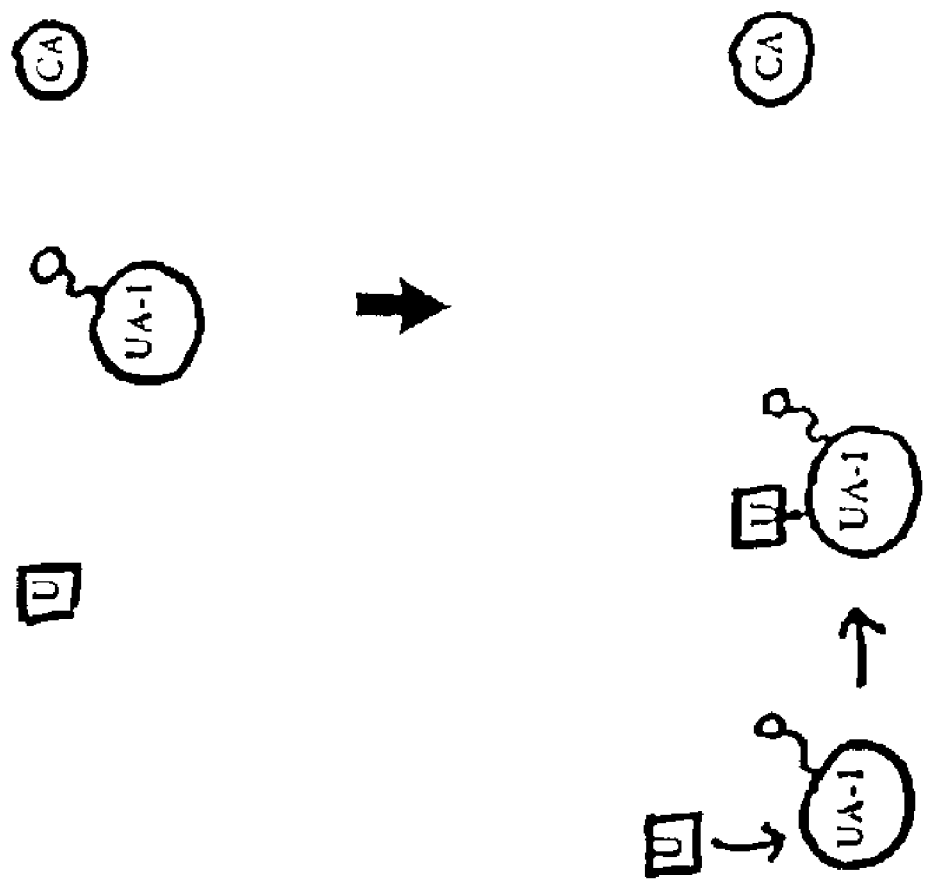

FIG. 34 schematically depicts a preferred embodiment for assaying for the attachment of ubiquitin moiety to a second ubiquitin agent (UA-2) that is attached to a solid suport) where the assay comprises:
1) combining a first ubiquitin agent that is UAA$_1$+UA-2 (attached to a solid support)+CA+U; and 2) assaying for the attachment of the ubiquitin moiety to UA-2. In another preferred embodiment, the solid support is a microtiter plate. In another preferred embodiment, the solid support is a bead. In a preferred embodiment, UA-2 comprises an Mdm2 protein.

FIG. 35 schematically depicts a preferred embodiment for assaying for the attachment of ubiquitin moiety to a first ubiquitin agent that is a ubiquitin ligating agent (ULA$_1$) that is attached to a solid support where the assay comprises:
1) combining a second ubiquitin agent that is a ubiquitin conjugating agent UCA$_2$ comprising a ubiquitin moiety+ULA$_1$ (attached to a solid support)+CA; and
2) assaying for the attachment of the ubiquitin moiety to ULA$_1$. In a preferred embodiment the ubiquitin ligating agent comprises an Mdm2.

FIG. 36 schematically depicts a preferred embodiment for assaying for the attachment of ubiquitin moiety to a first ubiquitin agent (UA-1) that comprises a label where the assay comprises:
1) combining a UA-1 (plus label)+CA+U; and
2) assaying for the attachment of the ubiquitin moiety to UA-1.

FIG. 37 schematically depicts a preferred embodiment for assaying for the attachment of ubiquitin moiety to a first ubiquitin agent that is a ubiquitin ligating agent (ULA$_1$) that comprises a label where the assay comprises:
1) combining a second ubiquitin agent that is a ubiquitin conjugating agent UCA$_2$ comprising a ubiquitin moiety+ULA$_1$ (plus label)+CA; and
2) assaying for the attachment of the ubiquitin moiety to ULA$_1$. In a preferred embodiment the ubiquitin ligating agent comprises an Mdm2 protein.

Figure 38:
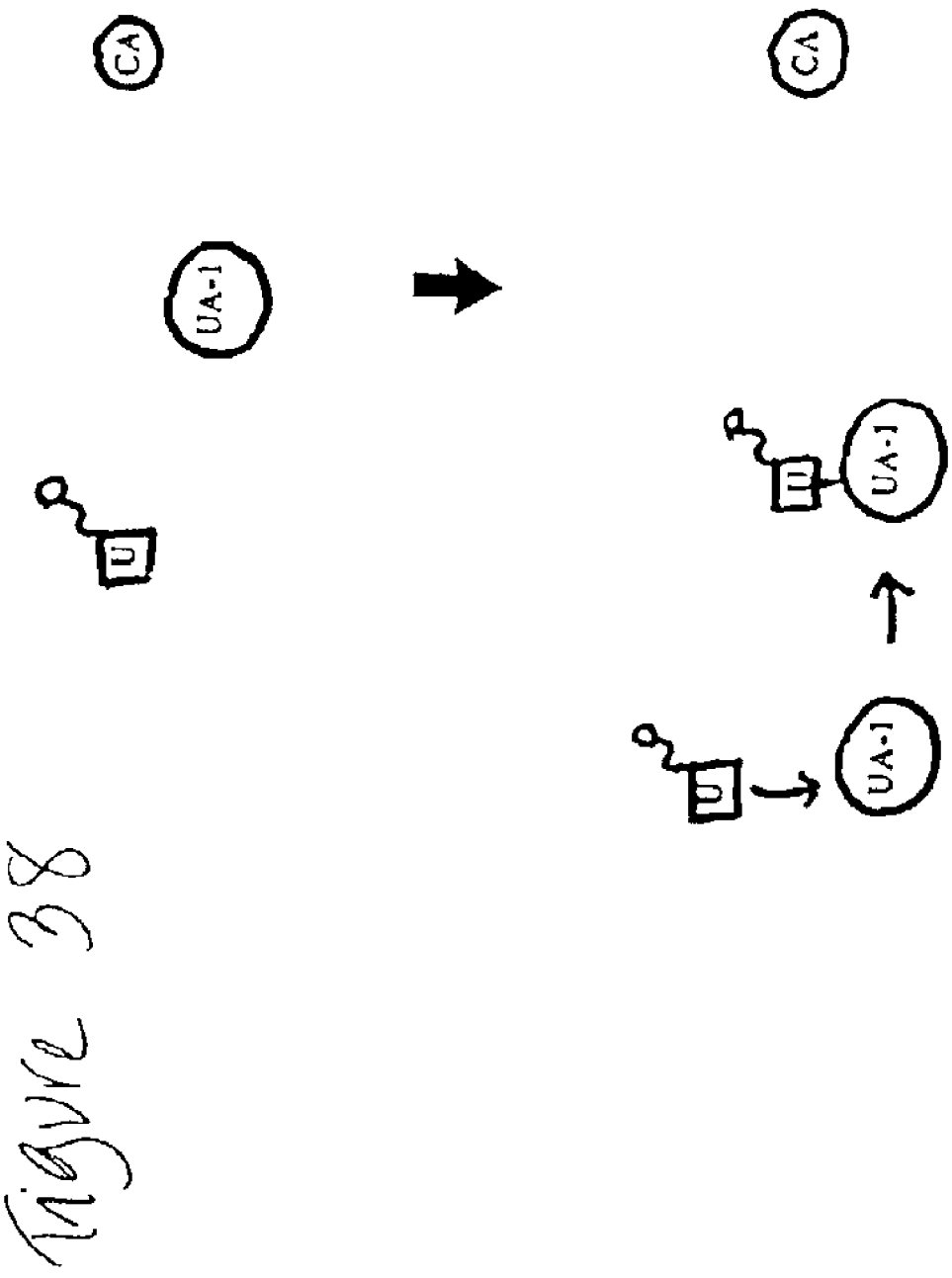

FIG. 38 schematically depicts a preferred embodiment for assaying for the attachment of ubiquitin moiety that comprises a label, to a first ubiquitin agent (UA-1) where the assay comprises:
1) combining a UA-1+CA+U (plus label); and
2) assaying for the attachment of the ubiquitin moiety to UA-1.

Figure 39:
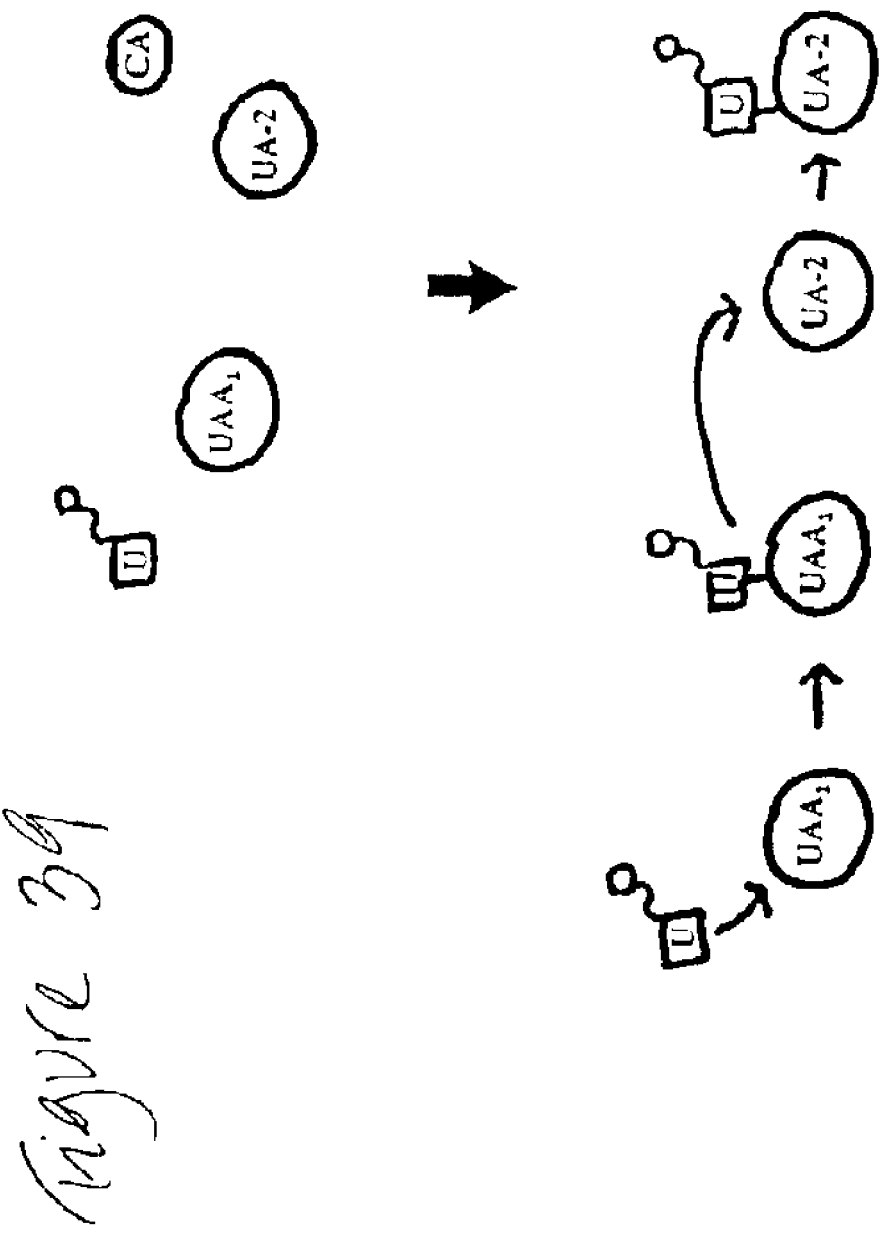

FIG. 39 schematically depicts a preferred embodiment for assaying for the attachment of ubiquitin moiety that comprises a label, to a second ubiquitin agent (UA-2) where the assay comprises:
1) combining a first ubiquitin agent that is UAA$_1$+UA-2+CA+U (plus label); and
2) assaying for the attachment of the ubiquitin moiety to UA-2.

FIG. 40 schematically depicts a preferred embodiment for assaying for the attachment of ubiquitin moiety that comprises a label, to a first ubiquitin agent that is a ubiquitin ligating agent (ULA$_1$) where the assay comprises:
1) combining a second ubiquitin agent that is a ubiquitin conjugating agent UCA$_2$ comprising a ubiquitin moiety (plus label)+ULA$_1$+CA; and
2) assaying for the attachment of the ubiquitin moiety to ULA$_1$. In a preferred embodiment the ubiquitin ligating agent comprises an Mdm2 protein.

FIG. 41 schematically depicts a preferred embodiment for assaying for the attachment of ubiquitin moiety to a first ubiquitin agent that is a ubiquitin ligating agent (ULA$_1$) which comprises a label where the assay comprises:
1) combining a second ubiquitin agent that is a ubiquitin conjugating agent UCA$_2$ comprising a ubiquitin moiety+ULA$_1$ (plus label)+CA; and
2) assaying for the attachment of the ubiquitin moiety to ULA$_1$. In a preferred embodiment the ubiquitin ligating agent comprises an Mdm2 protein.

Figure 42:
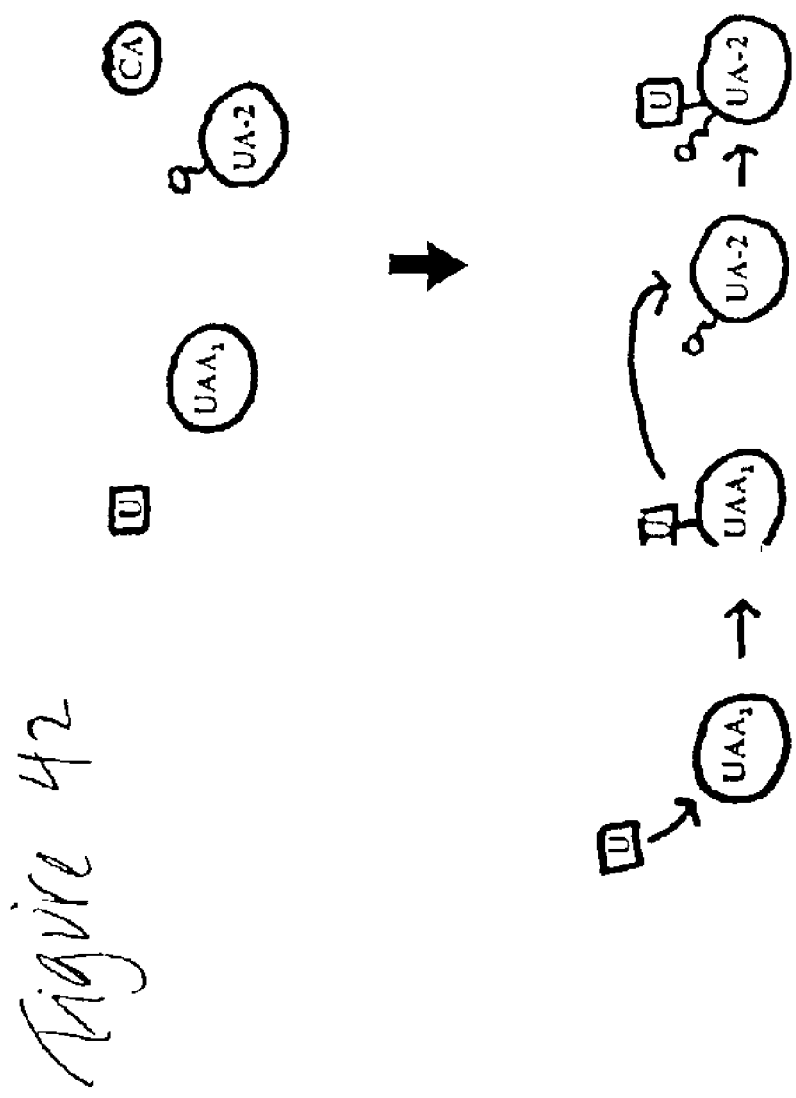

FIG. 42 schematically depicts a preferred embodiment for assaying for the attachment of ubiquitin moiety to a second ubiquitin agent (UA-2) that comprises a label where the assay comprises:
1) combining a first ubiquitin agent that is UAA$_1$+UA-2 (plus label)+CA+U; and
2) assaying for the attachment of the ubiquitin moiety to UA-2. In a preferred embodiment, UA-2 comprises an Mdm2 protein.

Figure 43:
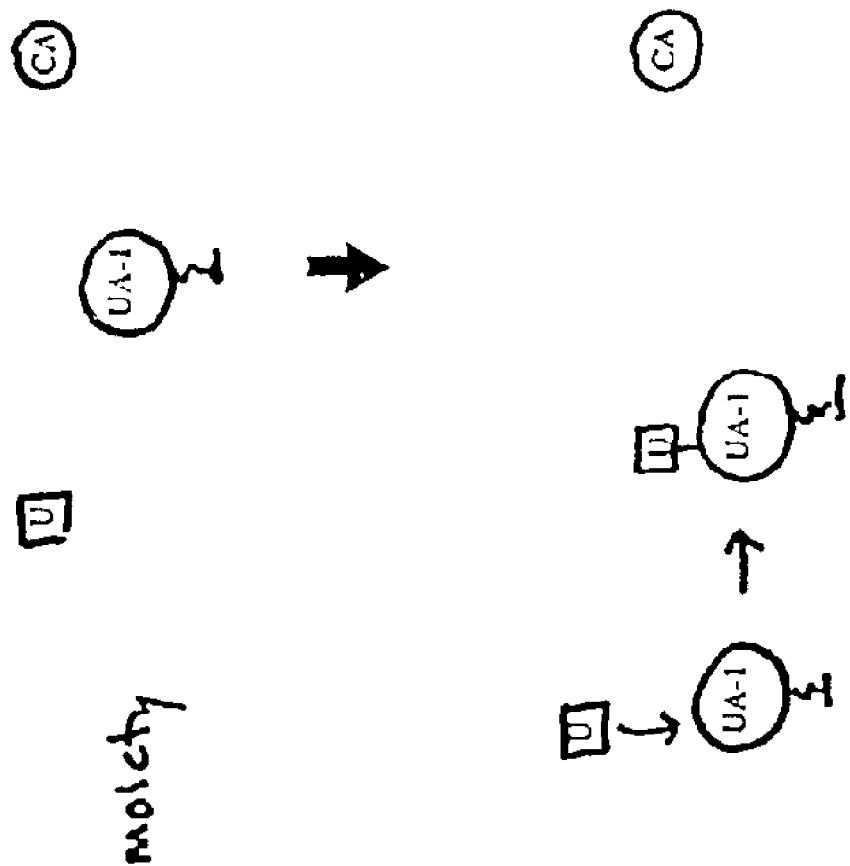

FIG. 43 schematically depicts a preferred embodiment for assaying for the attachment of ubiquitin moiety to a first ubiquitin agent (UA-1) that comprises an attachment tag (or attachment moiety) where the assay comprises:
1) combining a UA-1 (plus attachment tag)+CA+U; and
2) assaying for the attachment of the ubiquitin moiety to UA-1.

Figure 44:
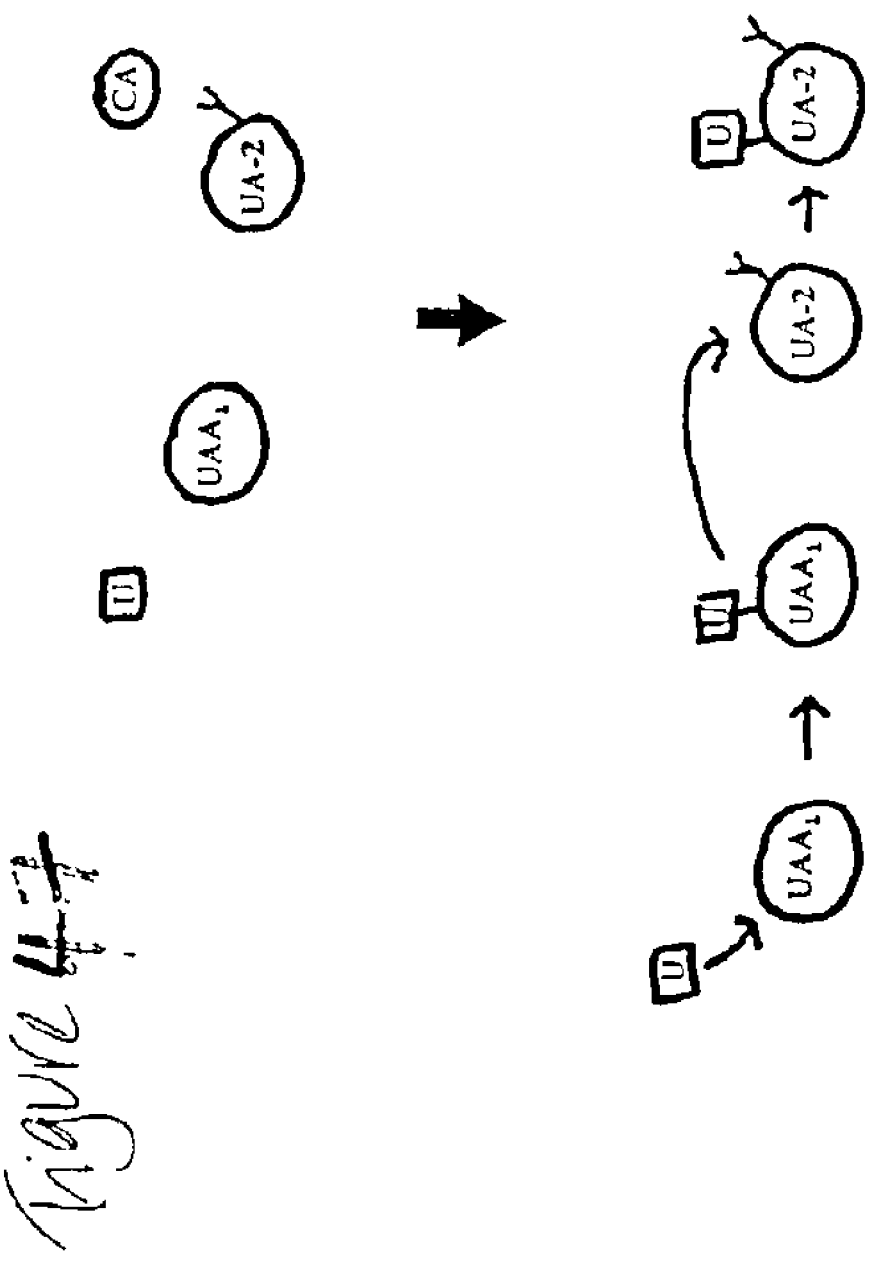

FIG. 44 schematically depicts a preferred embodiment for assaying for the attachment of ubiquitin moiety to a first ubiquitin agent that is a ubiquitin ligating agent (ULA$_1$) that comprises an attachment tag (or attachment moiety) where the assay comprises:
1) combining a second ubiquitin agent that is a ubiquitin conjugating agent UCA$_2$ comprising a ubiquitin moiety+ULA$_1$ (plus attachment tag)+CA; and
2) assaying for the attachment of the ubiquitin moiety to ULA$_1$. In a preferred embodiment the ubiquitin ligating agent comprises an Mdm2 protein.

Figure 45:
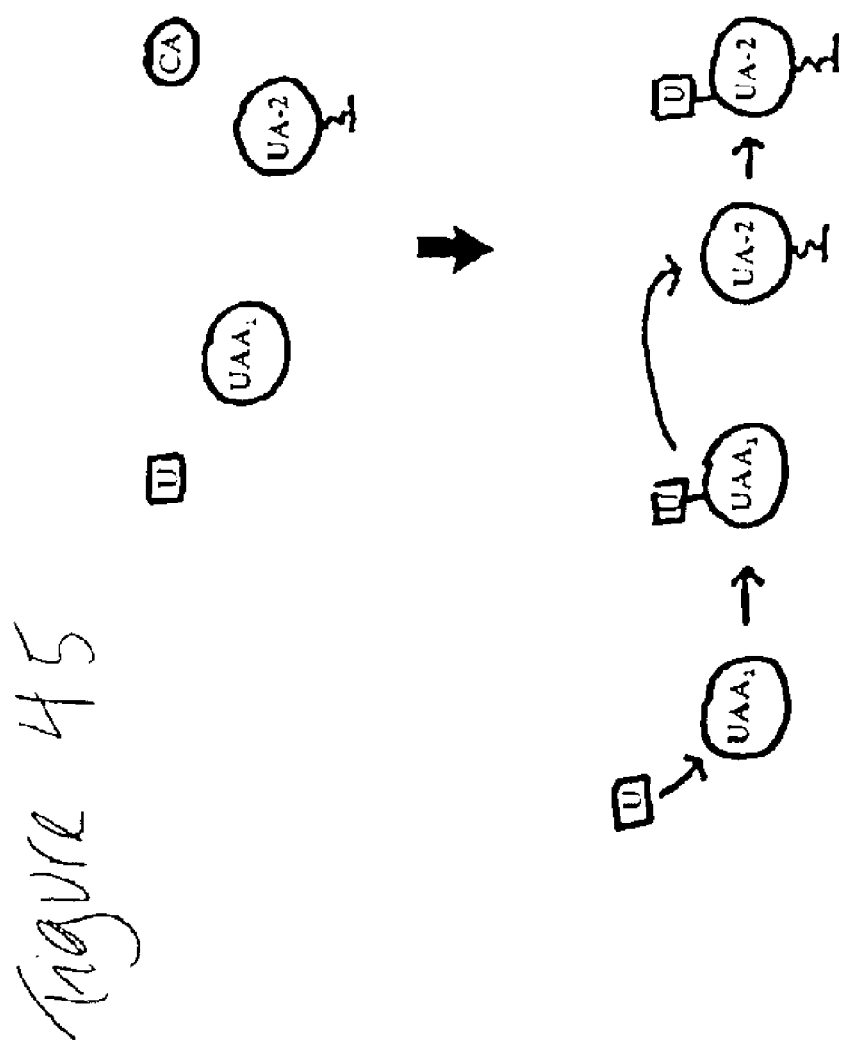

FIG. 45 schematically depicts a preferred embodiment for assaying for the attachment of ubiquitin moiety to a second ubiquitin agent (UA-2) that comprises an attachment tag (or attachment moiety) where the assay comprises:
1) combining a first ubiquitin agent that is UAA$_1$+UA-2 (plus attachment tag)+CA+U; and
2) assaying for the attachment of the ubiquitin moiety to UA-2.

Figure 46:
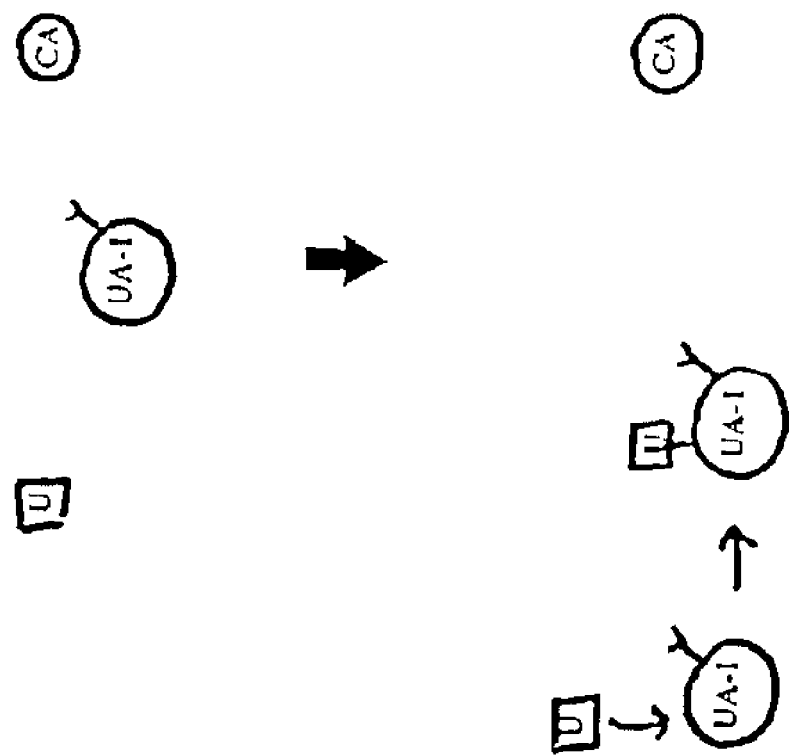

FIG. 46 schematically depicts a preferred embodiment for assaying for the attachment of ubiquitin moiety to a first ubiquitin agent (UA-1) that comprises an epitope tag (or epitope label) where the assay comprises:
1) combining a UA-1 (plus epitope tag)+CA+U; and
2) assaying for the attachment of the ubiquitin moiety to UA-1.

FIG. 47 schematically depicts a preferred embodiment for assaying for the attachment of ubiquitin moiety to a second ubiquitin agent (UA-2) that comprises an epitope tag (or epitope label) where the assay comprises:
1) combining a first ubiquitin agent that is UAA$_1$+UA-2 (plus epitope tag)+CA+U; and
2) assaying for the attachment of the ubiquitin moiety to UA-2.

Figure 48:
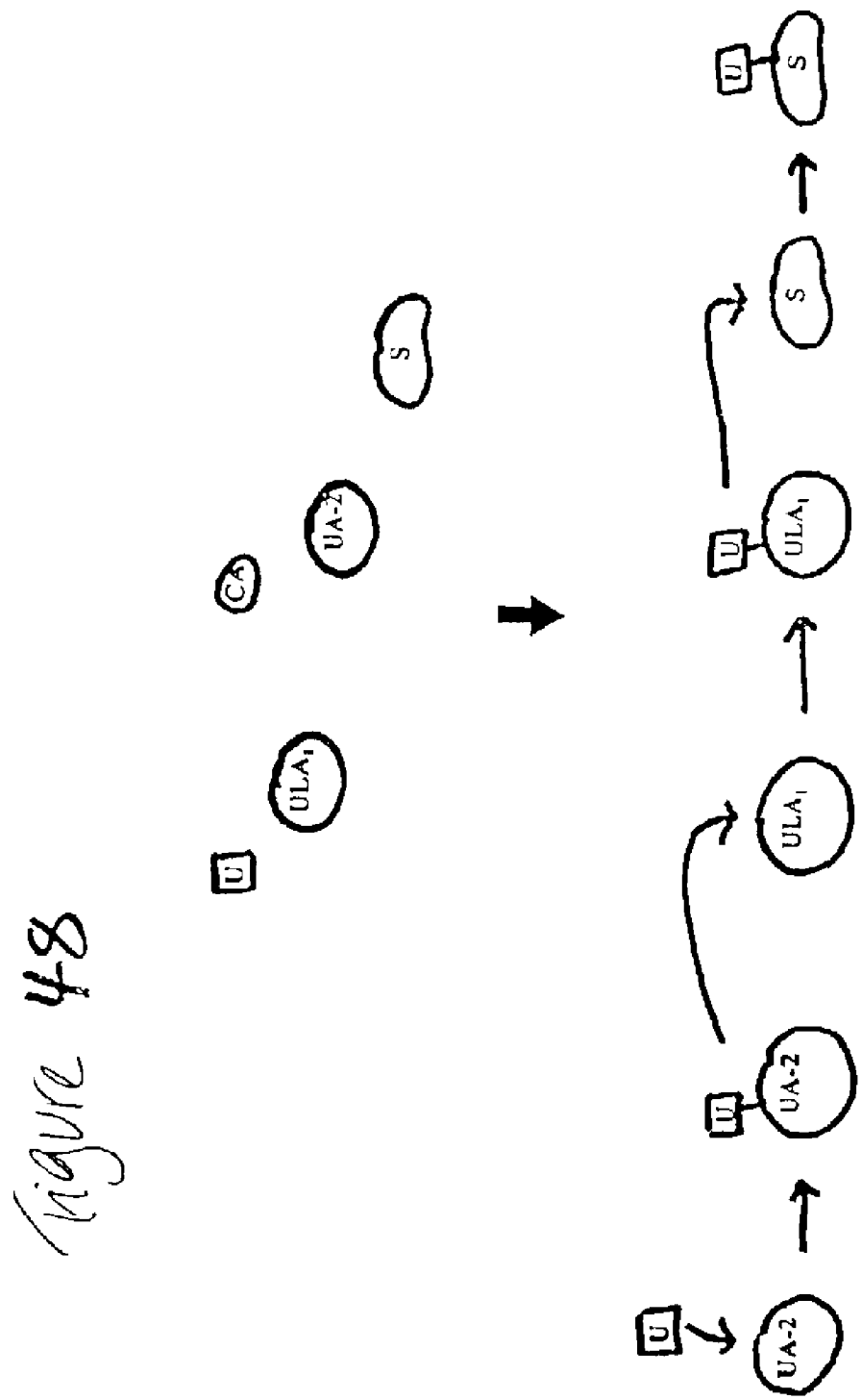

FIG. 48 schematically depicts a preferred embodiment for assaying for the attachment of ubiquitin moiety to a substrate molecule (s) where the assay comprises:
1) combining a first ubiquitin agent that is a ubiquitin ligating agent ULA$_1$+a second ubiquitin agent+substrate molecule+CA+U; and
2) assaying for the attachment of the ubiquitin moiety to the substrate molecule. In a preferred embodiment the ubiquitin ligating agent comprises an Mdm2 protein and the substrate molecule comprises p53.

Figure 49:
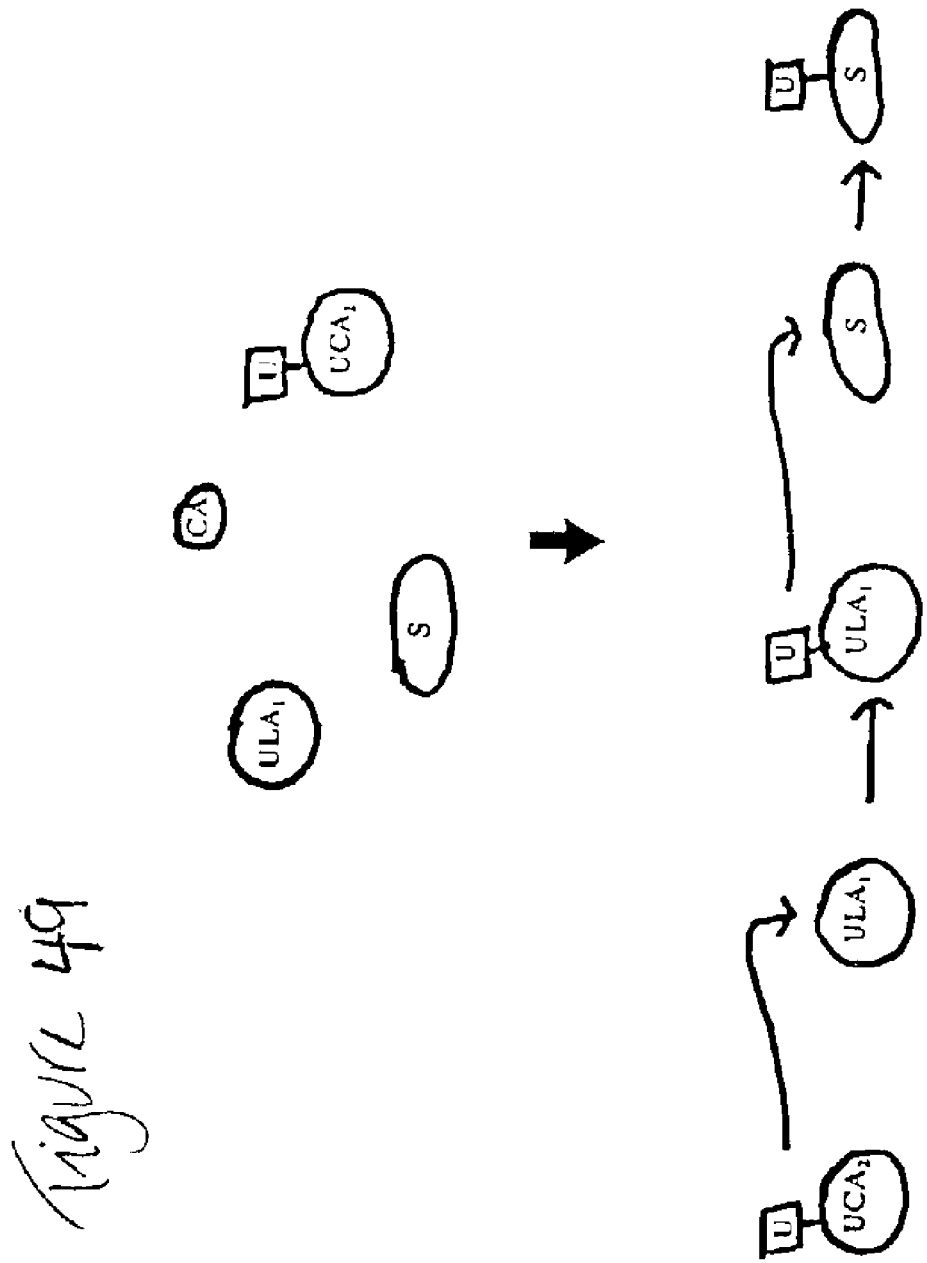

FIG. 49 schematically depicts a preferred embodiment for assaying for the attachment of ubiquitin moiety to a substrate molecule (s) where the assay comprises:
1) combining a first ubiquitin agent that is a ubiquitin ligating agent ULA$_1$+a second ubiquitin agent that is a ubiquitin conjugating agent and comprising a ubiquitin moiety+substrate molecule+CA; and 2) assaying for the attachment of the ubiquitin moiety to the substrate molecule. In a preferred embodiment the ubiquitin ligating agent comprises an Mdm2 protein and the substrate molecule comprises p53.

FIG. 50 schematically depicts a preferred embodiment for assaying for the attachment of ubiquitin moiety to a substrate molecule (s) where the assay comprises:
1) combining a first ubiquitin agent that is a ubiquitin ligating agent $ULA_1$+a second ubiquitin agent+a third ubiquitin agent that is a ubiquitin activating agent+a ubiquitin moiety comprising a first FRET tag+substrate molecule comprising a second FRET tag+CA; and
2) assaying for the attachment of the ubiquitin moiety to the substrate molecule. In a preferred embodiment the ubiquitin ligating agent comprises an Mdm2 protein and the substrate molecule comprises p53.

FIG. 51 depicts the amino acid sequence (FIG. 51A) and the nucleic acid sequence (FIG. 51B)) of an E2 in a preferred embodiment.

FIG. 52 depicts the amino acid sequence (FIG. 52A) and the nucleic acid sequence (FIG. 52B1 and FIG. 52B2)) of an E2 in a preferred embodiment.

FIG. 53 depicts the amino acid sequence (FIG. 53A) and the nuclei c acid sequence (FIG. 53B1 and FIG. 53B2) of an E2 in a preferred embodiment.

FIG. 54 depicts the amino acid sequence (FIG. 54A) and the nucleic acid sequence (FIG. 54B) of an E2 in a preferred embodiment.

FIG. 55 depicts the amino acid sequence (FIG. 55A) and the nucleic acid sequence (FIG. 55B) of an E2 in a preferred embodiment.

DETAILED DESCRIPTION OF THE INVENTION

The present invention provides methods and compositions for assaying for ubiquitin agents that are enzymatic components of ubiquitin-mediated proteolysis. More particularly, the present invention provides methods and compositions for assaying for an agent that modulates the activity of a ubiquitin agent that is an enzymatic component of ubiquitin-mediated proteolysis. Specifically, the methods of the present invention are directed to identifying ubiquitin agents such as ubiquitin activating agents, ubiquitin conjugating agents, and ubiquitin ligating agents; and to identifying agents that modulate the activity of these ubiquitin agents.

The advantages of the present invention include providing methods for assaying for the activity of ubiquitin agents in one reaction vessel thus obviating the need for subsequent steps, for example, for separating and purifying the products of the reaction. Consequently, this approach allows multiwell array analysis and high throughput screening techniques for agents that modulate the activity of ubiquitin agents. In addition, the present invention provides methods that allow the analysis of many different combinations of ubiquitin agents, without requiring prior identification of specific target proteins. In particular, the present invention provides methods that allow the analysis of different combinations of ubiquitin agents in the absence of a target protein. Alternatively, the present invention provides methods that allow the analysis of combinations of ubiquitin agents in the presence of a target protein.

In the methods of the present invention the ubiquitin agents are combined in different combinations with a ubiquitin moiety to assay for the attachment of the ubiquitin moiety, or the modulation of this attachment, to at least one of the following substrate molecules: a ubiquitin agent, a target protein, or a mono- or poly-ubiquitin moiety which is preferably attached to a ubiquitin agent or target protein. For example, the invention provides the following combination of ubiquitin agents, plus or minus a target protein, for use in methods of:

1) assaying for the attachment of a ubiquitin moiety to a ubiquitin activating agent by combining a ubiquitin activating agent and a ubiquitin moiety; or
2) assaying for the attachment of a ubiquitin moiety to a ubiquitin conjugating agent by combining a ubiquitin activating agent, ubiquitin conjugating agent, and ubiquitin moiety; or
3) assaying for the attachment of a ubiquitin moiety to a ubiquitin conjugating agent by combining a ubiquitin activating agent comprising a ubiquitin moiety and a ubiquitin conjugating agent; or
4) assaying for the attachment of a ubiquitin moiety to a ubiquitin ligating agent by combining a ubiquitin conjugating agent comprising a ubiquitin moiety and a ubiquitin ligating agent; or
5) assaying for the attachment of a ubiquitin moiety to a ubiquitin ligating agent by combining a ubiquitin activating agent, ubiquitin conjugating agent, ubiquitin ligating agent, and ubiquitin moiety; or
6) assaying for the attachment of a ubiquitin moiety to a ubiquitin ligating agent by combining a ubiquitin activating agent comprising a ubiquitin moiety, a ubiquitin conjugating agent, and ubiquitin ligating agent; or
7) assaying for the attachment of a ubiquitin moiety to a target protein by combining a ubiquitin activating agent, a ubiquitin conjugating agent, a ubiquitin ligating agent, a ubiquitin moiety, and a target protein; or
8) assaying for the attachment of a ubiquitin moiety to a target protein by combining a ubiquitin activating agent comprising a ubiquitin moiety, a ubiquitin conjugating agent, ubiquitin ligating agent, and target protein; or
9) assaying for the attachment of a ubiquitin moiety to a target molecule by combining a ubiquitin activating agent comprising a ubiquitin moiety, a ubiquitin conjugating agent, and a target protein.

In particular, in the methods of the present invention, to assay for a candidate agent that modulates the attachment of a ubiquitin moiety to a substrate molecule of interest, a candidate agent is included in the above examples of combinations.

The invention provides a variety of approaches using above the combinations of ubiquitin agents to assay for the attachment of a ubiquitin moiety to a substrate molecule of interest, or to assay for an agent that modulates the attachment of a ubiquitin moiety to a substrate molecule of interest. Examples of the approaches are as follows:

1) the components of the assay are combined in solution phase, and then assayed for the attachment of ubiquitin moiety to the substrate molecule of interest; or
2) the components of the assay are combined in solid phase by providing the substrate molecule of interest on a solid support, and then assayed for the attachment of ubiquitin moiety to the substrate molecule of interest; or
3) the components of the assay are combined in solution phase, then the substrate molecule of interest is attached to a solid substrate, and then assayed for the attachment of ubiquitin moiety to the substrate molecule of interest; or
4) the components of the assay are combined in solution, then the substrate molecule of interest that is attached to ubiquitin moiety is purified, the purified product is then attached to a solid substrate, and assayed for the attachment of ubiquitin moiety to the substrate molecule.

Examples of ubiquitin agents are ubiquitin activating agents, ubiquitin conjugating agents, and ubiquitin ligating agents. In preferred embodiments, the ubiquitin activating agent is preferably an E1 or a variant thereof; the ubiquitin conjugating agent is preferably an E2 or a variant thereof; and the ubiquitin ligating agent is preferably an E3 or variant there of. In a preferred embodiment, the E3 is Mdm2. In another preferred embodiment, the Mdm2 is a fusion protein, and more preferably an Mdm2-GST fusion protein. Thus, the present invention provides methods of assaying for agents that modulate ubiquitin activating activity, ubiquitin conjugating activity, and ubiquitin ligating activity. More particularly, the present invention provides methods of assaying for agents that modulate the attachment of a ubiquitin moiety to a ubiquitin agent, target protein, or mono- or poly-ubiquitin moiety preferably attached to a ubiquitin agent or target protein.

In general, the methods involve combining a ubiquitin moiety and one or more ubiquitin agents in the presence of or in the absence of a target protein and measuring the amount of ubiquitin moiety attached to at least one of the following substrate molecules: a ubiquitin agent; a target protein; or a mono- or poly-ubiquitin moiety which is preferably attached to a ubiquitin agent or target protein. As used herein, "substrate molecule" or "target substrate" and grammatical equivalents thereof means a molecule, preferably a protein, to which a ubiquitin moiety is bound or attached through the activity of a ubiquitin agent or by the process of ubiquitination. As used herein, "the substrate molecule of interest" is the ubiquitin agent, target protein, or ubiquitin moiety to which the attachment of a ubiquitin moiety is being assayed for in the methods of the present invention. As used herein with reference to the activity of ubiquitin agents, "attachment" refers to the transfer, binding, ligation, and/or ubiquitination of a mono- or poly-ubiquitin ubiquitin moiety to a substrate molecule. Thus, "ubiquitination" and grammatical equivalents thereof means the attachment, or transfer, binding, and/or ligation of ubiquitin moiety to a substrate molecule; and "ubiquitination reaction" and grammatical equivlents thereof refer to the combining of components under conditions that permit ubiquitination (i.e., the attachment or transfer, binding, and/or ligation of ubiquitin moiety to a substrate molecule).

In some preferred embodiments, the ubiquitin agent comprises a ubiquitin moiety. As used herein with reference to a ubiquitin agent, the phrase "comprising a ubiquitin moiety" or grammatical equivalents thereof refers to the pre-loading, pre-conjugation, or pre-attachment of a ubiquitin moiety to a ubiquitin agent (forming a "pre-conjugated ubiquitin agent" or "pre-loaded ubiquitin agent") such that the attachment of a ubiquitin moiety to a substrate molecule of interest does not require combining all three ubiquitin agents (i.e., an ubiquitin activating agent, ubiquitin conjugating agent, and ubiquitin ligating agent) and/or combining ubiquitin moiety that is not pre-conjugated. For example in the case of a ubiquitin activating agent comprising a ubiquitin moiety, the attachment of ubiquitin moiety to a ubiquitin conjugating agent can be performed in the absence of ubiquitin moiety that is not pre-conjugated. For example, in the case of a ubiquitin conjugating agent comprising a ubiquitin moiety, the attachment of ubiquitin moiety to a ubiquitin ligating agent can be performed in the absence of a ubiquitin activating agent and ubiquitin moiety that is not pre-conjugated. Also, for example, in the case of a ubiquitin ligating agent comprising a ubiquitin moiety, the attachment of ubiquitin moiety to a target molecule can be performed in the absence of a ubiquitin activating agent, ubiquitin conjugating agent, and ubiquitin moiety that is not pre-conjugated. A pre-conjugated ubiquitin agent suitable for use in the methods and compositions of the present invention can be prepared using methods known in the art. In a preferred embodiment, pre-conjugated ubiquitin agents are prepared according to Zhihong et al. (2001) J.Biol.Chem. 276:31,357–31,367.

By "target protein" herein is meant a protein other than a ubiquitin moiety to which a ubiquitin moiety is bound or attached through the activity of a ubiquitin agent or by the process of ubiquitination. In preferred embodiments, the target protein is a mammalian target protein, and more preferably a human target protein. In a preferred embodiment, the target protein is p53.

In the following preferred embodiments at least one ubiquitin agent is combined with a ubiquitin moiety in the absence of a target protein.

In a preferred embodiment, the invention provides a method of assaying for an agent that modulates the attachment of a ubiquitin moiety to at least one ubiquitin agent involving the steps of: a) combining a first ubiquitin agent, a candidate agent, and a ubiquitin moiety; and b) assaying for the attachment of the ubiquitin moiety to the first agent. In one preferred embodiment the first ubiquitin agent is an ubiquitin activating agent, and preferably an E1. In another embodiment, the method further comprises including a second ubiquitin agent in the combining step, where the first agent is preferably a ubiquitin conjugating agent and more preferably and E2; and the second agent is preferably a ubiquitin activating agent and more preferably an E1. In another embodiment, the ubiquitin conjugating agent is preferably an E2 and the ubiquitin activating agent is preferably an E1 comprising the ubiquitin moiety.

In another embodiment, the first agent is a preferably a ubiquitin ligating agent and more preferably an E3; and the second agent is preferably a ubiquitin conjugating agent comprising the ubiquitin moiety and more preferably an E2 comprising a ubiquitin moiety.

In another embodiment, the method further comprises a third ubiquitin agent in the combining step. In one embodiment, the third agent is preferably a ubiquitin ligating agent and more preferably an E2.

In the methods where the assaying concerns the attachment of the ubiquitin moiety to the first ubiquitin agent, the following preferred embodiments are provided. In one embodiment, the first ubiquitin agent preferably comprises a tag and more preferably an epitope tag or a label. In another embodiment, the first ubiquitin agent preferably comprises an attachment tag. In another embodiment, the first ubiquitin agent is preferably attached to a solid support and more preferably is attached to a microtiter plate or a bead.

In the methods where the assaying concerns the attachment of the ubiquitin moiety to the second ubiquitin agent, the following preferred embodiments are provided. In one embodiment, the second ubiquitin agent preferably comprises a tag and more preferably an epitope tag or a label. In another embodiment, the second ubiquitin agent preferably comprises an attachment tag. In another embodiment, the second ubiquitin agent is preferably attached to a solid support and more preferably is attached to a microtiter plate or a bead.

In a preferred embodiment, the invention provides a method of assaying for a candidate agent that modulates the attachment of a ubiquitin moiety to an MdM2 protein involving the steps of: a) combining a first ubiquitin agent comprising at least one ubiquitin moiety, an MdM2 protein, and a candidate agent; and b) assaying for the attachment of the ubiquitin moiety to the MdM2 protein. In an additional embodiment, the first ubiquitin agent is preferably a ubiquitin conjugating agent.

In another preferred embodiment, the method further comprises combining a ubiquitin activating agent comprising the ubiquitin moiety, thereby forming the ubiquitin conjugating agent comprising the ubiquitin moiety, in step a).

In another preferred embodiment, the method further comprises combining a ubiquitin activating agent and the ubiquitin moiety, thereby forming the ubiquitin conjugating agent comprising the ubiquitin moiety.

In another preferred embodiment, the invention provides a method of assaying for a candidate agent that modulates the attachment of a ubiquitin moiety to an MdM2 protein involving the steps of: a) combining a ubiquitin activating agent, a ubiquitin conjugating agent, an MdM2 protein, a candidate agent, and a ubiquitin moiety; and b) assaying for the attachment of the ubiquitin moiety to the MdM2 protein.

Alternatively, the invention provides assays including a target protein. In the following preferred embodiments a target protein is combined with ubiquitin moiety and at least one ubiquitin agent.

In another preferred embodiment, the invention provides a method of assaying for an agent that modulates the attachment of a ubiquitin moiety to at least one ubiquitin agent involving the steps of: a) combining a first ubiquitin agent comprising a ubiquitin ligating agent; a second ubiquitin agent, a candidate agent, a ubiquitin moiety, and a target protein; and b) assaying for the attachment of the ubiquitin moiety to the first agent. In an additional embodiment, the second agent is a ubiquitin conjugating agent comprising the ubiquitin moiety.

In another preferred embodiment, the method further comprises a third ubiquitin agent in the combining step, wherein the third agent is a ubiquitin activating agent; wherein the substrate and the ubiquitin moiety comprise different fluorescent labels, and wherein the labels form a fluorescence resonance energy transfer (FRET) pair.

In another preferred embodiment, the invention provides a method of assaying for a candidate agent that modulates the attachment of a ubiquitin moiety to a p53 protein involving the steps of: a) combining a conjugating agent comprising at least one ubiquitin moiety, an Mdm2 protein, a p53 protein, and a candidate agent; and b) assaying for the attachment of the ubiquitin moiety to the p53 protein.

In an additional preferred embodiment, the method further comprises combining a ubiquitin conjugating agent and the ubiquitin moiety, thereby forming the ubiquitin conjugating agent comprising the ubiquitin moiety.

In an additional preferred embodiment, the method further comprises combining a ubiquitin activating agent comprising the ubiquitin moiety, thereby forming the ubiquitin conjugating agent comprising the ubiquitin moiety, in step a).

In an additional preferred embodiment, the method further comprises combining a ubiquitin activating agent and the ubiquitin moiety, thereby forming the ubiquitin conjugating agent comprising the ubiquitin moiety.

In another preferred embodiment, the invention provides a method of assaying for a candidate agent that modulates the attachment of a ubiquitin moiety to a p53 protein involving the steps of: a) combining a ubiquitin activating agent, a ubiquitin conjugating agent, an MdM2 protein, a p53 protein, a candidate agent, and a ubiquitin moiety; and b) assaying for the attachment of the ubiquitin moiety to the p53 protein.

In another preferred embodiment, the invention provides a method of assaying for a candidate agent that modulates the attachment of a second ubiquitin moiety to a p53 protein involving the steps of: a) combining a ubiquitin activating agent, a ubiquitin conjugating agent, an MdM2 protein, a p53 protein comprising a first ubiquitin moiety, wherein the first ubiquitin moiety is labeled with a first FRET label, a candidate agent, and a second ubiquitin moiety labeled with a second FRET label; and b) assaying for the attachment of the second ubiquitin moiety to the p53 protein by detecting a FRET reaction.

In another preferred embodiment, the invention provides a method of assaying for a candidate agent that modulates the attachment of a first ubiquitin moiety to a p53 protein involving the steps of: a) combining a ubiquitin conjugating agent comprising a first ubiquitin moiety labeled with a first FRET, an MdM2 protein, a p53 protein comprising a second ubiquitin moiety, wherein the first ubiquitin moiety is labeled with a second FRET label, and a candidate agent; and b) assaying for the attachment of the first ubiquitin moiety to the p53 protein by detecting a FRET reaction.

In another preferred embodiment, the invention provides a method of assaying for a candidate agent that modulates the attachment of a first ubiquitin moiety to a p53 protein involving the steps of: a) combining a ubiquitin activating agent comprising a first ubiquitin moiety labeled with a first FRET, a ubiquitin conjugating agent, an MdM2 protein, a p53 protein comprising a second ubiquitin moiety, wherein the first ubiquitin moiety is labeled with a second FRET label, and a candidate agent; and b) assaying for the attachment of the first ubiquitin moiety to the p53 protein by detecting a FRET reaction.

In a preferred embodiment, the substrate molecule of interest is attached to the surface of a reaction vessel, such as the well of a multi-well plate. This embodiment facilitates the separation of the ubiquitin moiety that is attached to the substrate molecule of interest from the unattached or free ubiquitin moiety. Means for attaching ubiquitin agents or target proteins to the surface of a reaction vessel are described below. The present methods permits the entire assay to occur in one vessel, making the assay useful for high-throughput screening applications.

In a preferred embodiment, the ubiquitin moiety is labeled, either directly or indirectly, as further described below, and the amount of label is measured and indicative of the amount of attachment of ubiquitin moiety to a substrate molecule of interest. Thus, the invention provides methods that permit for easy and rapid detection and measurement of the activity of ubiquitin agents, making the assay useful for high-throughput screening applications. In one preferred embodiment, the signal of the label varies with the extent of the attachment of ubiquitin moiety to the substrate molecule of interest, such as in the FRET system described below. One of ordinary skill in the art will recognize the applicability of the present invention to screening for agents which modulate ubiquitin ubiquitination.

As used herein, 'ubiquitin moiety' refers to a polypeptide which is transferred or attached to another polypeptide by a ubiquitin agent. The ubiquitin moiety can comprise a ubiquitin from any species of organism, preferably a eukaryotic species. In preferred embodiments the ubiquitin moiety comprises is a mammlian ubiquitin, and more preferably a human ubiquitin. In a preferred embodiment, the ubiquitin moiety comprises a 76 amino acid human ubiquitin. In a preferred embodiment, the ubiquitin moiety comprises the amino acid sequence depicted in FIG. 15A. Other embodiments utilize variants of ubiquitin, as further described below.

As used herein, "poly-ubiquitin moiety" refers to a chain of ubiquitin moieties comprising more than one ubiquitin moiety. As used herein, "mono-ubiquitin moiety" refers to a single ubiquitin moiety. In the methods of the present invention, a mono- or poly-ubiquitin moiety can serve as a substrate molecule for the transfer or attachment of ubiquitin moiety (which can itself be a mono- or poly-ubiquitin moiety).

In a preferred embodiment, when ubiquitin moiety is attached to a target protein, that protein is targeted for degradation by the 26S proteasome.

As used herein, "ubiquitin moiety" encompasses naturally occurring alleles and man-made variants of such a 76 amino acid polypeptide. In a preferred embodiment, the ubiquitin moiety comprises an amino acid sequence or nucleic acid sequence corresponding to a sequence of GENBANK accession number PO2248, incorporated herein by reference. In other preferred embodiments, the ubiquitin moiety comprises an amino acid sequence or nucleic acid sequence of a sequence corresponding to one of the following GENBANK accession numbers: NM_006156 (NEDD8); NM_003352 (SUMO-1, aka, UBL1); XM_048691 (SUMO-1, aka, UBL1); NM_006936 (smt3a); XM_009805 (smt3a); XM_095400 (smt3b); NM_006937 (smt3b); XM_041583 (smt3b); NM_015783 (ISG15); or NM_005101 (ISG15), each incorporated herein by reference.

GENBANK accession numbers and their corresponding amino acid sequences or nucleic acid sequences are found in the Genbank data base. Sequences corresponding to GenBank accession numbers cited herein are incorporated herein by reference. GenBank is known in the art, see, e.g., Benson, D A, et al., Nucleic Acids Research 26:1–7 (1998) and http://www.ncbi.nlm.nih.gov/. Preferably, the ubiquitin moiety has the amino acid sequence depicted in FIG. 15A. In a preferred embodiment, variants of ubiquitin moiety have an overall amino acid sequence identity of preferably greater than about 75%, more preferably greater than about 80%, even more preferably greater than about 85% and most preferably greater than 90% of the amino acid sequence depicted in FIG. 15A. In some embodiments the sequence identity will be as high as about 93 to 95 or 98%.

In another preferred embodiment, a ubiquitin moiety protein has an overall sequence similarity with the amino acid sequence depicted in FIG. 15A of greater than about 80%, more preferably greater than about 85%, even more preferably greater than about 90% and most preferably greater than 93%. In some embodiments the sequence identity will be as high as about 95 to 98 or 99%.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., *Methods in Enzymology*, 266: 460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer amino acids than the amino acid sequence depictd in FIG. 15A, it is understood that in one embodiment, the percentage of sequence identity will be determined based on the number of identical amino acids in relation to the total number of amino acids. Thus, for example, sequence identity of sequences shorter than that of the sequence depicted in FIG. 15A, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Ubiquitin moieties of the present invention are polypeptides that may be shorter or longer than the amino acid sequence depicted in FIG. 15A. Thus, in a preferred embodiment, included within the definition of ubiquitin moiety are portions or fragments of the amino acid sequence depicted in FIG. 15A. In one embodiment herein, fragments of ubiquitin moiety are considered ubiquitin moieties if they are attached to another polypeptide by a ubiquitin agent.

In addition, as is more fully outlined below, ubiquitin moieties of the present invention are polypeptides that can be made longer than the amino acid sequence depicted in FIG. 15A; for example, by the addition of tags, the addition of other fusion sequences, or the elucidation of additional coding and non-coding sequences. As described below, the fusion of a ubiquitin moiety to a fluorescent peptide, such as Green Fluorescent Peptide (GFP), is particularly preferred.

The ubiquitin moiety, as well as other proteins of the present invention, are preferably recombinant proteins. A "recombinant protein" is a protein made using recombinant techniques, i.e. through the expression of a recombinant nucleic acid as described below. In a preferred embodiment, the ubiquitin moiety of the invention is made through the expression of a nucleic acid sequence corresponding to GENBANK accession number M26880 or AB003730, or a fragment thereof. In a most preferred embodiment, the nucleic acid encodes the amino acid sequence depicted in FIG. 15A. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in FIGS. 1 and 3 also include the complement of the sequence. By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

The terms "polypeptide" and "protein" may be used interchangeably throughout this application and mean at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

In one embodiment, the present invention provides compositions containing protein variants, for example ubiquitin moiety, E1, E2 and/or E3 variants. These variants fall into one or more of three classes: substitutional, insertional or deletional variants. These variants ordinarily are prepared by site specific mutagenesis of nucleotides in the DNA encoding a protein of the present compositions, using cassette or PCR mutagenesis or other techniques well known in the art, to produce DNA encoding the variant, and thereafter expressing the DNA in recombinant cell culture as outlined above. However, variant protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variants screened for the optimal desired activity. Techniques for making substitution mutations at predetermined sites in DNA having a known sequence are well known, for example, M13 primer mutagenesis and PCR mutagenesis. Rapid production of many variants may be done using techniques such as the method of gene shuffling, whereby fragments of similar variants of a nucleotide sequence are allowed to recombine to produce new variant combinations. Examples of such techniques are found in U.S. Pat. Nos. 5,605,703; 5,811,238; 5,873,458; 5,830,696; 5,939, 250; 5,763,239; 5,965,408; and 5,945,325, each of which is incorporated by reference herein in its entirety. Screening of the mutants is performed using the activity assays of the present invention.

Amino acid substitutions are typically of single residue s; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the protein are desired, substitutions of an original residue are generally made in accordance with exemplary substitutions listed below.

| Original Residue | Exemplary Substitutions |
| --- | --- |
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in the above list. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the proteins as needed. Alternatively, the variant may be designed such that the biological activity of the protein is altered. For example, glycosylation sites may be altered or removed.

Covalent modifications of polypeptides are included within the scope of this invention. One type of covalent modification includes reacting targeted amino acid residues of a polypeptide with an organic derivatizing agent that is capable of reacting with selected side chains or the N- or C-terminal residues of a polypeptide. Derivatization with bifunctional agents is useful, for instance, for crosslinking a protein to a water-insoluble support matrix or surface for use in the method for screening assays, as is more fully described be low. Commonly used crosslinking agents include, e.g., 1,1-bis(diazoacetyl)-2-phenylethane, glutaraldehyde, -hydroxy-succinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the—amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of a polypeptide included within the scope of this invention comprises altering the native glycosylation pattern of the polypeptide. "Altering the native glycosylation pattern" is intended for purposes herein to mean deleting one or more carbohydrate moieties found in native sequence polypeptide, and/or adding one or more glycosylation sites that are not present in the native sequence polypeptide.

Addition of glycosylation sites to polypeptides may be accomplished by altering the amino acid sequence thereof. The alteration may be made, for example, by the addition of, or substitution by, one or more serine or threonine residues to the native sequence polypeptide (for O-linked glycosylation sites). The amino acid sequence may optionally be altered through changes at the DNA level, particularly by mutating the DNA encoding the polypeptide at preselected bases such that codons are generated that will translate into the desired amino acids.

Another means of increasing the number of carbohydrate moieties on a polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of a protein comprises linking the polypeptide to one of a variety of non-proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Polypeptides of the present invention may also be modified in a way to form chimeric molecules comprising a first polypeptide fused to another, heterologous polypeptide or amino acid sequence. In one embodiment, such a chimeric molecule comprises a fusion of a substrate molecule (e.g., a ubiquitin moiety, ubiquitin agent, or target protein) with a tag polypeptide which provides an epitope to which an anti-tag antibody can selectively bind. The epitope tag is generally placed at the amino- or carboxyl-terminus of the polypeptide. The presence of such epitope-tagged forms of a polypeptide can be detected using an antibody against the tag polypeptide. Also, providing an epitope tag enables the polypeptide to be readily purified by affinity purification using an anti-tag antibody or another type of affinity matrix that binds to the epitope tag. In an alternative embodiment, the chimeric molecule may comprise a fusion of a polypeptide disclosed herein with an immunoglobulin or a particular region of an immunoglobulin. For a bivalent form of the chimeric molecule, such a fusion could be to the Fc region of an IgG molecule. Tags for components of the invention are defined and described in detail below.

The present invention provides methods for assaying for the attachment of ubiquitin moiety to a substrate molecule of interest. Preferred embodiments of the invention involve combining ubiquitin moiety and ubiquitin agents, plus or minus target protein; and further in the presence or absence of a candidate agent; under conditions where ubiquitin moiety can attach to a substrate molecule of interest; and assaying for the attachment of the ubiquitin moiety to the substrate molecule of interest, for example, by measuring the amount of ubiquitin moiety (mono- or poly-ubiquitin moiety) attached to the substrate molecule. In these assays, the activity resulting from the combination of different ubiquitin agents and combination of different subunits of individual ubiquitin agents; plus or minus target protein; and further, in the presence or absence of a candidate ubiquitin agent; can be observed and measured.

In a preferred embodiment, the invention is additionally directed to a method of assaying for ubiquitin activating activity. By "ubiquitin activating activity", "ubiquitin moiety activation" and grammatical equivalents thereof is meant the binding or attachment of ubiquitin moiety to a substrate molecule that is preferably a ubiquitin activating agent. In a preferred embodiment, the ubiquitin activating agent is an E1. Preferably, the E1 forms a high energy thiolester bond with the ubiquitin moiety.

In a preferred embodiment, the invention is also directed to a method of assaying for ubiquitin conjugating activity. By "ubiquitin conjugating activity", "ubiquitin moiety conjugation" and grammatical equivalents thereof is meant the binding or attachment of an activated ubiquitin moiety to a ubiquitin conjugating agent. As will be appreciated by those in the art, due to the presence of the high energy thiolester bond in the conjugate of the ubiquitin moiety-ubiquitin conjugating agent, the attached ubiquitin moiety may be joined to other ubiquitin moiety at a low rate in the absence of the catalytic activity of a ubiquitin ligating agent (e.g., E3). Therefore, some of the ubiquitin moiety will be attached in the form of poly-ubiquitin moiety.

In a preferred embodiment, the invention is directed to a method of assaying ubiquitin ligating activity. By "ubiquitin ligating activity", "ubiquitin moiety ligation" and grammatical equivalents thereof is meant the transfer or attachment of ubiquitin moiety to a substrate molecule that is preferably a target protein or mono- or poly-ubiquitin moiety preferably attached to a target protein. Preferably, each ubiquitin moiety is covalently attached by the ubiquitin ligating agent such that a subsequent ubiquitin moiety may be attached to it, to form chains (poly-ubiquitin moieties) comprising a plurality of ubiquitin moiety molecules.

The present invention provides methods and compositions comprising combining ubiquitin moiety with other components. By "combining" is meant the addition of the various components into a reaction vessel under conditions in which attachment of ubiquitin moiety to a substrate molecule interest can occur. In a preferred embodiment, the reaction vessel is a well of a 96 well plate or other commercially available multiwell plate. In an alternate preferred embodiment, the reaction vessel is in a FACS machine. Other reaction vessels useful in the present invention include, but are not limited to 384 well plates and 1536 well plates. Still other reaction vessels useful in the present invention will be apparent to the skilled artisan.

The addition of the components may be sequential or in a predetermined order or grouping, as long as the conditions amenable to the attachment of ubiquitin to a substrate molecule of interest are obtained. Such conditions are well known in the art, and further guidance is provided below.

In a preferred embodiment, one or more components of the present invention comprise a tag. By "tag" is meant an attached molecule or molecules useful for the identification or isolation of the attached molecule(s), which are preferably substrate molecules. For example, a tag can be an attachment tag or a label tag. Components having a tag are referred to as "tag-X", wherein X is the component. For example, a ubiquitin moiety comprising a tag is referred to herein as "tag-ubiquitin moiety". Preferably, the tag is covalently bound to the attached component. When more than one component of a combination has a tag, the tags will be numbered for identification, for example "tag1-ubiquitin moiety". Components may comprise more than one tag, in which case each tag will be numbered, for example "tag 1,2-ubiquitin moiety". Preferred tags include, but are not limited to, a label, a partner of a binding pair, and a surface substrate binding molecule (or attachment tag). As will be evident to the skilled artisan, many molecules may find use as more than one type of tag, depending upon how the tag is used.

By "label" is meant a molecule that can be direct y (i.e., a primary label) or indirectly (i.e., a secondary label) detected; for example a label can be visualized and/or measured or otherwise identified so that its presence or absence can be known. As will be appreciated by those in the art, the manner in which this is performed will depend on the label. Preferred labels include, but are not limited to, fluorescent labels, label enzymes and radioisotopes.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., Science 263(5148):802–805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462–471 (1998); 3. Heim, R. and Tsien, R. Y. Curr. Biol. 6:178–182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12):5408–5417 (1993)), -galactosidase (Nolan, et al., Proc Natl Acad Sci USA 85(8):2603–2607 (April 1988)) and Renilla WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558) All of the above-cited references are expressly incorporated herein by reference.

In some instances, multiple fluorescent labels are employed. In a preferred embodiment, at least two fluorescent labels are used which are members of a fluorescence resonance energy transfer (FRET) pair. FRET is phenomenon known in the art wherein excitation of one fluorescent dye is transferred to another without emission of a photon. A FRET pair consists of a donor fluorophore and an acceptor flubrophore. The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Forster radius ($R_o$), which is typically 10–100 Å. Changes in the fluorescence emission spectrum comprising FRET pairs can be detected, indicating changes in the number of that are in close proximity (i.e., within 100 Å of each other). This will typically result from the binding or dissociation of two molecules, one of which is labeled with a FRET donor and the other of which is labeled with a FRET acceptor, wherein such binding brings the FRET pair in close proximity. Binding of such molecules will result in an increased fluorescence emission of the acceptor and/or quenching of the fluorescence emission of the donor.

FRET pairs (donor/acceptor) useful in the invention include, but are not limited to, EDANS/fluorescien, IAEDANS/fluorescein, fluorescein/tetramethylrhodamine, fluorescein/LC Red 640, fluorescein/Cy 5, fluorescein/Cy 5.5 and fluorescein/LC Red 705.

In another aspect of FRET, a fluorescent donor molecule and a nonfluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, DABCYL, QSY 7 and QSY 33. Useful fluorescent donor/quencher pairs include, but are not limited to EDANS/DABCYL, Texas Red/DABCYL, BODIPY/ DABCYL, Lucifer yellow/DABCYL, coumarin/DABCYL and fluorescein/QSY 7 dye.

The skilled artisan will appreciate that FRET and fluorescence quenching allow for monitoring of binding of labeled molecules over time, providing continuous information regarding the time course of binding reactions.

It is important to remember that ubiquitin moiety is ligated to a substrate molecule by its terminal carboxyl group to a lysine residue, including lysine residues on other ubiquitin moiety. Therefore, attachment of labels or other tags should not interfere with either of these active groups on the ubiquitin moiety. Amino acids may be added to the sequence of protein, through means well known in the art and described herein, for the express purpose of providing a point of attachment for a label. In a preferred embodiment, one or more amino acids are added to the sequence of a component for attaching a tag thereto, preferably a fluorescent label. In a preferred embodiment, the amino acid to which a fluorescent label is attached is Cysteine.

By "label enzyme" is meant an enzyme which may be reacted in the presence of a label enzyme substrate which produces a detectable product. Suitable label enzymes for use in the present invention include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., Previews 247:6–9 (1998), Young, J. Virol. Methods 24:227–236 (1989), which are each hereby incorporated by reference in their entirety.

By "radioisotope" is meant any radioactive molecule. Suitable radioisotopes for use in the invention include, but are not limited to $^{14}C$, $^3H$, $^{32}P$, $^{33}P$, $^{35}S$, $^{125}I$, and $^{131}I$. The use of radioisotopes as labels is well known in the art.

In addition, labels may be indirectly detected, that is, the tag is a partner of a binding pair. By "partner of a binding pair" is meant one of a first and a second moiety, wherein said first and said second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/antifluorescein, lucifer yellow/anti-lucifer yellow, and rhodamine anti-rhodamine), biotin/avid (or biotin/ streptavidin) and calmodulin binding protein (CBP)/ calmodulin. Other suitable binding pairs include polypeptides such as the FLAG-peptide [Hopp et al., BioTechnology, 6:1204–1210 (1988)]; the KT3 epitope peptide [Martin et al., Science, 255:192–194 (1992)]; tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)] and the antibodies each thereto. Generally, in a preferred embodiment, the smaller of the binding pair partners serves as the tag, as steric considerations in ubiquitin moiety ligation may be important. As will be appreciated by those in the art, binding pair partners may be used in applications other than for labeling, as is further described below.

As will be appreciated by those in the art, a partner of one binding pair may also be a partner of another binding pair. For example, an antigen (first moiety) may bind to a first antibody (second moiety) which may, in turn, be an antigen for a second antibody (third moiety). It will be further appreciated that such a circumstance allows indirect binding of a first moiety and a third moiety via an intermediary second moiety that is a binding pair partner to each.

As will be appreciated by those in the art, a partner of a binding pair may comprise a label, as described above. It will further be appreciated that this allows for a tag to be indirectly labeled upon the binding of a binding partner comprising a label. Attaching a label to a tag which is a partner of a binding pair, as just described, is referred to herein as "indirect labeling".

By "surface substrate binding molecule" or "attachment tag" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5 substrate [Field et al., *Mol. Cell. Biol.*, 8:2159–2165 (1988)]; the c-myc tag and the 8F9, 3C7, 6E10, G4, B7 and 9E10 antibody substrates thereto [Evan et al., *Molecular and Cellular Biology*, 5:3610–3616 (1985)]; and the Herpes Simplex virus glycoprotein D (gD) tag and its antibody substrate [Paborsky et al., *Protein Engineering*, 3(6):547–553 (1990)]. In general, surface binding substrate molecules useful in the present invention include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin.

Production of antibody-embedded substrates is well known; see Slinkin et a., *Bioconj. Chem.* 2:342–348 (1991); Torchilin et al., supra; Trubetskoy et al., *Bioconj. Chem.* 3:323–327 (1992); King et al., *Cancer Res.* 54:6176–6185 (1994); and Wilbur et a., *Bioconjugate Chem.* 5:220–235 (1994) (all of which are hereby expressly incorporated by reference), and attachment of or production of proteins with antigens is described above.

Calmodulin-embedded substrates are commercially available, and production of proteins with CBP is described in Simcox et al., Strategies 8:40–43 (1995), which is hereby incorporated by reference in its entirety.

As will be appreciated by those in the art, tag-components of the invention can be made in various ways, depending largely upon the form of the tag. Components of the invention and tags are preferably attached by a covalent bond.

The production of tag-polypeptides by recombinant means when the tag is also a polypeptide is described below. Production of FLAG-labeled proteins is well known in the art and kits for such production are commercially available (for example, from Kodak and Sigma). Methods for the production and use of FLAG-labeled proteins are found, for example, in Winston et al., *Genes and Devel.* 13:270–283 (1999), incorporated herein in its entirety, as well as product handbooks provided with the above-mentioned kits.

Biotinylation of target molecules and substrates is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known (Id.).

Methods for labeling of proteins with radioisotopes are known in the art. For example, such methods are found in Ohta et al., *Molec. Cell* 3:535–541 (1999), which is hereby incorporated by reference in its entirety.

Production of proteins having His-tags by recombinant means is well known, and kits for producing such proteins are commercially available. Such a kit and its use is described in the QIAexpress Handbook from Qiagen by Joanne Crowe et al., hereby expressly incorporated by reference.

The functionalization of labels with chemically reactive groups such as thiols, amines, carboxyls, etc. is generally known in the art. In a preferred embodiment, the tag is functionalized to facilitate covalent attachment.

The covalent attachment of the tag may be either direct or via a linker. In one embodiment, the linker is a relatively short coupling moiety, that is used to attach the molecules. A coupling moiety may be synthesized directly onto a component of the invention, ubiquitin moiety for example, and contains at least one functional group to facilitate attachment of the tag.

Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer. In a preferred embodiment, the covalent attachment is direct, that is, no linker is used. In this embodiment, the component preferably contains a functional group such as a carboxylic acid which is used for direct attachment to the functionalized tag. It should be understood that the component and tag may be attached in a variety of ways, including those listed above. What is important is that manner of attachment does not significantly alter the functionality of the component. For example, in tag-ubiquitin moiety, the tag should be attached in such a manner as to allow the ubiquitin moiety to be covalently attached to another ubiquitin moiety to form polyubiquitin moiety chains. As will be appreciated by those in the art, the above description of covalent attachment of a label and ubiquitin moiety applies equally to the attachment of virtually any two molecules of the present disclosure.

In a preferred embodiment, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag will depend on the site of attachment to either a linker, as outlined above or a component of the invention. Thus, for example, for direct linkage to a carboxylic acid group of a ubiquitin moiety, amino modified or hydrazine modified tags will be used for coupling via carbodiimide chemistry, for example using 1-ethyl-3-(3-dimethylaminopropyl)-carbodiimide (EDAC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the tag, such as is commercially available for many of the tags described herein.

In a preferred embodiment, ubiquitin moiety is in the form of tag-ubiquitin moiety, wherein, tag is a partner of a binding pair. Preferably in this embodiment the tag is FLAG and the binding partner is anti-FLAG. Preferably in this embodiment, a label is attached to the FLAG by indirect labeling. Preferably, the label is a label enzyme. Most preferably, the label enzyme is horseradish peroxidase, which is reacted with a fluorescent label enzyme substrate. Preferably, the label enzyme substrate is Luminol. Alternatively, the label is a fluorescent label.

In another preferred embodiment, ubiquitin moiety is in the form of tag-ubiquitin moiety, wherein the tag is a fluorescent label. In a particularly preferred embodiment, ubiquitin moiety is in the form of tag1-ubiquitin moiety and tag2-ubiquitin moiety, wherein tag1 and tag2 are the members of a FRET pair. In an alternate preferred embodiment, ubiquitin moiety is in the form of tag1-ubiquitin moiety and tag2-ubiquitin moiety, wherein tag1 is a fluorescent label and tag2 is a quencher of the fluorescent label. In either of these preferred embodiments, when tag1-ubiquitin moiety and tag2-ubiquitin moiety are attached to a substrate molecule of interest through the activity of a ubiquitin agent, preferably tag1 and tag2 are within 100 Å of each other, more preferable within 70 Å, still more preferably within 50 Å, even more preferably within 40 Å, and in some cases, preferably within 30 Å or less.

In yet another preferred embodiment, ubiquitin moiety is in the form of tag1,2-ubiquitin moiety and tag1,3-ubiquitin moiety, wherein tag1 is a member of a binding pair, preferably FLAG, tag2 is a fluorescent label and tag3 is either a fluorescent label such that tag2 and tag3 are members of a FRET pair or tag3 is a quencher of tag2.

In a preferred embodiment, one or more amino acids are added to the ubiquitin moiety sequence, using recombinant techniques as described herein, to provide an attachment point for a tag, preferably a fluorescent label or a quencher. In a preferred embodiment, the one or more amino acids are Cys or Ala-Cys. Preferably, the one or more amino acids are attached to the N-terminal of the ubiquitin moiety. In a preferred embodiment, the one or more amino acids intervenes the sequence of a FLAG tag and the ubiquitin moiety. In a preferred embodiment, the tag, preferably a fluorescent label or a quencher, is attached to the added Cysteine.

In some embodiments, the methods of the present invention comprise the use of a ubiquitin activating agent. As used herein "ubiquitin activating agent" refers to a ubiquitin agent, preferably a protein, capable of transferring or attaching a ubiquitin moiety to a ubiquitin conjugating agent. In a preferred embodiment, the ubiquitin activating agent forms a high energy thiolester bond with ubiquitin moiety, thereby "activating" the ubiquitin moiety. In another preferred embodiment, the ubiquitin activating agent binds or attaches ubiquitin moiety. In another preferred embodiment, the ubiquitin activating agent is capable of transferring or attaching ubiquitin moiety to a substrate molecule that is a mono- or poly-ubiquitin moiety. In a preferred embodiment, the ubiquitin activating agent is capable of transferring or attaching ubiquitin moiety to a mono- or poly-ubiquitinated ubiquitin conjugating agent.

In a preferred embodiment the ubiquitin activating agent is an E1. In a preferred embodiment, the E1 is capable of transferring or attaching ubiquitin moiety to an E2, defined below.

In the methods and compositions of the present invention, the ubiquitin activating agent comprises an amino acid sequence or a nucleic acid corresponding to a sequence of an Genbank data base accession number listed in Table 1 below and incorporated herein by reference.

TABLE 1

| ORG | SYMBOL | DESCRIPTION | ACCESSION NO. |
|---|---|---|---|
| Hs | APPBPI | amyloid beta precursor protein binding protein 1, 59 kD | NM_003905 |
| Hs | FLJ23251 | hypothetical protein FLJ23251 | NM_024818 |
| Hs | GSA7 | ubiquitin activating enzyme E1-like protein | NM_006395 |
| Hs | | similar to ubiquitin-activating enzyme E1 (A1S9T and BN75 temperature sensitivity complementing) (*H. sapiens*) | XM_088743 |
| Hs | | similar to SUMO-1 activating enzyme subunit 1; SUMO-1 activating enzyme E1 N subunit; sentrin/SUMO-activating protein AOS1; ubiquitin-like protein SUMO-1 activating enzyme | XM_090110 |
| Hs | SAE1 | SUMO-1 activating enzyme subunit 1 | NM_005500 and XM_009036 |
| Dm | Uba1 | Ubiquitin activating enzyme 1 | NG_000652 and NM_057962 |
| Dm | Uba2 | Smt3 activating enzyme 2 | NM_080017 |
| Hs | UBA2 | SUMO-1 activating enzyme subunit 2 | NM_005499 |
| Hs | UBE1 | ubiquitin-activating enzyme E1 (A1S9T and BN75 temperature sensitivity complementing) | NM_003334 and XM_033895 |
| Hs | UBE1C | ubiquitin-activating enzyme E1C (UBA3 homolog, yeast) | NM_003968 |
| Rn | Ube1c | Ubiquitin-activating enzyme E1C | NM_057205 |
| Mm | Ube1l | Ubiquitin-activating enzyme E1-like | |
| Hs | UBE1L | Ubiquitin-activating enzyme E1-like | NM_003335 |
| Mm | Ube1x | ubiquitin-activating enzyme E1, Chr X | NM_009457 |
| Mm | Ube1y1 | ubiquitin-activating enzyme E1, Chr Y 1 | NM_011667 |
| Mm | Ube1y1-ps1 | ubiquitin-activating enzyme E1, Chr Y, pseudogene 1 | M88481 and U09053 |
| Mm | Ube1y1-ps2 | ubiquitin-activating enzyme E1, Chr Y-1, pseudogene 2 | U09054 |

Sequences encoding a ubiquitin activating agent may also be used to make variants thereof that are suitable for use in the methods and compositions of the present invention. The ubiquitin activating agents and variants suitable for use in the methods and compositions of the present invention may be made as described herein.

In a preferred embodiment, E1 proteins useful in the invention include the polypeptides encoded by the amino acid sequence corresponding to GENBANK accession numbers A38564, S23770, AAA61246, P22314, CAA40296 and BAA33144, incorporated herein by reference. In a preferred embodiment, E1 has the amino acid sequence shown in FIG. 6B or is encoded by a nucleic acid comprising the sequence shown in FIG. 6A. Preferably E1 is human E1. E1 is commercially available from Affiniti Research Products (Exeter, U.K.).

In a preferred embodiment, nucleic acids which may be used for producing E1 proteins for the invention include, but are not limited to, those disclosed by GENBANK accession numbers M58028, X56976 and AB012190, incorporated herein by reference. In a preferred embodiment, E1 is encoded by a nucleic acid having a sequence consisting essentially of the sequence shown in FIG. 6A. Variants of the cited E1 proteins, also included in the term "E1", can be made as described herein.

In some embodiments, the methods of the present invention comprise the use of a ubiquitin conjugating agent. As used herein "ubiquitin conjugating agent" refers to a ubiquitin agent, preferably a protein, capable of transferring or attaching ubiquitin moiety to a ubiquitin ligating agent. In some cases, the ubiquitin conjugating agent is capable of directly transferring or attaching ubiquitin moiety to lysine residues in a target protein (Hershko et al. (1983) J. Biol. Chem. 258:8206–8214). In a preferred embodiment, the ubiquitin conjugating agent is capable of transferring or attaching ubiquitin moiety to a mono- or poly-ubiquitin moiety preferably attached to a ubiquitin agent or target protein. In a preferred embodiment, the ubiquitin conjugating agent is capable of transferring ubiquitin moiety to a mono- or poly-ubiquitinated ubiquitin ligating agent.

In a preferred embodiment the ubiquitin conjugating agent is an E2. In a preferred embodiment, ubiquitin moiety is transferred from E1 to E2. In a preferred embodiment, the transfer results in a thiolester bond formed between E2 and ubiquitin moiety. In a preferred embodiment, E2 is capable of transferring or attaching ubiquitin moiety to an E3, defined below.

In the methods and compositions of the present invention, the ubiquitin activating agent comprises an amino acid sequence or a nucleic acid sequence corresponding to a sequence of an Genbank data base accession number listed in Table 2 below and incorporated herein by reference.

TABLE 2

| Name | ALIAS | Accession No. (nucleic acid sequences) | Accession No. (amino acid sequences) |
|---|---|---|---|
| UBE2D1 Hs UBC4/5 homolog | UBE2D1, UBCH5A, UBC4/5 homolog | NM_003338.1 | NP_003329.1 |
| UBC9 *Gallus gallus* | UBC9, SUMO-conjugating enzyme | AB069964.1 | BAB68210.1 |
| UBC9 *Mus musculus* | mUB69 | U76416.1 | AAB18790.1 |
| UBC9/UBE21 Hs ?? | UBE21 | U45328.1 | AAA86662.1 |
| UBC9 isoform/MGC:3994 Hs | MGC:3994, IMAGE:2819732, UBC9 isoform | BC004437.1 | AAH04437.1 |
| UBC9 Hs | UBC9, UBE21 | NM_003345.1 | NP_003336.1 |
| FTS homolog Hs + 1aa | fused toes homolog, FLJ13258 | NM_022476.1 | NP_071921.1 |
| FLJ13988 Hs | FLJ13988, clone Y79AA1002027, sim to E2–18 | AK024050.1 | BAB14800.1 |
| MGC:13396 Hs | | BC010900.1 | AAH10900.1 |
| UBE2V2 Hs | MGC:13396, IMAGE:4081461 | NM_003350.2 | NP_003341.1 |
| MGC:10481 Hs | UBE2V2, EDAF-1, MMS2, UEV2, DDVIT1, ED | BC004862.1 | AAH04862.1 |
| XM_054332.1 Hs | | XM_054332.1 | XP_054332.1 |
| FLJ13855 Hs | MGC:10481, IMAGE:3838157 | XM_030444.3 | XP_030444.1 |
| E2–230K homolog Hs | | NM_022066.1 | NP_071349.1 |
| UBE2V2 Hs | FLJ13855 | NM_003339.1 | NO_003330.1 |
| UBE2D3 Hs 1 SNP | E2–230K ortholog, FLJ12878, | NM_003340.1 | NP_003331.1 |
| Non-canon Ub-conj Enz (NCUBE1) | KIAA1734 | NM_016336.2 | NP_057420.2 |
| HSPC150 Hs | UBE2D2, UBCH5B, UBC4, UBC4/5 homolog | NM_014176.1 | NP_054895.1 |
| Brain 1AP repeat contain 6 (BIRC6) | UBE2D3, UBCH5C, UBC4/5 homolog NCUBE1, HSU93243, HSPC153, CGI-76 BIRC6, KIAA1289, apollon | NM_016252.1 | NP_057336.1 |
| UBC8 Mus | E2–20K, UBE2H | NM_009459.1 | NP_033485.1 |
| UBC8 Hs | UBE2H, UBCH, UBCH2, UBC8 | NM_003344.1 | NP_003335.1 |
| UBC8 Hs 6SNP | homolog | NM-003344.1 | NP-003335.1 |
| UBC8 Hs no 5' | UBE2H, UBCH, UBCH2, UBC8 homolog | | |
| RAD6 homolog Hs | UBE2B, RAD6B, HHR6B, UBC2, RAD6 homolog | NM_003337.1 | NP_003328.1 |
| UBE2V1 var 3 Hs | UBE2V1, CIR1, UEV1, UEV1A, CROC-1, CRO | NM_022442.1 | NP_071887.1 |
| UBE2V1 var 1 Hs early stop, 56aa | UBE2V1, CIR1, UEV1, UEV1A, CROC-1, CRO | NM_021988.2 | NP_068823.1 |
| UBE2V1 var 2 Hs | UBE2V1, CIR1, UEV1, UEV1A, CROC-1, CRO | NM_003349.3 | NP_003340.1 |
| UBE2L6 Hs | UBE2L6, UBCH8, RIG-B | NM_004223.1 | NP_004214.1 |
| UBE2L3 Hs 2 SNP | UBE2L3, UBCH7 | NM_003347.1 | NP_003338.1 |
| UBE2E1 Hs | UBE2E1, UBCH6, UBC4/5 homolog | NM_003341.1 | NP_003332.1 |
| RAD6/UBE2A Hs | UBE2A, RAD6A, HHR6A, UBC2, RAD6 homolog | NM_003336.1 | NP_003327.1 |
| UBE2E3 Hs | | NM_006357.1 | NP_006348.1 |
| UBC12/UBE2M Hs | UBE2E3, UBCH9, UBC4/5 homolog | NM_003969.1 | NP_003960.1 |
| UBC7/UBE2G1 Hs | UBE2M, HUBC12, UBC12 homolog UBE2G1, UBC7 homolog | NM_003342.1 | NP_003333.1 |
| Huntingtin interact prot 2 (HIP2) Hs | HIP2, LIG, E2–25K | NM_005339.2 | NP_005330.1 |
| LIG/HIP2 variant Hs | LIG, HIP2 alternative splicing form | ABO22436.1 | BAA78556.1 |
| UBC6p Hs | UBC6p, UBC6 | NM_058167.1 | NP_477515.1 |
| UBC6 Hs | UBC6 | AF296658.1 | AAK52609.1 |
| HBUCE1/UBE2D2 var Hs | HBUCE1, LOC51619 | NM_015983.1 | NP_057067.1 |
| UBE2G2/UBC7 homolog Hs | UBE2G2, UBC7 homolog | XM_036087.1 | XP_036087.1 |
| NEDD8-conj enzyme 2 (NCE2) Hs | NCE2 | NM_080678.1 | NP_542409.1 |
| CDC34 Hs | CDC34, E2-CDC34, E2–32 complementing IMAGE:3458173 | NM_004359.1 BC000848.1 | NP_004350.1 AAH00848.1 |

TABLE 2-continued

| Name | ALIAS | Accession No. (nucleic acid sequences) | Accession No. (amino acid sequences) |
|---|---|---|---|
| IMAGE:3458173/NICE-5 var | | | |
| UBE2C Hs | UBE2C, UBCH10 | NM_007019.1 | NP_008950.1 |
| UBE2C possible short form Hs | UBE2C, UBCH10 | NM_007019.1 | NP_008950.1 |
| UBC3/UBE2N Hs | UBE2N, UBCH-BEN, UBC13 hom., | NM_003348.1 | NP_003339.1 |
| FLJ25157 Hs | sim to bend | AK057886.1 | BAB71605.1 |
| TSG101 Hs 1 SNP | FLJ25157, highly similar to E2–23 | NM_006292.1 | NP_006283.1 |
| MGC:21212/NICE-5 var Hs | Tumor susceptibility gene 101 MCG:21212, IMAGE:3907760, sim to NICE-5 | BC017708.1 | AAH17708.1 |

Sequences encoding a ubiquitin conjugating agent may also be used to make variants thereof that are suitable for use in the methods and compositions of the present invention. The ubiquitin conjugatin agents and variants suitable for use in the methods and compositions of the present invention may be made as described herein.

In a preferred embodiment, the E2 used in the methods and compositions of the present invention comprises an amino acid sequence or nucleic acid sequence of a sequence corresponding to an Genbank data base accession number in the following list: AC37534, P49427, CAA82525, AAA58466, AAC41750, P51669, AAA91460, AAA91461, CAA63538, AAC50633, P27924, AAB36017, Q16763, AAB86433, AAC26141, CAA04156, BAA11675, Q16781, NP_003333, BAB18652, AAH00468, CAC16955, CAB76865, CAB76864, NP_05536, O00762, XP_009804, XP_009488, XP_006823, XP_006343, XP_005934, XP_002869, XP_003400, XP_009365, XP_010361, XP_004699, XP_004019, O14933, P27924, P50550, P52485, P51668, P51669, P49459, P37286, P23567, P56554, and CAB45853, each of which is incorporated herein by reference. Particularly preferred are sequences corresponding to Genbank data base accession numbers NP003331, NP003330, NP003329, P49427, AAB53362, NP008950, XP009488 and AAC41750, also incorporated by reference. The skilled artisan will appreciate that many different E2 proteins and isozymes are known in the filed and may be used in the present invention, provided that the E2 has ubiquitin conjugating activity. Also specifically included within the term "E2" are variants of E2, which can be made as described herein.

In a preferred embodiment, E2 is one of Ubc5 (Ubch5, preferably Ubch5c), Ubc3 (Ubch3), Ubc4 (Ubch4) and UbcX (Ubc10, Ubch10). In a preferred embodiment, E2 is Ubch5c. In a preferred embodiment, E2 has the amino acid sequence shown in FIG. 7B or is encoded by a nucleic acid consisting essentially of the sequence shown in FIG. 7A.

The E2 used in the methods and compositions of the present invention, comprises a nucleic acid sequence of a sequence corresponding to Genbank data base accession number L2205, Z29328, M92670, L40146, U39317, U39318, X92962, U58522, S81003, AF031141, AF075599, AJ000519, XM009488, NM007019, U73379, L40146, or D83004, each of which is incorporated herein by reference. As described above, variants of these and other E2 encoding nucleic acids may also be used to make variant E2 proteins.

Figure 7A:
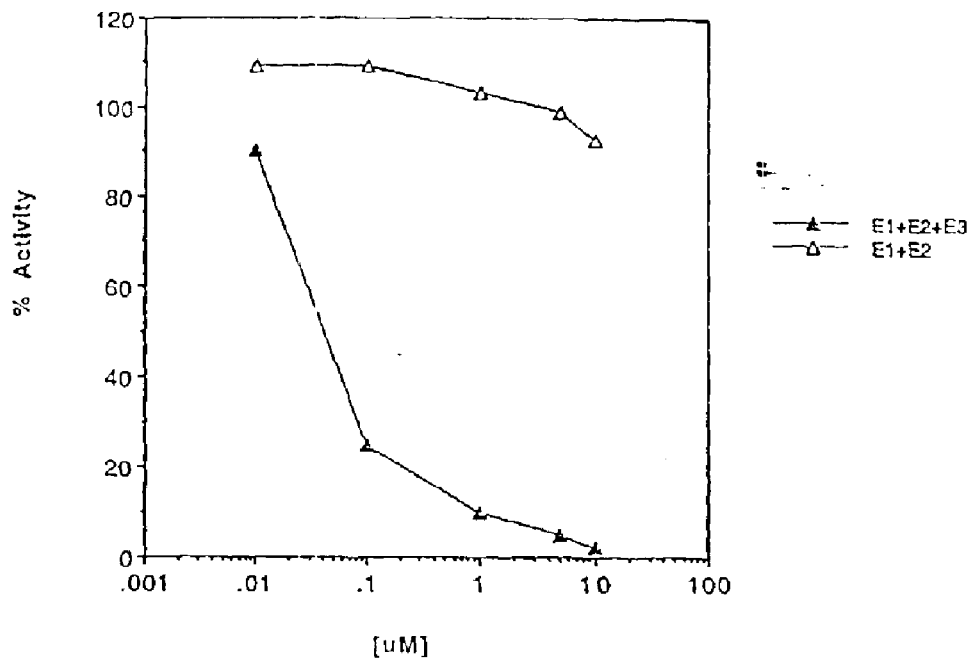
FIG. 7A shows the results of a candidate agent having a concentration-dependent effect on the attachment of ubiquitin moiety to an E3 (by combining ubiquitin moiety, E1, E2, and E3), but does not have an effect on the attachment of ubiquitin moiety to an E2 (by combining ubiquitin moiety, E1, and E2), thus affecting only the attachment of ubiquitin moiety to an E3.
Figure 7B:
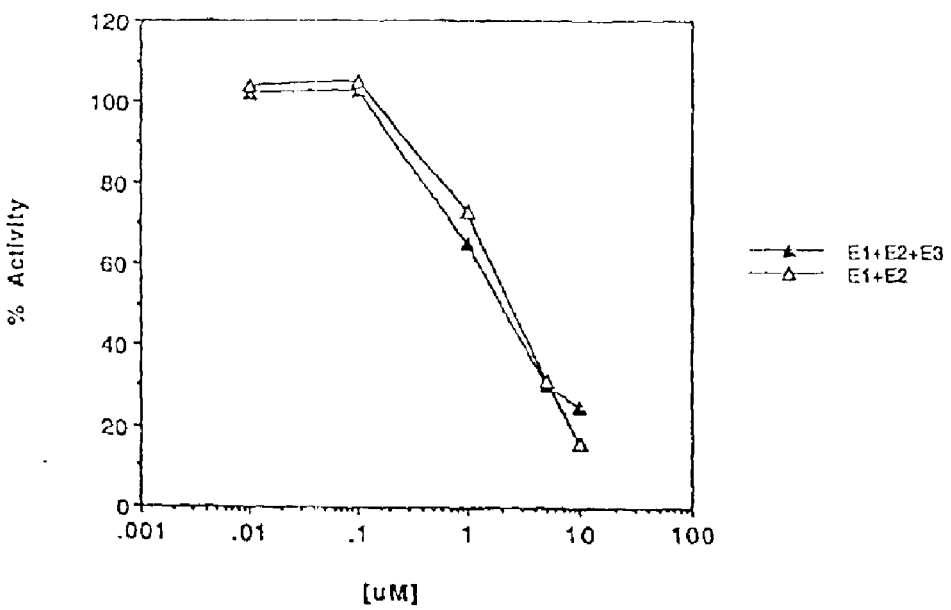
FIG. 7B shows the results for a candidate modulator having a concentration-dependent effect on both the attachment of ubiquitin moiety to an E2 and the attachment of ubiquitin moiety to an E3, thus affecting a component other than the E3.

In a preferred embodiment, the nucleic acid used to make E2 comprises the sequence shown in FIG. 7A.

In a preferred embodiment, E2 has a tag, as defined above, with the complex being referred to herein as "tag-E2". Preferred E2 tags include, but are not limited to, labels, partners of binding pairs and substrate binding elements. In a most preferred embodiment, the tag is a His-tag or GST-tag.

In some embodiments, the methods of the present invention comprise the use of a ubiquitin ligating agent. As used herein "ubiquitin ligating agent" refers to a ubiquitin agent, preferably a protein, capable of transferring or attaching a ubiquitin moiety to a target molecule. In some cases, the ubiquitin agent is capable of transferring or attaching ubiquitin moiety to itself or another ubiquitin ligating agent. In a preferred embodiment, the ubiquitin ligating agent is an E3.

As used herein "E3" refers to a ubiquitin ligating agent comprising one or more subunits, preferably polypeptides, associated with the activity of E3 as a ubiquitin ligating agent (i.e., associated with the ligation or attachment of ubiquitin moiety to a target protein, and in some cases, to itself or another E3). In a preferred embodiment, E3 is a member of the HECT domain E3 ligating agents. In another preferred embodiment, E3 is a member of the RING finger domain E3 ligating agents. In a preferred embodiment, E3 comprises a ring finger subunit and a Cullin subunit. Examples of RING finger polypeptides suitable for use in the methods and compositions of the present invention include, but are not limited to, ROC1, ROC2 and APC11. Examples of Cullin polypeptides suitable for use in the methods and compositions of the present invention include, but are not limited to, CUL1, CUL2, CUL3, CUL4A, CUL4B, CUL5 and APC2. In another preferred embodiment, the E3 is mdm2.

In the methods and compositions of the present invention, the ubiquitin ligating agent comprises an amino acid sequence or a nucleic acid sequence of a sequence corresponding to an accession number in the Genbank data base, European Molecular Biology Laboratories (EMBL) data base, or ENSEMBL data base (a joint project of the European Molecular Biology Laboratories and the Sanger Institute) listed in Table 3 below and incorporated herein by reference. The accession numbers from the Genbank data base can be found as stated above. The accession numbers from the EMBL data base are found at www.embl-heidelberg.de. The accession numbers from the ENSEMBL data base are found at www.ensembl.or.

TABLE 3

| Accession No | Accession No | Accession No | Accession No | Accession No | Accession No | Accession No | Accession No | Accession No |
|---|---|---|---|---|---|---|---|---|
| AAD15547 | AAH22038 | O75485 | Q96BD4 | Q96T88 | Q9BYV6 | Q9H073 | Q9H920 | |
| AAF42995 | AAH22403 | O75592 | Q96BD | Q96K03 | Q99496 | Q9BZX6 | Q9H083 | Q9H9B0 |
| AAF91315 | AAH22510 | O75598 | 5Q96BE6 | Q96K19 | Q99579 | Q9BZX7 | Q9H0A6 | Q9H9B5 |
| AAF97687 | AAL30771 | O75615 | Q96BH1 | Q96K21 | Q99675 | Q9BZX8 | Q9H0M8 | Q9H9P5 |
| AAG50176 | AAL31641 | O75866 | Q96BL1 | Q96KD9 | Q99942 | Q9BZX9 | Q9H0V6 | Q9H9T2 |
| AAG50180 | AAL36460 | O76050 | Q96BM5 | Q96KL0 | Q9BPW2 | Q9BZY0 | Q9H0X6 | Q9H9V4 |
| AAG53500 | AAL40179 | O76064 | Q96BQ3 | Q96KM9 | Q9BQ47 | Q9BZY1 | Q9H270 | Q9H9Y7 |
| AAG53509 | AAL40180 | O94896 | Q96BS3 | Q96LD4 | Q9BQV0 | Q9BZY2 | Q9H2A8 | A9HA51 |
| AAH00832 | AAL76101 | O94941 | Q96BX2 | Q96M70 | Q9BRZ2 | Q9BZY3 | Q9H2S3 | Q9HAC1 |
| AAH02922 | CAC81706 | O94972 | Q96C24 | Q96MJ7 | Q9BS04 | Q9BZY4 | Q9H2S4 | Q9HAM2 |
| AAH04978 | CAC85986 | O95159 | Q96CA5 | Q96MT1 | Q9BSE9 | Q9BZY5 | Q9H2S5 | Q9HAP7 |
| AAH05375 | CAD19102 | O95247 | Q96CC2 | A96MX5 | Q9BSL8 | Q9BZY6 | Q9H348 | Q9HBD2 |
| AAH13580 | O00237 | O95277 | Q96D24 | Q96MZ7 | Q9BSM1 | Q9BZY8 | Q9H463 | Q9HCL8 |
| AAH15738 | O00463 | O95604 | Q96D38 | Q96NI4 | Q9BSV9 | Q9BZY9 | Q9H4C2 | Q9HCR0 |
| AAH16174 | O00635 | O95627 | Q96D59 | Q96NS4 | KIAA066 | Q9C017 | Q9H4C3 | Q9HCR1 |
| AAH16924 | O14616 | O95628 | Q96DB4 | Q96NT2 | Q9BTC5 | Q9C018 | Q9H4C4 | Q9HCR2 |
| AAH17370 | O14686 | O96028 | Q96DV2 | Q96P09 | Q9BTD9 | Q9C019 | Q9H4C5 | Q9HCS6 |
| AAH17585 | O15057 | Q14527 | Q96DV3 | Q96PF7 | Q9BU73 | Q9C021 | Q9H4J2 | Q9NPN4 |
| AAH17592 | O15262 | Q14536 | Q96DX4 | Q96PH3 | Q9BUW4 | QOC025 | Q9H5E4 | Q9NNP8 |
| AAH17707 | O15344 | Q14848 | Q96DY5 | Q96PK3 | Q9BUZ4 | Q9C026 | Q9H5F1 | Q9NPQ1 |
| AAH18104 | O43164 | Q15156 | Q96EL5 | Q96PM5 | Q9BV68 | Q9C027 | Q9H5K0 | Q9NQ86 |
| AAH18107 | O43255 | Q15290 | Q96EP1 | Q96PR5 | Q9BVG3 | Q9C029 | Q9H5L8 | Q9NQP8 |
| AAH18198 | O43269 | Q15521 | Q96EP8 | Q96PU4 | Q9BW41 | Q9C030 | Q9H5P2 | Q9NR13 |
| AAH18337 | O43270 | Q15959 | Q96EQ8 | Q96PX1 | Q9BW90 | Q9C031 | Q9H5S6 | Q9NRL2 |
| AAH18647 | O43567 | Q16030 | Q96F06 | Q96QB5 | Q9BWF2 | Q9C032 | Q9H647 | Q9NRT4 |
| AAH19283 | O60272 | Q92250 | Q96F37 | Q96QB6 | Q9BWL5 | Q9C033 | Q9H6D9 | Q9NRT6 |
| AAH19355 | O60291 | Q92897 | Q96F67 | Q96QY9 | Q9BWP7 | Q9C034 | Q9H6S6 | Q9NS55 |
| AAH20556 | O60372 | Q969K3 | Q96GF1 | Q96RF3 | Q9BX37 | Q9C035 | Q9H6W8 | Q9NS56 |
| AAH20964 | O60630 | Q969Q1 | Q96GT5 | Q96RF8 | Q9BXI1 | Q9C036 | Q9H6Y7 | Q9NS56 |
| AAH20984 | O75150 | Q969V5 | Q96H69 | Q96RW5 | Q9BY78 | Q9C037 | Q9H748 | Q9NS91 |
| AAH20994 | KIAA0661 | Q96A37 | Q96IB6 | Q96SH4 | Q9BYE7 | Q9C038 | Q9H874 | Q9NSR1 |
| AAH21258 | O75162 | Q96Q61 | A96ID9 | Q96SJ1 | Q9BYV2 | Q9C039 | Q9H890 | Q9NSX7 |
| AAH21570 | O75188 | Q96AK4 | Q96J90 | Q96SL3 | Q9BYV3 | Q9C040 | Q9H8K2 | Q9NTX6 |
| AAH21571 | O75341 | Q96AX9 | Q96JD3 | Q96SR5 | Q9BYV4 | Q9C0B0 | Q9H8V9 | Q9NTX7 |
| AAH21925 | O75382 | Q96BD3 | Q96JL5 | Q96T06 | Q9BYV5 | Q9C0G7 | Q9H8W5 | Q9NU68 |
| AAH21925 | O75382 | Q96BD3 | Q96JL5 | Q96T18 | Q9BYV5 | Q9C0G7 | Q9H8W5 | Q9NU68 |

| Accession No | Accession No | Accession No | Accession No | Accession No | Accession No | Accession No | Accession No |
|---|---|---|---|---|---|---|---|
| Q9NUH2 | Q9NZS9 | Q9UIG0 | 9UQPQ7 | O15151 | Q9BXT8 | O94822 | Q13263 |
| Q9NUR4 | Q9NZT8 | Q9UIG1 | Q9UPR2 | O15541 | Q9BYM8 | O95376 | Q13489 |
| Q9NUW5 | Q9P0J9 | Q9UJ97 | Q9UQ11 | O60858 | Q9BZR9 | P15918 | Q13490 |
| Q9NVD5 | Q9P0P0 | Q9UJJ8 | Q9Y225 | O75678 | Q9H000 | P19474 | Q13702 |
| Q9NVP6 | Q9P115 | Q9UJL3 | Q9Y254 | P14373 | Q9NS80 | P22681 | Q14839 |
| Q9NW38 | Q9P1Y6 | Q9UJR9 | Q9Y2E6 | P28328 | Q9NV58 | P29590 | Q15326 |
| Q9NWD2 | Q9P200 | Q9UJV3 | Q9Y2N1 | P35226 | Q9UDY6 | P35227 | Q92785 |
| Q9NWX1 | Q9P2G1 | Q9UK16 | Q9Y3C5 | P46100 | Q9UHC7 | P36406 | Q99728 |
| Q9NX39 | Q9P2L3 | Q9UKV5 | Q9Y3V1 | P51948 | Q9ULX5 | P38398 | Q9HCM9 |
| Q9NXC0 | Q9P2M3 | Q9ULK6 | Q9Y3V3 | Q12899 | Q9UMT8 | P49754 | Q9NVW2 |
| Q9NXD0 | Q9UBF6 | Q9ULT6 | Q9Y4I0 | Q12933 | Q9Y4X5 | P50876 | Q9NYG5 |
| Q9NXI6 | Q9UDN7 | Q9ULW4 | Q9Y4K3 | Q12986 | Q9Y508 | P53804 | Q9ULV8 |
| Q9NZ15 | Q9UEK4 | Q9UMH1 | Q9Y4L5 | Q13049 | O00623 | P98170 | Q9UPN9 |
| Q9NZB4 | Q9UF32 | Q9UMQ2 | Q9Y577 | Q13064 | O5164 | Q06587 | Q9Y252 |
| Q9NZE3 | Q9UHE7 | Q9UNR9 | Q9Y5M7 | Q13114 | O60683 | Q12873 | |
| Q9NZE9 | Q9UHW2 | Q9UPQ2 | Q9Y6E4 | Q13434 | O75677 | Q13191 | |
| Q9NZN6 | Q9UID0 | Q9UPQ4 | Q9Y6U1 | Q14258 | O75679 | Q13233 | |

| Hect domain proteins (Embl data base) | | | Ringfinger domain proteins (GenBank data base) | |
|---|---|---|---|---|
| AAH19105 | AAF50078 | T14346 | BAB23311 | AAL13848 |
| AAH19345 | AAH21525 | T40821 | T40821 | XP_004990 |
| AAH21144 | AAH02582 | S66562 | NP_192994 | BAB29387 |
| O00307 | NP_055486 | NP_008944 | AAF57824 | BAA92558 |
| O00308 | BAB133352 | NP_008945 | NP_080106 | AAG45422 |
| O14996 | NP_492389 | NP_032421 | T37964 | AAF36454 |
| O15029 | XP_048020 | AAK33088 | NP_035798 | AAF36455 |
| O15033 | BAB28637 | AAL39551 | BAB14280 | AAK14420 |
| O15036 O43165 | BAA20780 | NP_175982 | XP_084941 | BAA74919 |
| O43584 | T39585 | AAF68076 | AAH15380 | BAB24805 |
| O94970 | NP_060239 | AAF68077 | XP_080159 | BAB30794 |
| O95071 | T39007 | AAH11571 | AAF08298 | NP_004229 |
| O95714 | BAA92539 | XP_052430 | BAA19217 | O08759 |
| Q15386 | CAC42101 | AAF68079 | T01491 | AAH19345 |
| Q15751 | XP_083009 | AAH04712 | CAB92704 | NP_011374 |
| Q96BP4 | AAF79338 | T38951 | CAB09785 | NP_056092 |
| Q96CZ2 | NP_060382 | BAA23711 | NP_177189 | AAH21144 |
| | | BAB13451 | | |

TABLE 3-continued

| | | | | |
|---|---|---|---|---|
| Q96DE7 | AAH00621 | AAF46512 | XP_030186 | NP_056986 |
| Q96F34 | AAH09271 | NP_000453 | AAF61856 | B38919 |
| Q96F66 | AAC62434 | AAL29143 | XP_057408 | T38617 |
| Q96GR7 | AAF51314 | AAL27259 | Q9PUN2 | AAH06848 |
| Q96J02 | T21546 | AAF36539 | CAB99103 | NP_490834 |
| Q96PU5 | NP_188346 | BAA84697 | NP_195908 | NP_010745 |
| Q9BUI0 | AAF49328 | NP_499392 | AAH11391 | CAB95249 |
| Q9BUI6 | XP_082286 | AAF68080 | NP_012570 | |
| Q9BVR2 | NP_035020 | I83196 | AAF52899 | |
| Q9BXZ4 | NP_501120 | NP_057407 | AAF88143 | |
| Q9BY75 | NP_055636 | AAF28950 | AAF68614 | |
| Q9H0M0 | NP_003913 | XP_052223 | BAA20771 | |
| Q9H2G0 | BAB02722 | AAF68082 | BAB13419 | |
| Q9H2W4 | NP_497697 | AAF68083 | NP_011051 | |
| Q9H451 | NP_490865 | T41750 | AAH13645 | |
| Q9H783 | T14761 | AAH11658 | Q9CUN6 | |
| Q9H9E9 | AAC83345 | NP_114087 | XP_046129 | |
| Q9HCC7 | S70642 | Q05086 | A38920 | |
| Q9HCH9 | AAG53076 | T49744 | AAB47756 | |
| Q9NPL3 | CAA03915 | AAC51324 | Q92462 | |
| Q9NPS9 | XP_085770 | BAA92571 | NP_113671 | |
| Q9NY88 | CAC09387 | BAB30733 | CAA57291 | |
| Q9NWS4 | NP_055421 | NP_500283 | XP_087357 | |
| Q9NXC0 | NP_523779 | AAK28419 | AAC41731 | |
| Q9NZS4 | XP_038999 | NP_446441 | BAB69424 | |
| Q9P0A9 | AAD51453 | BAA86445 | T37900 | |
| Q92PL3 | AAB49301 | NP_190877 | T14317 | |
| Q9P2M6 | T49799 | Q9HCE7 | P51593 | |
| Q9P2P5 | AAG16783 | AAF50332 | AAH04085 | |
| Q9UDU3 | NP_195572 | AAH09527 | BAA21482 | |
| Q9UFZ7 | AAH21470 | NP_490750 | NP_012915 | |
| Q9UII4 | NP_078878 | XP_003492 | AAF48495 | |
| Q9ULT8 Q9Y4D8 | NP_073576 | T37736 | XP_045232 | |
| Q9HAU4 | XP_028151 | AAF47474 | AAF50913 | |
| Q9HCE7 | P49634 | AAD34642 | T00390 | |
| P46934 | BAB28001 | | NP_476753 | |
| Q05086 | NP_004658 | | T46412 | |
| Q14669 | P46935 | | XP_045095 | |
| Q15034 | NP_524296 | | NP_113584 | |
| | | | NP_495842 | |
| | | | AAC04845 | |
| | | | XP_030175 | |
| | | | 1C4Z | |

Ringfinger domain proteins
(Ensembl data base)

| | | | |
|---|---|---|---|
| ENSP00000259945 | ENSP00000282135 | ENSP00000255977 | ENSP00000265742 |
| ENSP00000254436 | ENSP00000280460 | ENSP00000283460 | ENSP00000269475 |
| ENSP00000066988 | ENSP00000280461 | ENSP00000262370 | ENSP00000265290 |
| ENSP00000275736 | ENSP00000217740 | ENSP00000253024 | ENSP00000222597 |
| ENSP00000275735 | ENSP00000227588 | ENSP00000282369 | ENSP00000292307 |
| ENSP00000203439 | ENSP00000259944 | ENSP00000253571 | ENSP00000265267 |
| ENSP00000013772 | ENSP00000279757 | ENSP00000288913 | ENSP00000263220 |
| ENSP00000225283 | ENSP00000274773 | ENSP00000288918 | ENSP00000216225 |
| ENSP00000246907 | ENSP00000276311 | ENSP00000276573 | ENSP00000293538 |
| ENSP00000225285 | ENSP00000166144 | ENSP00000237308 | ENSP00000229766 |
| ENSP00000225286 | ENSP00000292363 | ENSP00000238203 | ENSP00000242239 |
| ENSP00000230239 | ENSP00000264616 | ENSP00000227451 | ENSP00000274616 |
| ENSP00000286909 | ENSP00000272390 | ENSP00000244360 | ENSP00000286773 |
| ENSP00000286910 | ENSP00000272396 | ENSP00000244359 | ENSP00000273480 |
| ENSP00000280609 | ENSP00000264767 | ENSP00000281105 | ENSP00000217173 |
| ENSP00000263651 | ENSP00000255499 | ENSP00000268907 | ENSP00000290337 |
| ENSP00000261395 | ENSP00000264614 | ENSP00000292962 | ENSP00000281930 |
| ENSP00000277584 | ENSP00000262482 | ENSP00000280804 | ENSP00000257575 |
| ENSP00000224833 | ENSP00000261481 | ENSP00000287546 | ENSP00000287212 |
| ENSP00000254604 | ENSP00000261658 | ENSP00000248980 | ENSP00000290788 |
| ENSP00000240395 | ENSP00000288774 | ENSP00000287559 | ENSP00000282455 |
| ENSP00000240318 | ENSP00000261675 | ENSP00000264926 | ENSP00000254247 |
| ENSP00000286945 | ENSP00000266880 | ENSP00000261737 | ENSP00000290649 |
| ENSP00000281874 | ENSP00000243674 | ENSP00000170447 | ENSP00000274542 |
| ENSP00000240802 | ENSP00000284638 | ENSP00000270944 | ENSP00000224994 |
| ENSP00000267825 | ENSP00000247668 | ENSP00000289726 | ENSP00000281418 |
| ENSP00000254586 | ENSP00000285317 | ENSP00000230099 | ENSP00000289883 |
| ENSP00000293123 | ENSP00000278480 | ENSP00000237455 | ENSP00000255325 |
| ENSP00000285805 | ENSP00000240159 | ENSP00000263550 | ENSP00000255326 |
| ENSP00000257633 | ENSP00000294256 | ENSP00000264198 | ENSP00000292543 |
| ENSP00000266119 | ENSP00000279766 | ENSP00000263464 | ENSP00000277534 |
| ENSP00000233630 | ENSP00000288204 | ENSP00000259604 | ENSP00000260947 |

TABLE 3-continued

| | | | |
|---|---|---|---|
| ENSP00000264033 | ENSP00000269439 | ENSP00000265673 | ENSP00000278455 |
| ENSP00000275619 | ENSP00000268061 | ENSP00000248983 | ENSP00000278454 |
| ENSP00000275637 | ENSP00000268058 | ENSP00000269391 | ENSP00000274694 |
| ENSP00000280063 | ENSP00000268059 | ENSP00000249007 | ENSP00000217740 |
| ENSP00000276333 | ENSP00000268060 | ENSP00000242719 | ENSP00000262952 |
| ENSP00000263651 | ENSP00000261825 | ENSP00000217169 | ENSP00000268154 |
| ENSP00000278302 | ENSP00000288587 | ENSP00000253642 | ENSP00000265756 |
| ENSP00000264122 | ENSP00000275693 | ENSP00000227758 | ENSP00000277490 |
| ENSP00000284559 | ENSP00000244061 | ENSP00000291190 | ENSP00000266625 |
| ENSP00000266252 | ENSP00000272598 | ENSP00000261537 | ENSP00000266624 |
| ENSP00000278350 | ENSP00000289818 | ENSP00000291733 | ENSP00000258147 |
| ENSP00000259847 | ENSP00000238349 | ENSP00000274782 | ENSP00000258148 |
| ENSP00000274855 | ENSP00000280266 | ENSP00000271787 | ENSP00000258149 |
| ENSP00000259930 | ENSP00000242855 | ENSP00000261445 | ENSP00000264512 |
| ENSP00000217214 | ENSP00000276688 | ENSP00000245836 | ENSP00000261212 |
| ENSP00000283330 | ENSP00000280268 | ENSP00000267291 | ENSP00000262642 |
| ENSP00000263535 | ENSP00000274811 | ENSP00000292195 | ENSP00000264359 |
| ENSP00000291416 | ENSP00000268363 | ENSP00000216420 | ENSP00000217537 |
| ENSP00000291414 | ENSP00000274828 | ENSP00000261464 | ENSP00000264777 |
| ENSP00000253769 | ENSP00000235150 | ENSP00000260076 | ENSP00000287880 |
| ENSP00000274786 | ENSP00000211960 | ENSP00000284244 | ENSP00000272674 |
| ENSP00000289896 | ENSP00000262843 | ENSP00000292545 | ENSP00000272662 |
| ENSP00000289898 | ENSP00000266952 | ENSP00000242669 | ENSP00000293245 |
| ENSP00000265771 | ENSP00000288300 | ENSP00000288848 | ENSP00000283875 |
| ENSP00000229866 | ENSP00000291134 | ENSP00000261809 | ENSP00000262642 |
| ENSP00000286475 | ENSP00000261947 | ENSP00000262952 | ENSP00000259865 |
| ENSP00000256257 | ENSP00000288715 | ENSP00000245937 | ENSP00000217908 |
| ENSP00000253554 | ENSP00000222704 | ENSP00000275970 | ENSP00000255004 |
| ENSP00000259654 | ENSP00000293938 | ENSP00000238647 | ENSP00000275184 |
| ENSP00000280266 | ENSP00000266030 | ENSP00000268850 | ENSP00000275183 |
| ENSP00000259941 | ENSP00000287335 | ENSP00000291963 | ENSP00000200457 |
| ENSP00000259940 | ENSP00000256649 | ENSP00000286349 | ENSP00000261537 |
| ENSP00000270086 | ENSP00000249240 | ENSP00000257600 | ENSP00000257100 |
| ENSP00000289140 | ENSP00000253953 | ENSP00000281843 | ENSP00000286349 |
| ENSP00000225507 | ENSP00000267073 | ENSP00000261245 | ENSP00000252445 |
| ENSP00000261593 | ENSP00000271813 | ENSP00000245888 | ENSP00000294213 |
| ENSP00000257847 | ENSP00000248492 | ENSP00000222704 | ENSP00000259939 |
| ENSP00000262881 | ENSP00000265981 | ENSP00000245419 | ENSP00000236892 |
| ENSP00000222033 | ENSP00000270280 | ENSP00000272023 | ENSP00000238001 |
| ENSP00000290048 | ENSP00000270279 | ENSP00000274068 | ENSP00000274657 |
| ENSP00000274327 | ENSP00000254959 | ENSP00000275233 | ENSP00000274799 |

Sequences encoding a ubiquitin activating agent may also be used to make variants thereof that are suitable for use in the methods and compositions of the present invention. The ubiquitin ligating agents and variants suitable for use in the methods and compositions of the present invention may be made as described herein.

In a preferred embodiment, RING finger subunits include, but are not limited to, polypeptides having an amino acid sequence corresponding to Genbank accession numbers AAD30147, AAD30146, or 6320196, incorporated herein by reference. In a more preferred embodiment, the ring finger protein has a sequence selected from the group consisting of that shown in FIG. 8, FIG. 9 and FIG. 10B.

In a preferred embodiment, Cullins include, but are not limited to, polypeptides having an amino acid sequence corresponding to Genbank accession number 4503161, AAC50544, AAC36681, 4503163, AAC51190, AAD23581, 4503165, AAC36304, AAC36682, AAD45191, AAC50548, Q13620, 4503167, or AAF05751, each of which is incorporated herein by reference. In addition, in the context of the invention, each of the RING finger proteins and Cullins encompass variants of the known or listed sequences, as described herein.

In a preferred embodiment, the Cullin has a sequence as shown in FIG. 11B or 12B.

These E3 ligating agents and variants may be made as described herein. In a preferred embodiment, nucleic acids used to make the RING finger proteins include, but are not limited to, those having the nucleic acid sequences disclosed in Genbank accession numbers AF142059, AF142060 and nucleic acids 433493 to 433990 of NC 001136. In a preferred embodiment, Cullins are made from nucleic acids including, but not limited to, those having nucleic acid sequences disclosed in Genbank accession numbers NM 003592, U58087, AF062536, AF126404, NM 003591, U83410, NM 003590, AB014517, AF062537, AF064087, AF077188, U58091, NM 003478, X81882 and AF191337, each of which is incorporated herein by reference. As described above, variants of these sequences are also encompassed by the invention.

In a preferred embodiment, nucleic acid used to produce ROC2 comprises the sequence depicted in FIG. 12A. In a preferred embodiment, nucleic acid used to produce CUL5 comprises the sequence depicted in FIG. 13A. In a preferred embodiment, nucleic acid used to produce APC2 comprises the sequence depicted in FIG. 14A.

In a preferred embodiment, E3 comprises the RING finger protein/Cullin combination APC11/APC2. In another preferred embodiment, E3 comprises the RING finger protein/Cullin combination ROC1/CUL1. In yet preferred embodiment, E3 comprises the RING finger protein/Cullin combination ROC1/CUL2. In still another preferred embodiment, E3 comprises the RING finger protein/Cullin combination ROC2/CUL5. However, the skilled artisan will appreciate that any combination of E3 components may be produced and used in the invention described herein.

In an alternate embodiment, E3 comprises the ligase E3-alpha, E3A (E6-AP), HERC2, SMURF1, TRAF6, Mdm2, Cbl, Sina/Siah, Itchy, IAP or NEDD-4. In this embodiment, the ligase has the amino acid sequence of that disclosed in Genbank accession number AAC39845, Q05086, CAA66655, CAA66654, CAA66656, AAD08657, NP_002383, XP_006284, AAC51970, XP_013050, BAB39389, Q00987, AAF08298 or P46934, each of which is incorporated herein by reference. As above, variants are also encompassed by the invention. Nucleic acids for making E3 for this embodiment include, but are not limited to, those having the sequences disclosed in Genbank accession numbers AF061556, XM006284, U76247, XM013050, X898032, X98031, X98033, AF071172, Z12020, AB056663, AF199364 and D42055 and variants thereof.

E3 may also comprise other components, such as SKP1 and F-box proteins. The amino acid and nucleic acid sequences for SKP1 correspond to GENBANK accession numbers AAC50241 and U33760, respectively. Many F-box proteins are known in the art and their amino acid and nucleic acid sequences are readily obtained by the skilled artisan from various published sources.

In a preferred embodiment, the E3 components are produced recombinantly, as described herein. In a preferred embodiment, the E3 components are co-expressed in the same host cell. Co-expression may be achieved by transforming the cell with a vector comprising nucleic acids encoding two or more of the E3 components, or by transforming the host cell with separate vectors, each comprising a single component of the desired E3 protein complex. In a preferred embodiment, the RING finger protein and Cullin are expressed in a single host transfected with two vectors, each comprising nucleic acid encoding one or the other polypeptide, as described in further detail in the Examples.

In a preferred embodiment, E3 has a tag, and this complex is referred to herein as "tag-E3". Preferably, the tag is attached to only one component of the E3. Preferred E3 tags include, but are not limited to, labels, partners of binding pairs and substrate binding elements. More preferably, the tag is a surface substrate binding molecule. Most preferably, the tag is a His-tag or GST-tag.

Ubiquitin moieties, ubiquitin agents, and target molecules suitable for use in the methods and compositions of the present invention can be cloned and expressed as described below.

Thus, probe or degenerate polymerase chain reaction (PCR) primer sequences may be used to find other related or variant ubiquitin moieties, ubiquitin agents, and target proteins from humans or other organisms. As will be appreciated by those in the art, particularly useful probe and/or PCR primer sequences include the unique areas of a nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences cited herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant nucleic acid can be further-used as a probe to identify and isolate other nucleic acids. It can also be used as a "precursor" nucleic acid to make modified or variant nucleic acids and proteins.

Using the nucleic acids of the present invention which encode a protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading fram. However, enhancers do not have to be contiguous. Linking is accomplished by ligation at convenient restriction sites. If such sites do not exist, the synthetic oligonucleotide adapters or linkers are used in accordance with conventional practice. The transcriptional and translational regulatory nucleic acid will generally be appropriate to the host cell used to express the protein; for example, transcriptional and translational regulatory nucleic acid sequences from *Bacillus* are preferably used to express the protein in *Bacillus*. Numerous types of appropriate expression vectors, and suitable regulatory sequences are known in the art for a variety of host cells. In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

Proteins of the present invention are produced by culturing a host cell transformed with an expression vector containing nucleic acid encoding the protein, under the appropriate conditions to induce or cause expression of the protein. The conditions appropriate for protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melanogaster* cells, *Pichia pastoris* and *P. methanolica*, *Saccharomyces cerevisiae* and other yeasts, *E. coli, Bacillus subtilis*, SF9 cells, SF21 cells, C129 cells, Saos-2 cells, Hi-5 cells, 293 cells, Neurospora, BHK, CHO, COS, and HeLa cells. Of greatest interest are *Pichia pastoris* and *P. methanolica, E. coli*, SF9 cells, SF21 cells and Hi-5 cells.

In a preferred embodiment, the proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for a protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase 11 to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of a protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, proteins are produced in insect cells. Expression vectors for the transformation of insect cells, and in particular, baculovirus-based expression vectors, are well known in the art.

In a preferred embodiment, proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii P. methanolica* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The protein may also be made as a fusion protein, using techniques well known in the art. Thus, for example, the protein may be made as a fusion protein to increase expression, or for other reasons. For example, when the protein is a peptide, the nucleic acid encoding the peptide may be linked to other nucleic acid for expression purposes. Similarly, proteins of the invention can be linked to protein labels, such as green fluorescent protein (GFP), red fluorescent protein (RFP), blue fluorescent protein (BFP), yellow fluorescent protein (YFP), etc.

In a preferred embodiment, the protein is purified or isolated after expression. Proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the ubiquitin moiety protein may be purified using a standard anti-ubiquitin moiety antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the protein. In some instances no purification will be necessary.

Once made, the compositions find use in a number of applications, including, but not limited to, assaying for agents that modulate the activity of a ubiquitin agent. In particular, the compositions can be used to assay for agents that modulate the transfer or attachment of ubiquitin moiety to a substrate molecule. The term "modulate" as used herein with reference to the activity of a ubiquitin agent refers to the increase or decrease in an activity of a ubiquitin agent, for example, activating activity, conjugating activity, ligating activity, and more specifically the attachment of ubiquitin moiety to a substrate molecule. The term "attachment" as used herein with reference to the activity of a ubiquitin agent refers to the binding, transfer, or attachment of a ubiquitin moiety to a substrate molecule. The skilled artisan will appreciate that agents that modulate the activity of ubiquitin agents (or "modulators") may affect enzyme activity, enzyme interaction with a substrate, interaction between ubiquitin moiety and the substrate, or a combination of these.

By "candidate", "candidate agent", "candidate modulator", "candidate ubiquitination modulator" or grammatical equivalents herein is meant any candidate molecule, e.g. a protein (which herein includes a protein, polypeptide, and peptide), small organic or inorganic molecule, polysaccharide, or polynucleotide which are to be tested for the ability to modulate the activity of a ubiquitin agent, and more specifically, for the ability to modulate the attachment of ubiquitin moiety to a substrate molecule. Candidate agents encompass numerous chemical classes. In a preferred embodiment, the candidate agents are small molecules. In another preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate agents are obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

In a preferred embodiment, candidate agents are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate agent prior to the assay. Using the methods of the present invention, any candidate agents can be screened for the ability to increase or decease the activity of a ubiquitin agent, or more specifically for the ability to increase or decrease the attachment of ubiquitin moiety to a substrate. In addition, as is known in the art, coding tags using split synthesis reactions may be used to essentially identify the chemical moieties tested.

Alternatively, a preferred embodiment utilizes libraries of natural compounds, as candidate agents, in the form of bacterial, fungal, plant and animal extracts that are available or readily produced.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate agents include proteins, nucleic acids, and chemical moieties.

In a preferred embodiment, the candidate agents are proteins, as defined above. In a preferred embodiment, the candidate agents are naturally occurring proteins or fragments of naturally occurring proteins. Thus, for example, cellular extracts containing proteins, or random or directed digests of proteinaceous cellular extracts, may be tested, as is more fully described below. In this way libraries of prokaryotic and eukaryotic proteins may be made for screening against any number of candidate agents. Particularly preferred in this embodiment are libraries of bacterial, fungal, viral, and mammalian proteins, with the latter being preferred, and human proteins being especially preferred.

In a preferred embodiment, the candidate agents are peptides of from about 2 to about 50 amino acids, with from about 5 to about 30 amino acids being preferred, and from about 8 to about 20 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

The library should provide a sufficiently structurally diverse population of randomized agents to effect a probabilistically sufficient range of diversity to allow interaction with a particular ubiquitin ligating agent enzyme. Accordingly, an interaction library must be large enough so that at least one of its members will have a structure that interacts with a ubiquitin agents or other components of a ubiquitin reaction, for example, ubiquitin moiety or target protein. Although it is difficult to gauge the required absolute size of an inter action library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for a target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, when the candidate a gent is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from *Xenopus*, can have potent anti-tumor and anti-microbial activity. Short peptide fragments of a protein kinase C isozyme (βPKC), have been shown to block nuclear translocation of βPKC in *Xenopus* oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate modulators as well.

Thus, a number of molecules or protein domains are suitable as starting points for the generation of biased randomized candidate modulators. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, and Traf.

In a preferred embodiment, the candidate agents are nucleic acids. With reference to candidate agents, by 'nucleic acid' or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Left. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made. Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As described above generally for proteins, nucleic acid candidate agent may be naturally occurring nucleic acids, random nucleic acids, or "biased" random nucleic acids. For example, digests of prokaryotic or eukaryotic genomes may be used as is outlined above for proteins. Where the ultimate expression product is a nucleic acid, at least 10, preferably at least 12, more preferably at least 15, most preferably at least 21 nucleotide positions need to be randomized, with more preferable if the randomization is less than perfect. Similarly, at least 5, preferably at least 6, more preferably at least 7 amino acid positions need to be randomized; again, more are preferable if the randomization is less than perfect.

In a preferred embodiment, the candidate agents are organic moieties. In this embodiment, as is generally described in WO 94/24314, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As will be appreciated by those in the art, it is possible to screen more than one type of candidate agent at a time. Thus, the library of candidate agents used may include only one type of agent (i.e. peptides), or multiple types (peptides and organic agents). The assay of several candidates at one time is further discussed below.

The present invention provides methods and compositions comprising combining different combinations of ubiquitin agents, with ubiquitin moiety, in the presence or absence of a target protein. In preferred embodiments, a candidate agent is included in the combining to assay for an agent that modulates the attachment of a ubiquitin moiety to a substrate molecule. In preferred embodiments the ubiquitin moiety and/or the substrate molecule of interest in the assay comprises a tag.

Preferably the tag is a label, a partner of a binding pair, or a substrate binding molecule (or attachment tag). In a preferred embodiment, the tag is an epitope tag. In another preferred embodiment, the tag is a label. More preferably, the tag is a fluorescent label or a binding pair partner. In a preferred embodiment, the tag is a binding pair partner and the ubiquitin moiety is labeled by indirect labeling. In the indirect labeling embodiment, preferably the label is a fluorescent label or a label enzyme. In an embodiment comprising a label enzyme, preferably the substrate for that enzyme produces a fluorescent product. In a preferred embodiment, the label enzyme substrate is luminol. In a preferred embodiment, combining specifically excludes combining the components with a target protein.

In another preferred embodiments, a preferred combination is Tag1-ubiquitin moiety, tag2-ubiquitin moiety. Preferably, tag1 and tag2 are labels, preferably fluorescent labels, most preferably tag1 and tag2 constitute a FRET pair.

In a preferred embodiment, a preferred combination is tag1-ubiquitin moiety and tag2-substrate molecule of interest. Preferably, tag1 is a label, a partner of a binding pair, or a substrate binding molecule and tag2 is a different label, partner of a binding pair, or substrate binding molecule. More preferably, tag1 is a fluorescent label or a member of a binding pair. When tag1 is a member of a binding pair, preferably tag1 is indirectly labeled. Still more preferably, tag-1 is indirectly labeled with a label enzyme. Preferably the label enzyme substrate used to reveal the presence of the enzyme produces a fluorescent product, and more preferably is luminol. In the presently described combination, preferably tag2 is a surface substrate binding element, more preferably a His-tag.

In a preferred embodiment, the methods of the invention do not comprise a target protein. In a preferred embodiment, a mono- or poly-ubiquitin moiety is a substrate molecule, as discussed above. Because the different combinations of ubiquitin agents are specific for particular target proteins, the present assays are much more versatile then conventional assays which require a target protein. However, the activity of these ubiquitin agents can be assayed in the methods of the present invention because the methods permit the use of any variation of such combinations without first identifying the specific target protein to which the combination is directed.

The components of the present assays may be combined in varying amounts. In a preferred embodiment, ubiquitin moiety is combined at a final concentration of from 20 to 200 ng per 100 $\mu$l reaction solution, most preferable at about 100 ng per 100 $\mu$l reaction solution.

In a preferred embodiment, the ubiquitin activating agent, preferably an E1, is combined at a final concentration of from 1 to 50 ng per 100 $\mu$l reaction solution, more preferably from 1 ng to 20 ng per 100 $\mu$l reaction solution, most preferably from 5 ng to 10 ng per 100 $\mu$l reaction solution.

In a preferred embodiment, the ubiquitin conjugating agent, preferably an E2, is combined at a final concentration of 10 to 100 ng per 100 $\mu$l reaction solution, more preferably 10–50 ng per 100 $\mu$l reaction solution.

In a preferred embodiment, the ubiquitin ligating agent, preferably an E3, is combined at a final concentration of from 1 ng to 500 ng per 100 $\mu$l reaction solution, more preferably from 50 to 400 ng per 100 $\mu$l reaction solution, still more preferably from 100 to 300 ng per 100 $\mu$l reaction solution, and still more preferably about 100 ng per 100 $\mu$l reaction solution. In a preferred embodiment, the ubiquitin ligating agent is combined at a final concentration of from 50 to 100 ng per 100 $\mu$l reaction solution, still more preferably from 20 to 50 ng per 100 $\mu$l reaction solution, and still more preferably about 10 ng to 20 ng per 100 $\mu$l reaction solution.

The components of the present assays are combined under reaction conditions that favor the activity of the ubiquitin agents of the present invention, and more specifically favir the attachment of ubiquitin moiety to a substrate molecule of interest in the assay. Generally, this will be under physiological conditions. Incubations may be performed at any temperature which facilitates optimal activity, typically between 4 and 40° C. Incubation periods are selected for optimum activity, but may also be optimized to facilitate rapid high through put screening. Typically between 0.5 and 1.5 hours will be sufficient.

A variety of other reagents may be included in the compositions. These include reagents like salts, solvents, buffers, neutral proteins, e.g. albumin or detergents which may be used to facilitate optimal activity of ubiquitin agents, and more specifically facilitate the attachment of ubiquitin moiety to a substrate molecule of interest in the assay; and/or reduce non-specific or background interactions. Also reagents that otherwise improve the efficiency of the assay, such as protease inhibitors, nuclease inhibitors, anti-microbial agents, etc., may be used. The compositions will also preferably include adenosine tri-phosphate (ATP).

The mixture of components may be added in any order that promotes the activity ubiquitin agents, and more specifically promotes the attachment of ubiquitin moiety to a substrate molecule of interest in the assay; or optimizes identification of the modulating activity of a candidate agent. In a preferred embodiment, ubiquitin moiety is provided in a reaction buffer solution, followed by addition of the ubiquitin ubiquitination enzymes. In an alternate preferred embodiment, ubiquitin moiety is provided in a reaction buffer solution, a candidate agent is then added, followed by the addition of ubiquitin agents.

Once combined, in a preferred embodiment, the amount of ubiquitin moiety attached to a substrate molecule of interest in an assay of the present invention, is measured. As will be understood by one of ordinary skill in the art, the mode of measuring may depend on the specific tag attached to the ubiquitin moiety. As will also be apparent to the skilled artisan, the amount of ubiquitin moiety attached to a substrate molecule will encompass not only the particular ubiquitin moiety bound directly to the substrate molecule, but also a mono- or poly-ubiquitin moiety preferably attached to the substrate molecule.

In a preferred embodiment, the tag attached to the ubiquitin moiety is a fluorescent label. In a preferred embodiment, the tag attached to ubiquitin moiety is an enzyme label or a binding pair member which is indirectly labeled with an enzyme label. In this latter preferred embodiment, the enzyme label substrate produces a fluorescent reaction product. In these preferred embodiments, the amount of ubiquitin moiety bound is measured by luminescence.

In other preferred embodiments, at least a first and a second ubiquitin moiety is used, wherein the first and second ubiquitin moieties comprise different fluorescent labels, and wherein the labels form a FRET pair.

As used herein, "luminescence" or "fluorescent emission" means photon emission from a fluorescent label. In an embodiment where FRET pairs are used, fluorescence measurements may be taken continuously or at time-points during the ligation reaction. Equipment for such measurement is commercially available and easily used by one of ordinary skill in the art to make such a measurement.

Other modes of measuring the attachment of ubiquitin moiety to a substrate molecule of are well known in the art and easily identified by the skilled artisan for each of the labels described herein. For example, radioisotope labeling may be measured by scintillation counting, or by densitometry after exposure to a photographic emulsion, or by using a device such as a Phosphorimager. Likewise, densitometry may be used to measure the attachment of ubiquitin moiety following a reaction with an enzyme label substrate that produces an opaque product when an enzyme label is used.

In a preferred embodiment, the substrate molecule of interest in the assays of the present invention is bound to a surface substrate. This may be achieved a s described above for the binding of a label to ubiquitin moiety.

In another preferred embodiment, a ubiquitin activating agent is bound to a surface substrate in the absence of a ubiquitin conjugating agent and ubiquitin ligating agent. This may be achieved, as described above for the binding of a label to ubiquitin moiety. This may also be accomplished using tag-ubiquitin activating agent, wherein the tag is a surface substrate binding molecule.

In another preferred embodiment, a ubiquitin conjugating agent is bound to a surface substrate in the absence of a ubiquitin ligating agent. This may be achieved, as described above for the binding of a label to ubiquitin moiety. This may also be accomplished using tag-ubiquitin conjugating agent, wherein the tag is a surface substrate binding molecule.

In another preferred embodiment, a ubiquitin ligating agent is bound to a surface substrate in the absence of a target protein. This may be achieved, as described above for the binding of a label to ubiquitin moiety. This may also be accomplished using tag-ubiquitin ligating agent, wherein the tag is a surface substrate binding molecule.

In general, any substrate binding molecule can be used. In a preferred embodiment, the tag is a His-tag and the surface substrate is nickel. In a preferred embodiment, the nickel surface substrate is present on the surface of the wells of a multi-well plate, such as a 96 well plate. Such multi-well plates are commercially available. The binding of the enzyme to a surface substrate facilitates the separation of bound ubiquitin moiety from unbound ubiquitin moiety. In the present embodiment, the unbound ubiquitin moiety is easily washed from the receptacle following the ligation reaction. As will be appreciated by those of skill in the art, the use of any surface substrate binding element and receptacle having the surface substrate to which it binds will be effective for facilitating the separation of bound and unbound ubiquitin moiety.

In an alternative embodiment, the substrate molecule of interest in the assays of the present invention comprise a bead that is attached to the substrate molecule directly or via a substrate binding element. Following ligation, the beads may be separated from the unbound ubiquitin moiety and the bound ubiquitin moiety measured. In a preferred embodiment, the substrate molecule of interest in the assay of the present invention comprises a bead and the ubiquitin agents in the assay are combined with a tag-ubiquitin moiety wherein the tag is a fluorescent label. In this embodiment, the beads with bound ubiquitin moiety may be separated using a fluorescence-activated cell sorting (FACS) machine. Methods for such use are described in U.S. patent application Ser. No. 09/047,119, which is hereby incorporated in its entirety. The amount of bound ubiquitin moiety can then be measured.

In another embodiment, none of the ubiquitin agents are bound to a surface substrate. Preferably in this embodiment, the assays comprise a tag 1-ubiquitin moiety and tag2-ubiquitin moiety. Preferably, tag1 and tag2 are labels, preferably fluorescent labels, most preferably tag1 and tag2 constitute a FRET pair. In this embodiment, the attachment of ubiquitin moiety to the substrate molecule of interest is measured by measuring the fluorescent emission spectrum. This measuring may be continuous or at one or more times following the combination of the components. Alteration in the fluorescent emission spectrum of the combination as compared with unligated ubiquitin moiety indicates the amount of ubiquitin ubiquitination. The skilled artisan will appreciate that in this embodiment, alteration in the fluorescent emission spectrum results from ubiquitin moiety bearing different members of the FRET pair being brought into close proximity, either through the formation of polyubiquitin moiety and/or by binding nearby locations on a protein, preferably a target protein.

In one preferred embodiment of the present methods, the ubiquitin ligating agent is an MdM2 protein and comprises a first FRET label and the ubiquitin moiety comprises a second FRET label. In another embodiment, the MdM2 protein comprises an attachment tag. In another embodiment, the MdM2 protein is preferably provided on a solid support, and more preferably the solid support comprises a microtiter plate or a bead. In another embodiment, the mdm2 protein is preferably a mammalian mdm2 and more preferably a human mdm2.

In another preferred embodiment, the target protein is p53 and comprises a first FRET label and the ubiquitin moiety comprises a second FRET label.

In another embodiment, the p53 protein preferably comprises an attachment tag. In another embodiment, the p53 protein is preferably provided on a solid support, and more preferably the solid support comprises a microtiter plate or a bead.

In a preferred embodiment, the compositions of the invention are used to identify agents that modulate the attachment of ubiquitin moiety to a substrate molecule. In this embodiment, the composition includes a candidate agent. In a preferred embodiment, the measured amount and/or rate of tag-ubiquitin moiety binding to the substrate molecule is compared with the that when the candidate agent is absent from the composition, whereby the presence or absence of the agent's effects on the attachment of ubiquitin moiety to a substrate molecule is determined. In this embodiment, whether the agent enhances or inhibits, or reduces or increases the attachment of ubiquitin moiety to the substrate molecule is determined.

In a preferred embodiment, the composition of the invention containing a candidate agent lacks E3 and the amount and/or rate of ubiquitin moiety attached to E2 is measured. This embodiment may also comprise the step of comparing the amount and/or rate of ubiquitin moiety attached to E2 in a composition lacking both E3 and a candidate agent, whereby the modulating activity of the candidate agent is determined. In a preferred embodiment, the percentage difference in the amount of ubiquitin moiety attached to E2 in the presence and absence of the candidate agent is compared with the percentage difference in the amount attached to E3 in the presence and absence of candidate agent, whereby the point of effect of the candidate agent in the cascade of enzymatic activity and attachment of ubiquitin moiety to a substrate molecule is determined. That is, it is determined whether the candidate agent affects the attachment of ubiquitin moiety to E1, E2, and/or E3.

In another preferred embodiment, the compositions of the invention are used to identify agents that modulate the attachment of ubiquitin moiety to a substrate molecule of interest in the assay. In this embodiment, the present assays include a candidate agent. In a preferred embodiment, where tag1 and tag2 constitute a FRET pair, the measured amount and/or rate of tag1-ubiquitin moiety and tag2-ubiquitin moiety binding to a substrate molecule (as a poly-ubiquitin moiety and/or ubiquitin moiety attached to a substrate molecule) is compared with the amount or rate of such attachment in the absence of the candidate agent, whereby the presence or absence of the candidate agent's effect on the attachment of ubiquitin moiety to a substrate molecule is determined. In this embodiment, whether the candidate agent enhances or inhibits, or increases or decreases, the attachment of ubiquitin moiety to the substrate molecule is also determined.

In a preferred embodiment, multiple assays are performed simultaneously in a high throughput screening system. In this embodiment, multiple assays may be performed in multiple receptacles, such as the wells of a 96 well plate or other multi-well plate. As will be appreciated by one of skill in the art, such a system may be applied to the assay of multiple candidate agents and/or multiple combinations of ubiquitin agents with ubiquitin moiety. In a preferred embodiment, the present invention is used in a high-throughput screening system for determining the attachment of ubiquitin moiety to a substrate molecule of interest, by combining different combinations of ubiquitin agents, in the presence or absence of a target protein. In an alternate preferred embodiment, the present invention is used in a high throughput screening system for simultaneously testing the effect of individual candidate agents by additionally combinining a candidate agent.

In another aspect, the invention provides a method of assaying for the attachment of a ubiquitin moiety to a substrate molecule of in a mixture. Ubiquitin moiety is introduced into a cell or mixture of protein, preferably a cell lysate, under conditions in which the attachment of ubiquitin moiety to a substrate molecule of interest can take place. In this embodiment, the ubiquitin moiety is in the form of tag1-ubiquitin moiety and tag2-2-ubiquitin moiety, wherein tag1 and tag2 constitute a FRET pair or tag1 is a fluorescent label and tag2 is a quencher of tag1. Fluorescent emission spectrum is measured as an indication of whether ubiquitin ubiquitination activity is present in the mixture or cell. In a preferred embodiment, the ubiquitin moiety also comprises a member of a binding pair, such as FLAG. In this latter embodiment, components involved in ubiquitin ubiquitination can be isolated from the mixture using any one of a number of affinity-based separation means such as fluorescent beads coated with anti-FLAG antibody or amino precipitation using anti-FLAG antibodies, or using anti-FLAG antibody attached to a solid support. Other means of separating ubiquitin moiety attached components of the cell or mixture will be readily apparent to the skilled artisan. Ubiquitin moiety attached components so separated in this method may include ubiquitin agents and target proteins. The skilled artisan will appreciate that separation of these components for individual identification or subsequent investigation may be obtained by several means well known in the art, such as by HPLC or electrophoresis.

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, blocking steps, etc.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Example 1

Production of E2, E3, and Ubiquitin Moiety

E2 Production

The open reading frame of E2 (Ubch5c) was amplified by PCR and cloned into the pGex-6p-1 E.Coli. expression vector (Amersham Pharmacia) as BglII-EcoRI fragments, with N-terminus in frame fused to the GST-tag.

Materials and Methods

Plasmid is transformed in BL21 DE3 competent E.coli (Stratagene, cat #230132). Cells are grown at 37° C. in TB+100 ug/ml ampicillin and 0.4% glucose to an OD600 of about 0.6, induced with addition of 320 uM IPTG and allowed to grow for another 3 h before harvest. The pellets are washed once with cold PBS, then resuspended in about 6 volumes of lysis buffer (20 mM Tris, 10% glycerol, 0.5 M Nacl, 2.5 mM EDTA, 1 mM TCEP plus Complete-EDTA Free Protease inhibitor tablets, 1 tablet/25 ml of resuspended cells, pH 8.0). The suspension is homogenized and sonicated 3×30 sec. NP40, then added to a final concentration of 0.5% and the tubes are rocked for 30 min at 4° C. Following centrifugation at 11000 rpm for 25 to 30 min, the supernatant is incubated with Glutathione Sepharose 4B (Amersham, cat #17-0756-01) at a ratio of 1 ml of beads per 100 ml of original culture volume for 1 to 2 hours at 4° C. with gentle rocking. The beads are pelleted and washed once with 10 bed volumes of the lysis buffer, then twice with 10 bed volumes of Prescission Protease buffer (50 mM Tris-HCL, 150 mM NaCl, 1 mM EDTA, 1 mM DTT, 0.1% NP-40, pH 7.0.). Prescission Protease (Amersham, product #27-0843) is added at a ratio of 80 ul (160 Units) per ml of GST resin, and allowed to incubate for 4 h at 4° C. The supernatant containing the cleaved E2 protein is collected, and the resin is washed twice with one bed volume of Prescission buffer. All three fractions are analyzed by SDS-PAGE and pooled when appropriate.

Ubiquitin Moiety Production

Ubiquitin moiety was cloned into the pFlag-Mac Expression Vector (Sigma) as a HindIII-EcoRI fragment by PCR. This results in expression of amino-terminal Flag fusion ubiquitin moiety in E.Coli.

Materials and Methods

The induction of protein expression and cell lysis is similar to the above GST-E2 preparation, except that the supernatant is loaded over a FLAG-affinity resin (VWR, cat #IB 13020) at a ratio of 15 ml of beads per 1 L of original culture. The resin is then washed with 10 bed volumes of lysis buffer. The protein is eluted from the column with: 100 mM Acetic acid, 10% glycerol, 200 mM NaCl, 2.5 mM EDTA, 0.1% NP-40, pH 3.5. The elutions are collected as 1 bed volume fractions into tubes that contain 1/10th volume of 2M Tris, 80 mM B-ME, pH 9.0 to neutralize the pH. The elution fractions are analyzed by SDS-PAGE and the appropriate fractions are pooled and dialyzed against 400 volumes of 20 mM Tris, 10% glycerol, 200 mM NaCl, 2.5 mMEDTA, pH 8.0.

Production of E3

Coding sequences for E3 complex were also amplified by PCR and baculoviruses were generated using the Bac-to-Bac system (GibcoBRL). E3 contains two subunits, which are expressed by co-infection of the two baculovirus in the same Hi-5 insect cells. One of the subunit is His-tagged, with the other associating subunit untagged. The detail procedure was done following the Bac to Bac Baculovirus Expression system by GibcoBRL. For example, ROC1 was cloned into the pFastBacHtb vector with a N-terminal His6-tag, while CUL1 was insert into the pFastBacl vector without any fusing tag. After transposition and Bacmid DNA transfection into SF-9 cells, Baculoviruses were harvested, amplified, and used to co-infect Hi-5 cells for protein expression.

Materials and Methods

Cells are harvested, washed once with cold PBS, and resuspended in about 6 volumes of lysis buffer (20 mM Tris, 20% glycerol, 0.5 M Nacl, 15 mM imidazole, 1 mM TCEP plus Complete-EDTA Free Protease inhibitor tablets, 1 tablet/25 ml of resuspended cells, pH 8.0.). The suspension is then sonicated 3×30 sec, followed by addition of NP40 to a final concentration of 0.5% and incubation for 30 min at 4° C. The lysate is then centrifuged and the supernatant is incubated with pre-equilibrated (lysis buffer+NP40) Ni-NTA Agarose beads (Qiagen, cat #1000632) for 1 to 2 hrs. The pelleted beads are washed 2 times with lysis buffer, resuspended in 1 to 2 volumes of lysis buffer and transferred to a disposable column for elution. Elution is accomplished using 5×1-bed volume aliquots of Lysis buffer+250 mM imidazole. Elution fractions are analyzed by SDS-PAGE and appropriate fractions are pooled. The elution pool is then desalted using either a desalting column or a centrifugal concentration device (more often used for large volumes.) When using centrifugal devices, the eluted pool is diluted 1:1 with lysis buffer that has no imidazole and spun at the appropriate speed until the volume is reduced by half. At this point an equal volume of fresh buffer is added and the device is respun. This is done a total of four times resulting in a 32 fold exchange.

Example 2

E1+E2 Assay

The attachment of ubiquitin moiety to an E2, by combining E1+E2 and ubiquitin moiety, was assayed using the following protocol with Flag-ubiquitin, purified from E. coli, and the E2 Ubch5c, purified as His-Ubch5c from E. coli.

Materials and Methods

The following procedures were used for assays measuring the attachment of ubiquitin moiety to E2. The wells of Nickel-substrate 96-well plates (Pierce Chemical) are blocked with 100 µl of 1% casein/phosphate buffered saline (PBS) for 1 hour at room temperature, then washed with 200 µl of PBST (0.1% Tween-20 in PBS) 3 times. To each well is added the following Flag-ubiquitin moiety (see above) reaction solution:

Final Concentration 62.5 mM Tris pH 7.5
6.25 m $MgCl_2$
0.75 mM DTT
2.5 mM ATP
2.5 mM NaF
12.5 nM Okadaic acid
100 ng Flag-ubiquitin moiety (made as described above).

The buffer solution is brought to a final volume of 80 µl with milipore-filtered water, followed by the addition of 10 µl of DMSO.

To the above solution is then added 10 µl of E1,His-E2 in 20 mM Tris buffer, pH 7.5, and 5% glycerol. His-E2 is made as described above. E1 is obtained commercially (Affiniti Research Products, Exeter, U.K.). The following amounts of each enzyme are used for these assays: 5 ng/well of E1; 25 nl/well E2. The reaction is then allowed to proceed at room temperature for 1 hour.

Following the ubiquitin reaction, the wells are washed with 200 µl of PBST 3 times. For measurement of the E2-attached ubiquitin moiety, 100 µl of Mouse anti-Flag (1:10,000) and ant-Mouse Ig-HRP (1:15,000) in PBST are added to each well and allowed to incubate at room temperature for 1 hour. The wells are then washed with 200 µl of PBST 3 times, followed by the addition of 100 µl of luminol substrate (1/5 dilution). Luminescence for each well is then measured using a fluorimeter.

Results

Attachment of Ubiquitin Moiety to E1 and Attachment of Ubiquitin Moiety to E2

FIG. 1A shows the luminescence measured for E1 alone and for E1+his-E2, as described above.

Example 3

E1+E2+E3 Assay

The attachment of ubiquitin moiety to E3, by combining E1+E2+E3 and ubiquitin moiety, was assayed using the following protocol with Flag-ubiquitin, purified from *E. coli*, the E2 Ubch5c, purified as GST-Ubch5c from *E. coli* with the GST tag removed, and the E3 His-ROC1/Cul1 complex purified from Hi-5 cells by Baculovirus co-infection. This assay was also used to show the effects of candidate agents on the attachment of ubiquitin moiety to E3.

Materials and Methods

The wells of Nickel-substrate 96-well plates (Pierce Chemical) are blocked with 100 µl of 1 casein/phosphate buffered saline (PBS) for 1 hour at room temperature, then washed with 200 µl of PBST (0.1% Tween-20 in PBS) 3 times. To each well is added the following Flag-ubiquitin moiety (see above) reaction solution:

Final Concentration
62.5 mM Tris pH 7.5
6.25 m $MgCl_2$
0.75 mM DTT
2.5 mM ATP
2.5 mM NaF
12.5 nM Okadaic acid
100 ng Flag-ubiquitin moiety (made as described above).

The buffer solution is brought to a final volume of 80 µl with milipore-filtered water.

For assays directed to identifying agents that modulate the attachment of ubiquitin moiety to E3, 10 µl of a candidate agent in DMSO is then added to the solution. If no candidate agent is added, 10 µl of DMSO is added to the solution.

To the above solution is then added 10 µl containing the ubiquitin agents in 20 mM Tris buffer, pH 7.5, and 5% glycerol. E2-Ubch5c and E3-H is ROC1/Cul1 are made as described above. E1 is obtained commercially (Affiniti Research Products, Exeter, U.K.). The following amounts of each enzyme are used for these assays: 5 ng/well of E1; 25 nl/well E2; and 100 ng/well His-E3. The reaction is then allowed to proceed at room temper ature for 1 hour.

Following the ubiquitin ubiquitination reaction, the wells are washed with 200 µl of PBST 3 times. For measurement of the E3-attached ubiquitin moiety, 100 µl of Mouse anti-Flag (1:10,000) and ant-Mouse 1 g-HRP (1:15,000) in PBST are added to each well and allowed to incubate at room temperature for 1 hour. The wells are then washed with 200 µl of PBST 3 times, followed by the addition of 100 µl of luminol substrate (1/5 dilution). Luminescence for each well is then measured using a fluorimeter.

Results

Attachment of Ubiquitin Moiety to E3

Figure 2:
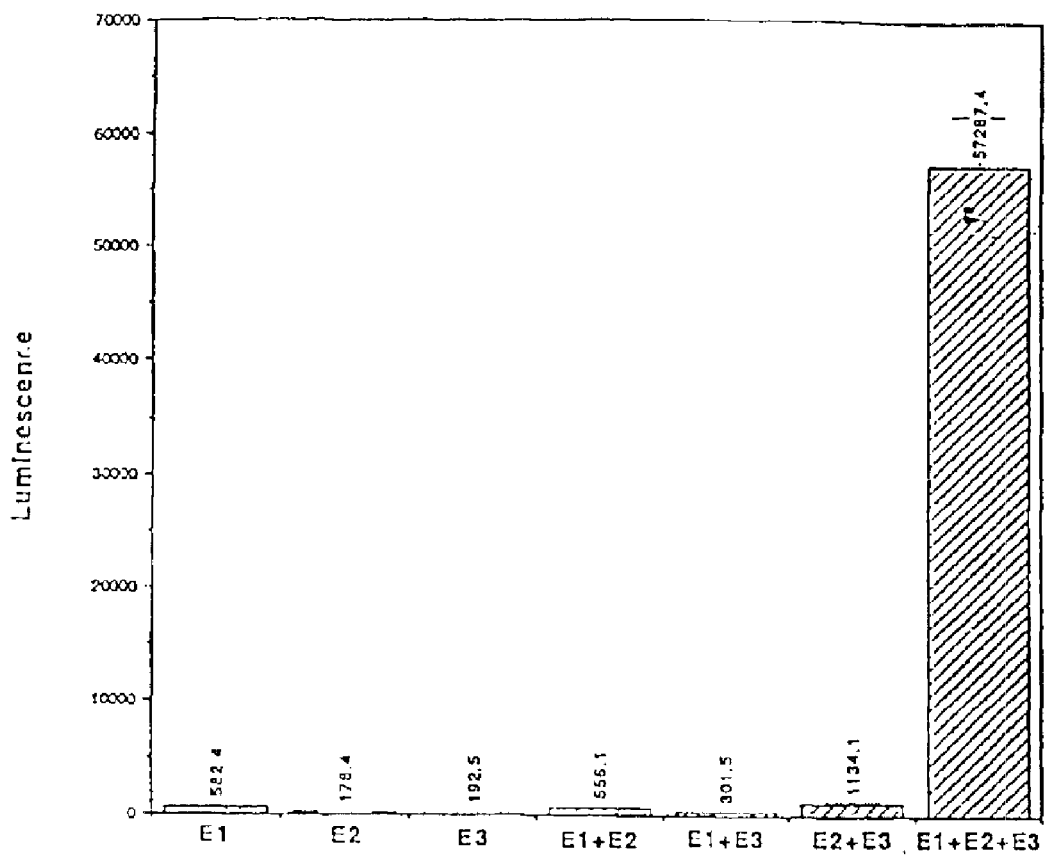
FIG. 2 shows the relative amounts of attachment of ubiquitin moiety to an E3 resulting from various combinations of ubiquitin agents and ubiquitin moiety. In these experiments, E3 comprises the RING finger protein ROC1 and the Cullin Cul1.

FIG. 2 shows the luminescence measured for several different combinations of ubiquitin agents. In these experiments, only E3 was in the form His-E3. The luminescence measurements show that the assay specifically measures the activity of the entire cascade of activity or attachment of ubiquitin moiety by the ubiquitin agents, which requires the presence of all three ubiquitin agents (i.e., E1+E2+E3) in this reaction.

Varying the Amounts of Ubiquitin Agents

Figure 3A:
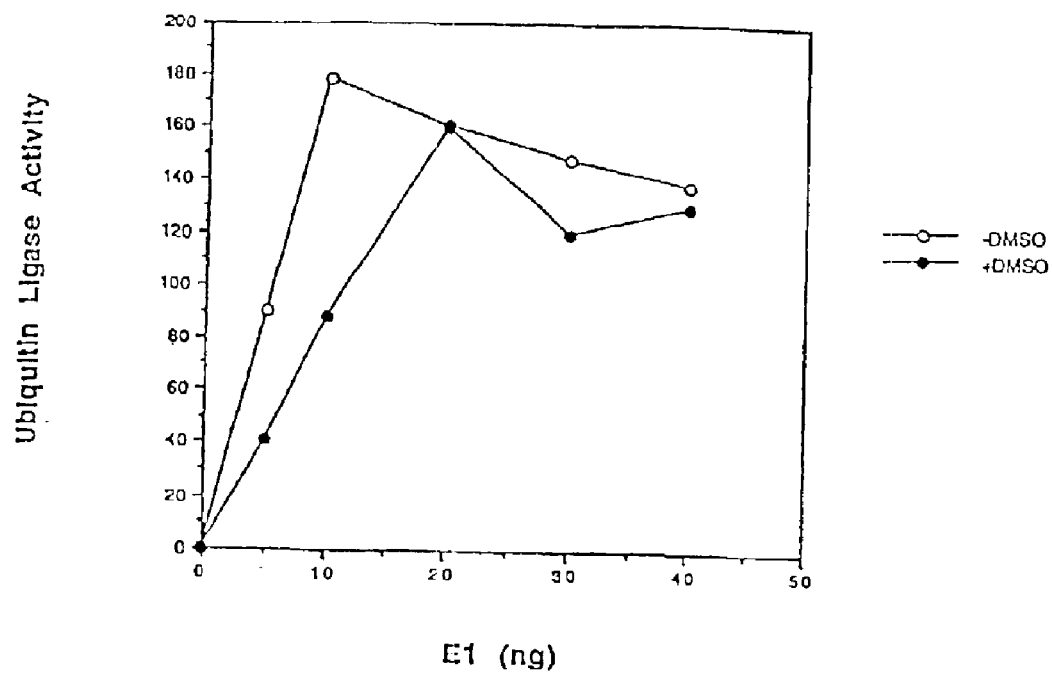
FIG. 3A shows relative amounts of attachment of ubiquitin moiety to an E3 using varying amounts of E1 in the presence and absence of DMSO.

FIG. 3A shows the relative effect of varying the amount of E1 on the attachment of ubiquitin moiety to E3 in the above procedure, in presence and absence of DMSO. The addition of about 10 ng per 100 µl reaction solution provides maximum amounts of attachment of ubiquitin moiety to E3 with the other components of the reaction maintained as detailed above. The presence of DMSO does not significantly affect the activity of the ubiquitin agents.

Figure 3B:
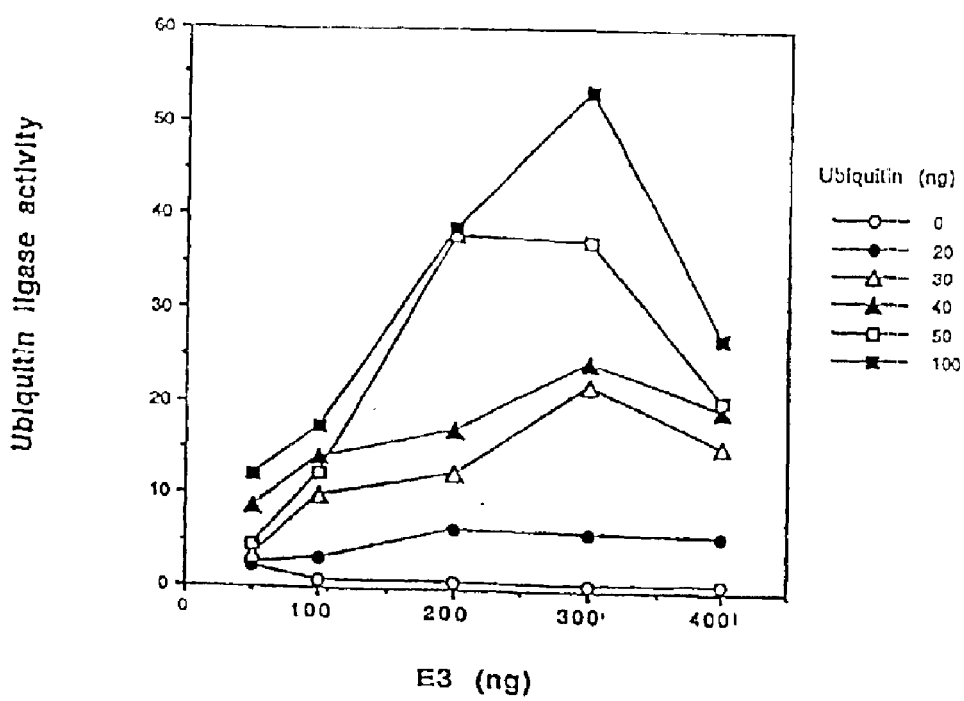
FIG. 3B shows relative amounts of attachment of ubiquitin moiety to an E3 using varying amounts of ubiquitin moiety and E3.

The relative effect of varying E3 and ubiquitin moiety concentration in the ubiquitin reaction is shown in FIG. 3B. Generally speaking, maximum amounts of attachment of ubiquitin moiety to E3 was obtained with 200 to 300 ng per 100 µl of E3 at each concentration of ubiquitin moiety, while increasing ubiquitin moiety concentration generally increased the amount of attachment of ubiquitin moiety to E3 at each concentration of E3.

Figure 4:
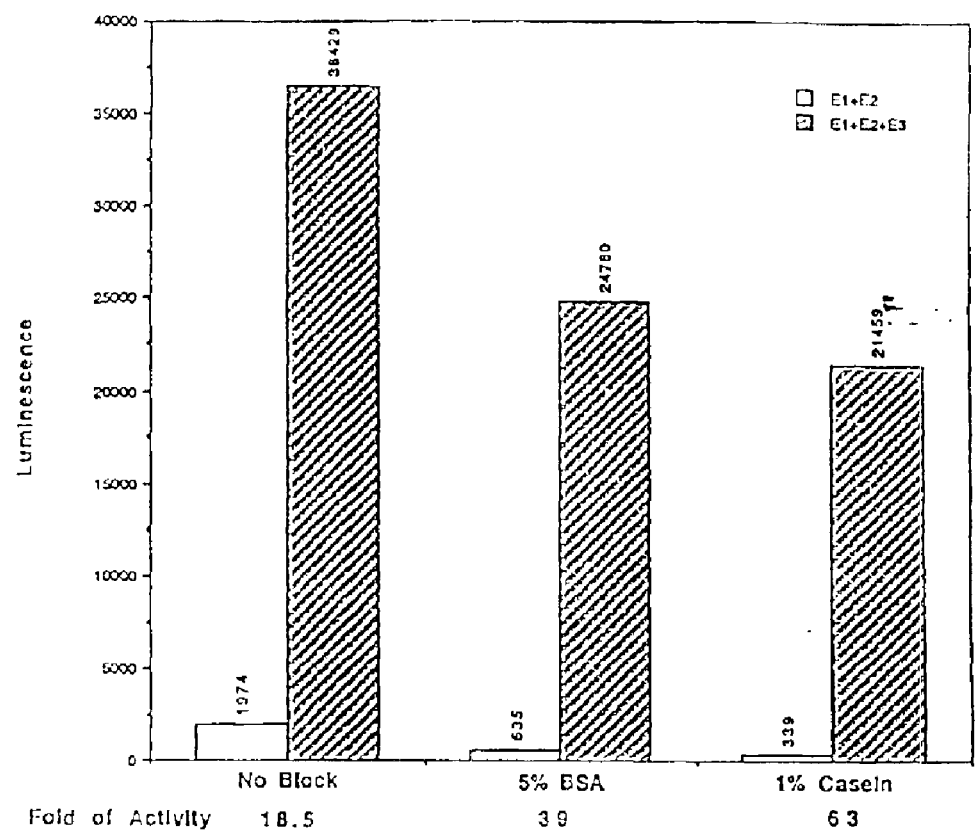
FIG. 4 shows the signal to noise ratio of fluorescent label indicative of the relative amounts of attachment of ubiquitin moiety to an E3, in an assay combining Flag-ubiquitin moiety and an anti-Flag/anti-mouse antibody conjugated to HRP and Luminol fluorescent HRP substrate. The signal was measured from a reaction composition combining ubiquitin moiety, E1, E2, and E3, where the E3 specifically bound the reaction receptacle surface substrate. The background was measured as the amount of fluorescence present after performing the assay in the absence of E3.

It was also found that blocking of the wells with 1% casein improved the signal to noise ratio over either no blocking or blocking with 5% bovine serum albumen (BSA). Background was determined after combining all of the components as above except His-E3 and measuring the resulting fluorescence after pre-treating the wells with 5% BSA, 1% casein or nothing. Results are shown in FIG. 4.

Identification of Agents that Modulate the Attachment of Ubiquitin Moiety to E3

Figure 5A:
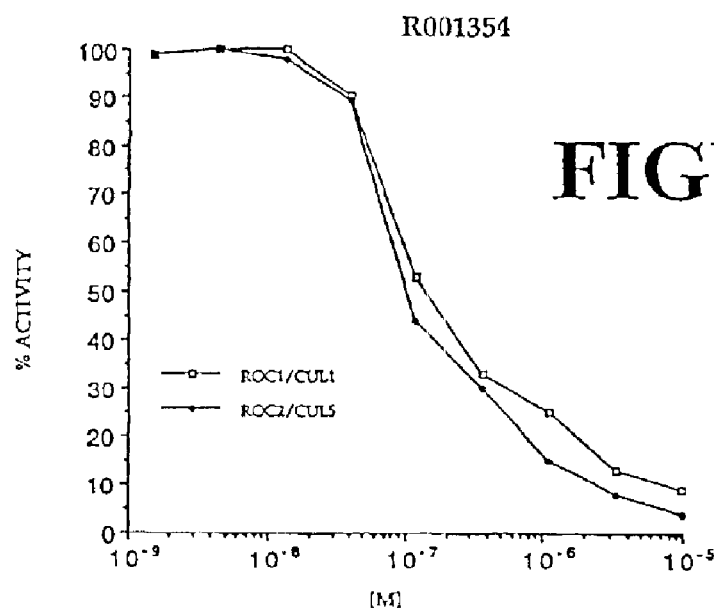
FIG. 5A shows a concentration-dependent reduction in the attachment of ubiquitin moiety to an E3, in assays comprising either ROC1/Cul1 or ROC2/Cul5 as the components of the E3 ubiquitin ligating agent.
Figure 5B:
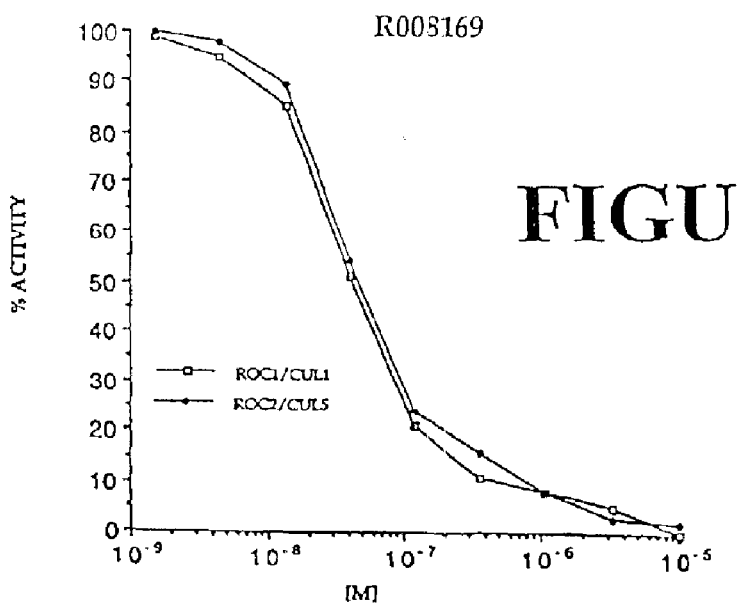
FIG. 5B shows a slightly different pattern of concentration-dependent reduction of attachment of ubiquitin moiety to an E3, by another candidate agent.

To show that the assay is useful for identifying agents that modulate the attachment of ubiquitin moiety to E3, several candidate agents were combined with the ubiquitin agents (E1+E2+E3) and ubiquitin moiety, at varying concentrations as described above. FIG. 5 shows the results from two identified agents that modulate the attachment of ubiquitin moiety to E3. The modulators decreased the attachment of ubiquitin moiety to E3 in a dose-dependent fashion corresponding to the concentration of the ubiquitin agents present in the reaction which comprised either ROC1/Cul1 or ROC2/Cul5 as the E3 component.

Figures 6A, 6B:
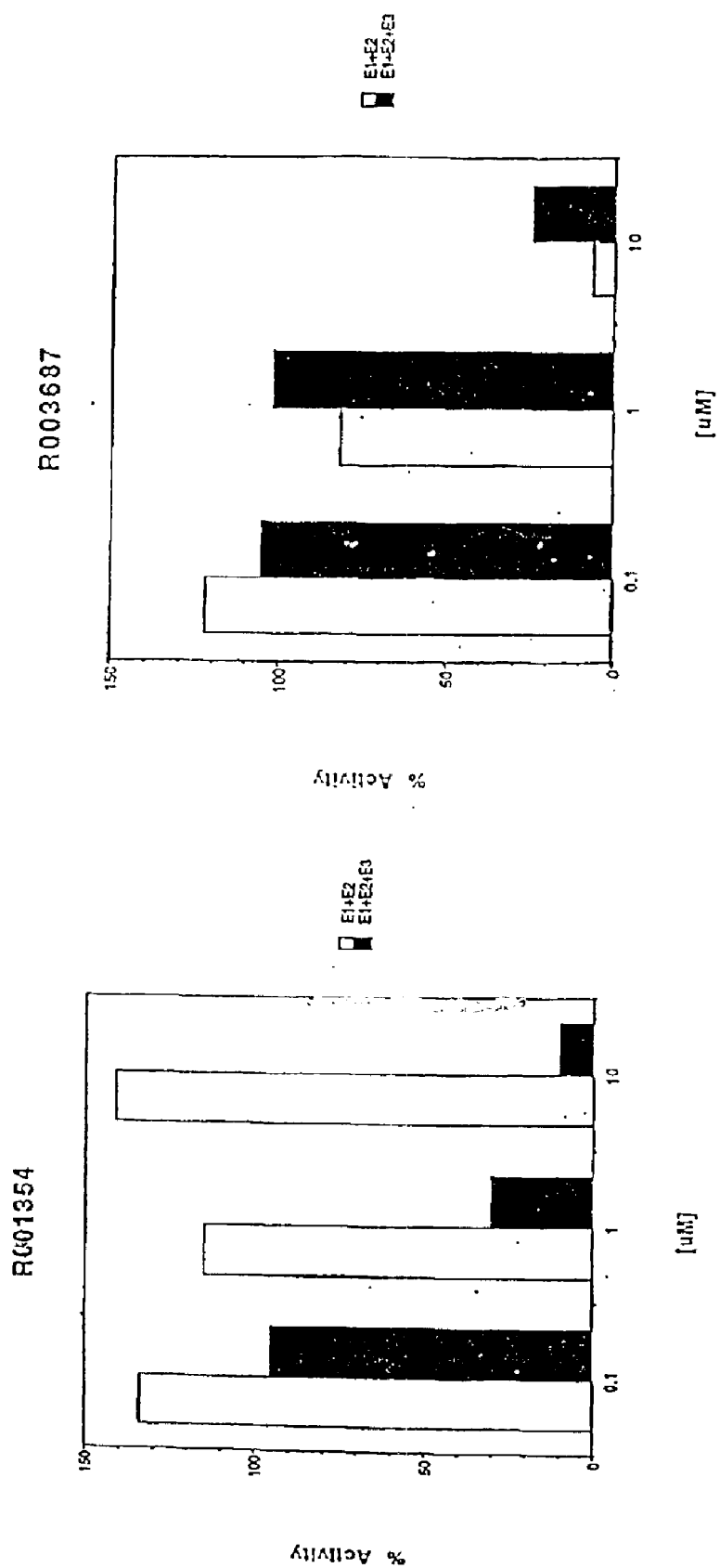
FIG. 6A shows a candidate agent that only modulates the attachment of ubiquitin moiety to an E3.
FIG. 6B shows candidate agent that modulates the attachment of ubiquitin moiety to ubiquitin agents other than E3.

Comparison of the effect of the modulators on the attachment of ubiquitin moiety to E3, as described above, either containing E1, E2 and His-E3 or containing E1, His-E2 and lacking E3, shows whether the modulator affects E3 or a ubiquitin agent other than E3. In FIG. 6A, the identified modulator decreases the attachment of ubiquitin to E3 in the presence of E3, but does not modulate the attachment in the absence of E3, showing that the modulator has a specific effect on the attachment of ubiquitin moiety to E3. In contrast, results shown in FIG. 6B for another modulator reveals that this agent reduces activity whether or not E3 is present, showing that the affects of this agent effect the activity of ubiquitin agents other than E3.

Example 4

FRET Analysis of Ubiquitin Moiety Attached to E3

Ubiquitin moiety was prepared, labeled with either EDANS or fluorescein, and the fluorescence of each of these labels and their interaction as a FRET pair was measured to show attachment of the labeled ubiquitin moiety to E3 and FRET activity of the attached ubiquitin moiety.

Materials and Methods

Ubiquitin moiety were produced incorporating Cys residues into the FLAG-ubiquitin moiety sequence by site-directed mutagenesis using either the primer 5'-CCCCCCAAGCTTTGCATGCAGATTTTCGTGAA GACCCTGACC-3' to produce FLAG-Cys-ubiquitin moiety, or the primer 5'-CCCCCCAAGCTTGCGTGCATGCAGATTTTCGT GAAGACCCTGACC-3' to produce FLAG-Ala-Cys-ubiquitin moiety. Protein was expressed and purified as described above.

Either fluorescein 5-maleimide (peak emission at 515 nm) or 1,5-iodacetamide EDANS (IAEDANS; peak emission at 490 nm) was reacted with the thiol group on the cysteine of the ubiquitin moiety produced as above to form a thioether. The labeling was performed in PBS with 1 mM TCEP. Labeled protein was separated from free label by gel filtration.

The ubiquitin assay was performed substantially as described above, with a few modifications. No nickel substrate was used in the reaction wells, so all of the components were free in solution. Equal amounts of fluorescein labeled ubiquitin moiety and IAEDANS labeled ubiquitin moiety were used. The reaction was performed at room temperature for 2 hours in a volume of 100–150 $\mu$l, then stopped with 50 $\mu$l of 0.5M EDTA, pH 8.

Following the reaction, the products were separated in PBS with 1 mM TCEP by HPLC on a Superdex-75 HR 10/30 size-exclusion column using fluorescence emission detection. A larger molecular weight cutoff gel-filtration column (e.g., Superdex 200 HR 10/30) could be used to resolve individual ligation species.

Results

FIGS. 16A and 16B show the E3-dependent incorporation of Flag-Ala-Cys-ubiquitin moiety labeled with FRET fluorophores into E3-ubiquitin moiety complex. Isolation by HPLC shows emissions from free ubiquitin moiety and ubiquitin moiety attached to the E3 ubiquitin ligating agent. The traces show fluorescent emission at the wavelength described below, under excitation at 336 nm, the optimal excitation wavelength for IAEDANS. FIG. 16A shows the fluorescence signals of IAEDANS (490 nm; larger peak) and fluorescein (515 nm; smaller peak) labeled ubiquitin moiety following combination with E1 and E2 only. The free ubiquitin moiety was isolation using high performance liquid chromatography (HPLC). FIG. 16B shows the fluorescence signals of IAEDANS (490 nm; larger peak at each elution volume) and fluorescein (515 nm; smaller peak at each elution volume) labeled ubiquitin moiety following combination with E1 and E2 and E3 (Roc1/Cul1). The dashed line shows optical density of the protein solution (scale on right), revealing the high sensitivity of the fluorophores despite a very low concentration of protein.

Figure 17:
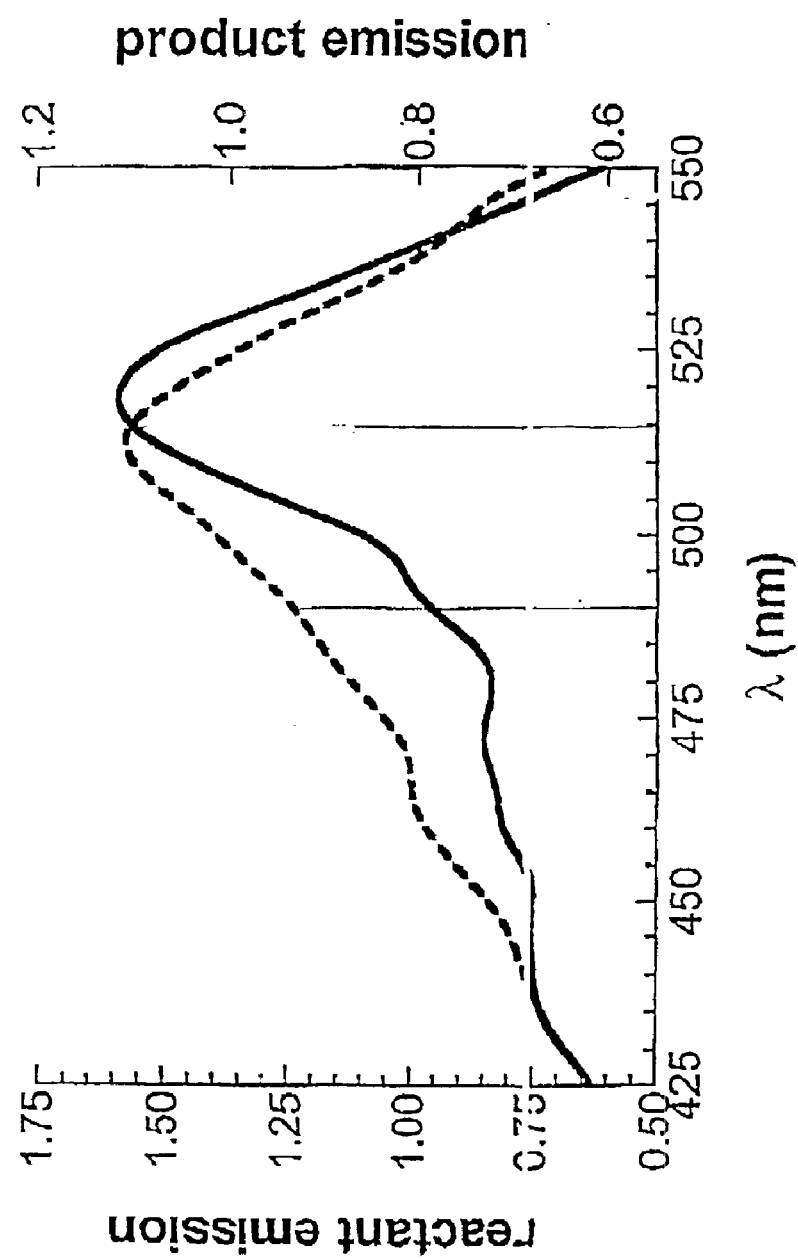
FIG. 17 shows the fluorescence emission spectra of free ubiquitin moiety labeled with the FRET donor/acceptor pair EDANS and fluorescein under excitation at 336 nm. The dashed line shows the emission spectra of free labeled ubiquitin moiety (reactants), while the solid line shows the emission spectra of labeled ubiquitin moiety bound to E3 (products). The greatly increased 515:490 nm emission ratio of the E3-bound ubiquitin moiety as compared with the free ubiquitin moiety shows the energy transfer from the EDANS donor to the fluorescein acceptor of this FRET donor/acceptor pair.

Fluorescein labeled ubiquitin moiety and IAEDANS labeled ubiquitin moiety was attached to E3 in approximately equal amounts. A comparison of the spectral analysis of fluorescent emission from the free (unligated) ubiquitin moiety labeled with both fluorophores and the E3-attached ubiquitin moiety shows a distinct increase in ratio of emission at 515 nm versus 490 nm (FIG. 17). This shows that in the attached ubiquitin moiety, the fluorophores on different ubiquitin moieties are sufficiently close for FRET to be measured.

Example 5

E1+E2+Mdm2+p53 Assay

The attachment of ubiquitin moiety to p53, by combining E1+E2 Ubch5c+Gst-Mdm2+His-p53, and Flag-ubiquitin moiety, was assayed using the following protocol with: E1 obtained commercially (Affiniti Research Products, Exeter, U.K.); Flag-ubiquitin moiety purified from *E. coli*; E2 Ubch5c (also called Ubc-5) purified as GST-Ubch5c from *E. coli* with the GST tag removed; GST-Mdm2 (schematically depicted in FIG. 18) purified from Hi-5 cells by Baculovirus infection with the GST tag intact; and p53 purified from Hi-5 cells by Baculovirus infection (schematically depicted in FIG. 18). E2 Ubch5c was made as described above. Gst-Mdm2 and His-p53 were made as described above for GST-Ubch5c and E3 His-ROC1/Cul1, respectively.

Materials and Methods

The following procedures were used for assays measuring the attachment of ubiquitin moiety to p53 by Western blot analysis. The following combinations of ubiquitin agents, ubiquitin moiety, and p53 were combined in a reaction mixture: E1+E2 Ubch5c+p53 (as a control); Mdm2+p53 (as a control); E1+E2 Ubch5c (as a control); and E1+E2 Ubch5c+Mdm2+p53 (as a control). To each reaction mixture is added the following:

Final Concentration
50 mM Tris pH 7.5
5 mM MgCl$_2$
0.6 mM DTT
2.0 mM ATP
100 ng Flag-ubiquitin moiety (made as described above)
100 ng His-p53.

The buffer solution is brought to a final volume of 80 $\mu$l with milipore-filtered water, followed by the addition of 10 $\mu$l of DMSO.

To the above solution is then added 10 $\mu$l of E1+E2 Ubch5c+p53; Mdm2+p53; E1+E2 Ubch5c; or E1+E2 Ubch5c+Mdm2+p53, in 20 mM Tris buffer, pH 7.5, and 5% glycerol. The His-E2 and Mdm2 is made as described above, and E1 is obtained commercially (as described above). The following amounts of each enzyme are used for these assays: 5 ng of E1; 15 ng E2 Ubch5c; and 50 ng Mdm2. The reaction is then allowed to proceed at 37° C. for 1 hour.

The products of the reaction were then resolved by SDS-PAGE; analyzed by Western blot using Mouse anti-Flag and ant-Mouse Ig-HRP.

Results

Attachment of Ubiquitin Moiety to p53

Figure 19:
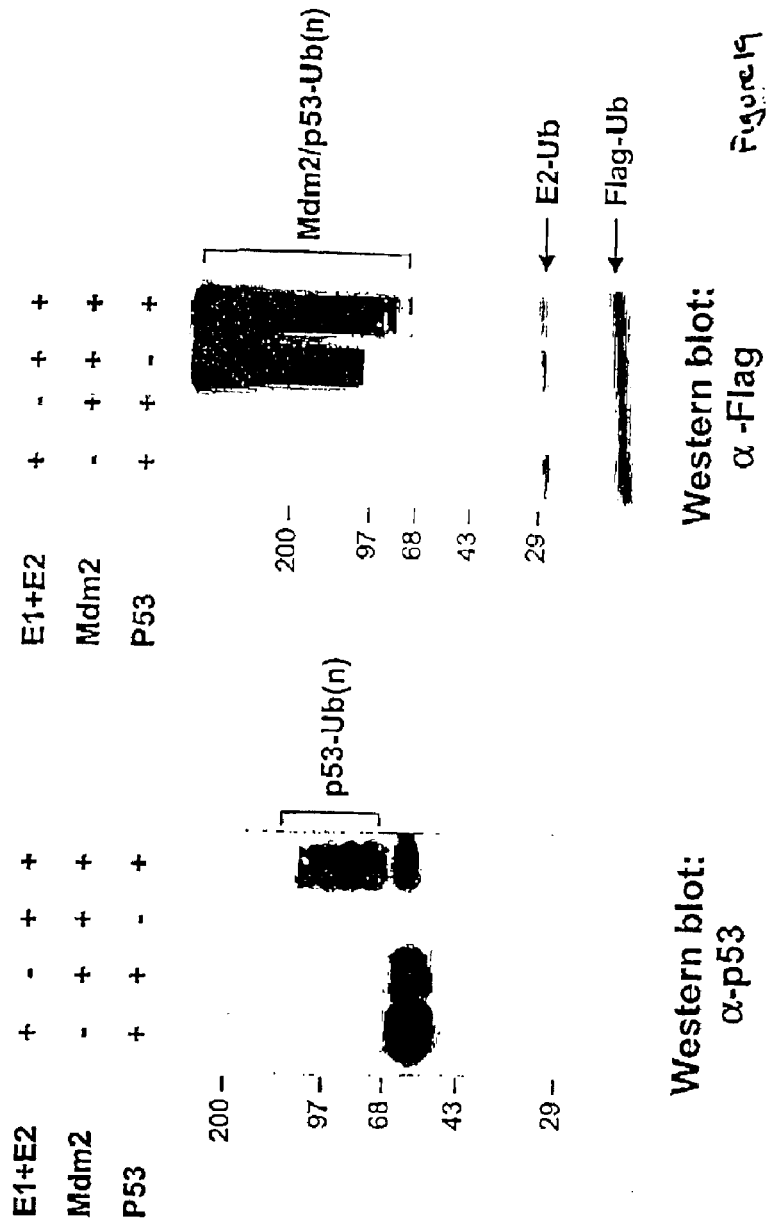
FIG. 19 shows a Western blot analysis of the attachment of ubiquitin moiety to p53 by Mdm2, in vitro.

FIG. 19 shows the attachment of ubiquitin moiety measured for E1+E2 Ubch5c+p53; Mdm2+p53; E1+E2 Ubch5c; and E1+E2 Ubch5c+Mdm2+p53, as described above.

Example 6

E1+E2+Mdm2+p53 Assay

The attachment of ubiquitin moiety to p53, by combining E1+E2 Ubch5c+Gst-Mdm2+His-p53, and Flag-ubiquitin moiety, was assayed using the following protocol with: E1 obtained commercially (Affiniti Research Products, Exeter, U.K.); Flag-ubiquitin moiety purified from *E. coli*; E2 Ubch5c (also called Ubc-5) purified as GST-Ubch5c from *E. coli* with the GST tag removed; GST-Mdm2 (schematically depicted in FIG. 18) purified from Hi-5 cells by Baculovirus infection with the GST tag intact; and p53 purified from Hi-5 cells by Baculovirus infection (schematically depicted in FIG. 18). E2 Ubch5c was made as des cribed above. Gst-Mdm2 and His-p53 were made as described above for GST-Ubch5c and E3 His-ROC1/Cul1, respectively.

Materials and Methods

Figure 20:
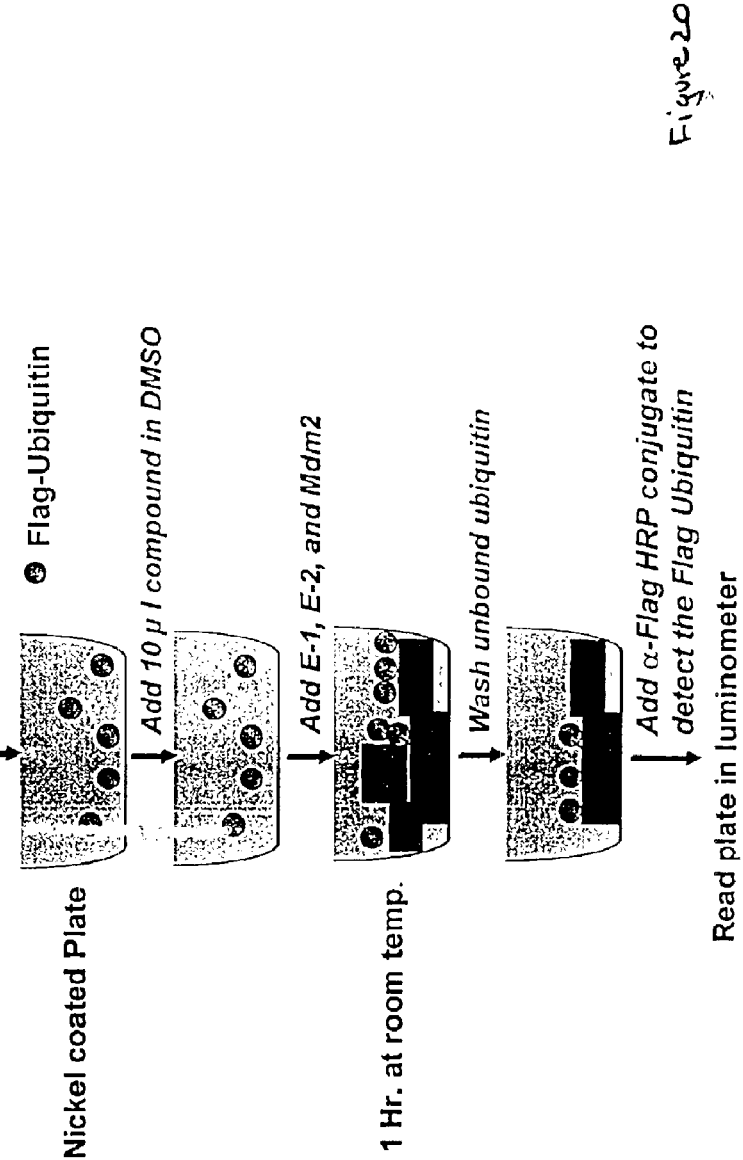
FIG. 20 shows a schematic of a nickel plate based assay for the attachment of ubiquitin moiety to p53 by Mdm2.

The following procedures were used for assays measuring the attachment of ubiquitin moiety to p53, and are illustrated schematically in FIG. 20. The wells of Nickel-substrate 96-well plates (Pierce Chemical) are blocked with 100 µl of 1% casein/phosphate buffered saline (PBS) for 1 hour at room temperature, then washed with 200 µl of PBS 3 times. To each well is added the following Flag-ubiquitin moiety (see above) reaction solution:

Final Concentration 50 mM Tris pH 7.5
5 mM MgCl$_2$
0.6 mM DTT
2.0 mM ATP
100 ng Flag-ubiquitin moiety (made as described above)
100 ng His-p53.

The buffer solution is brought to a final volume of 80 µl with milipore-filtered water, followed by the addition of 10 µl of DMSO.

To the above solution is then added 10 µl of E1, His-E2, and Mdm2 in 20 mM Tris buffer, pH 7.5, and 5% glycerol. The controls contained either Mdm2 alone or His-p53 alone. The His-E2 and Mdm2 is made as described above, and E1 is obtained commercially (as described above). The following amounts of each enzyme are used for these assays: 5 ng/well of E1; 15 ng/well E2 Ubch5c; and 50 ng/well Mdm2. The reaction is then all owed to proceed at room temperature for 1 hour.

Following the ubiquitin reaction, the wells are washed with 200 µl of PBS 3 times. For measurement of the p53-attached ubiquitin moiety, 100 µl of Mouse anti-Flag (1:10,000) and ant-Mouse Ig-HRP (1:15,000) in PBS are added to each well and allowed to incubate at room temperature for 1 hour. The wells are then washed with 200 µl of PBS 3 times, followed by the addition of 100 µl of luminol substrate (1/5 dilution). Luminescence for each well is then measured using a fluorimeter.

Results

Attachment of Ubiquitin Moiety to p53

Figure 21:
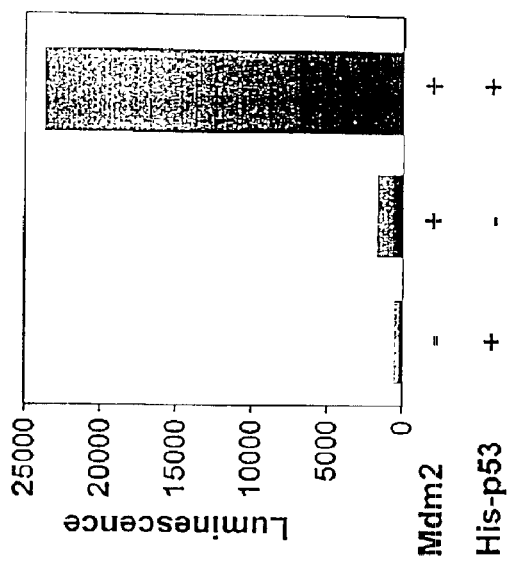
FIG. 21 shows the results of measuring the luminescence indicative of the amount of attachment of ubiquitin moiety to p53 by Mdm2 in the nickel plate based assay.

FIG. 21 shows the luminescence measured for His-p53 alone, Mdm2 alone, and for Mdm2+His-p53 as described above.

Examples of preferred embodiments are depicted in the following figures.

Figure 22:
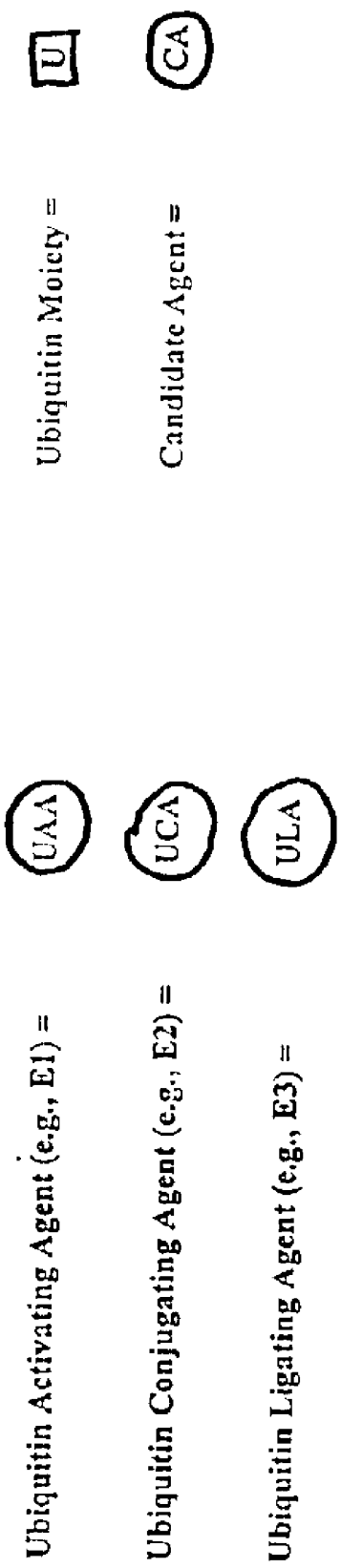
FIG. 22 depicts the key for the ubiquitin activating agent (UAA), ubiquitin conjugating agent (UCA), ubiquitin ligating agent (ULA), ubiquitin moiety (U), and candidate agent (CA) used in the schematics in Figures FIG. 23 schematically depicts a preferred embodiment for assaying for the attachment of ubiquitin moiety to a first ubiquitin agent (UA-1) where the assay comprises:
1) combining a UA-1+CA+U; and
2) assaying for the attachment of the ubiquitin moiety to UA-1. In another preferred embodiment UA-1 is a UAA. In another preferred embodiment, UAA is an E1. In yet another preferred embodiment, UA-1 comprises a label. In another preferred embodiment, the ubiquitin moiety comprises a label.
Figure 23:
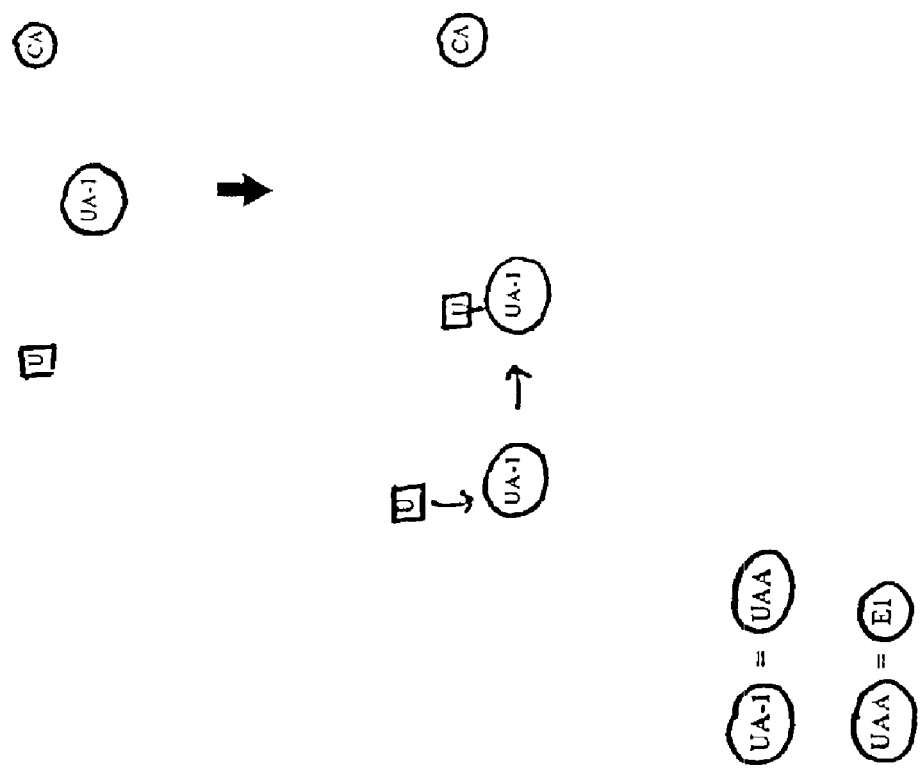

FIG. 22 depicts the key for the ubiquitin activating agent (UAA), ubiquitin conjugating agent (UCA), ubiquitin ligating agent (ULA), ubiquitin moiety (U), and candidate agent (CA) used in the schematics in Figures FIG. 23 schematically depicts a preferred embodiment for assaying for the attachment of ubiquitin moiety to a first ubiquitin agent (UA-1) where the assay comprises:

1) combining a UA-1+CA+U; and
2) assaying for the attachment of the ubiquitin moiety to UA-1. In another preferred embodiment UA-1 is a UAA. In another preferred embodiment, UAA is an E1. In yet another preferred embodiment, UA-1 comprises a label. In another preferred embodiment, the ubiquitin moiety comprises a label.

Figure 24:
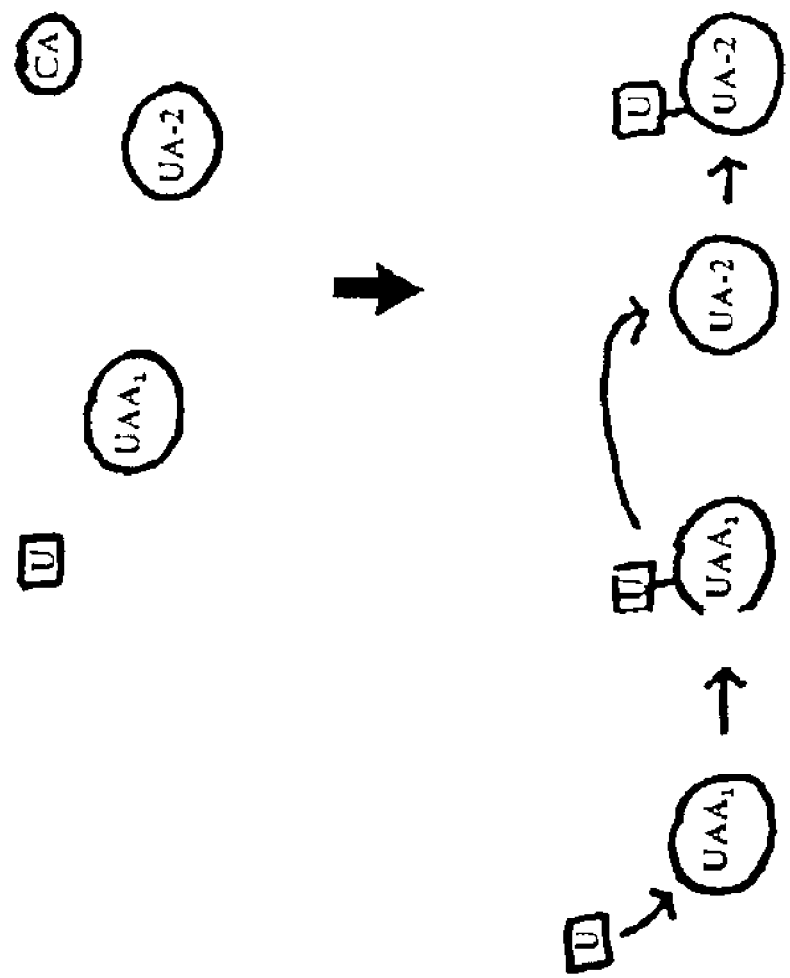
FIG. 24 schematically depicts a preferred embodiment for assaying for the attachment of ubiquitin moiety to a second ubiquitin agent (UA-2) where the assay comprises:
1) combining a first ubiquitin agent that is UAA$_1$+UA-2+CA+U; and
2) assaying for the attachment of the ubiquitin moiety to UA-2. In another preferred embodiment, UA-2 comprises a label. In yet another preferred embodiment, UA-2 comprises a label.

FIG. 24 schematically depicts a preferred embodiment for assaying for the attachment of ubiquitin moiety to a second ubiquitin agent (UA-2) where the assay comprises:

1) combining a first ubiquitin agent that is UAA$_1$+UA-2+ CA+U; and
2) assaying for the attachment of the ubiquitin moiety to UA-2. In another preferred embodiment, UA-2 comprises a label. In yet another preferred embodiment, UA-2 comprises a label.

Figure 25:
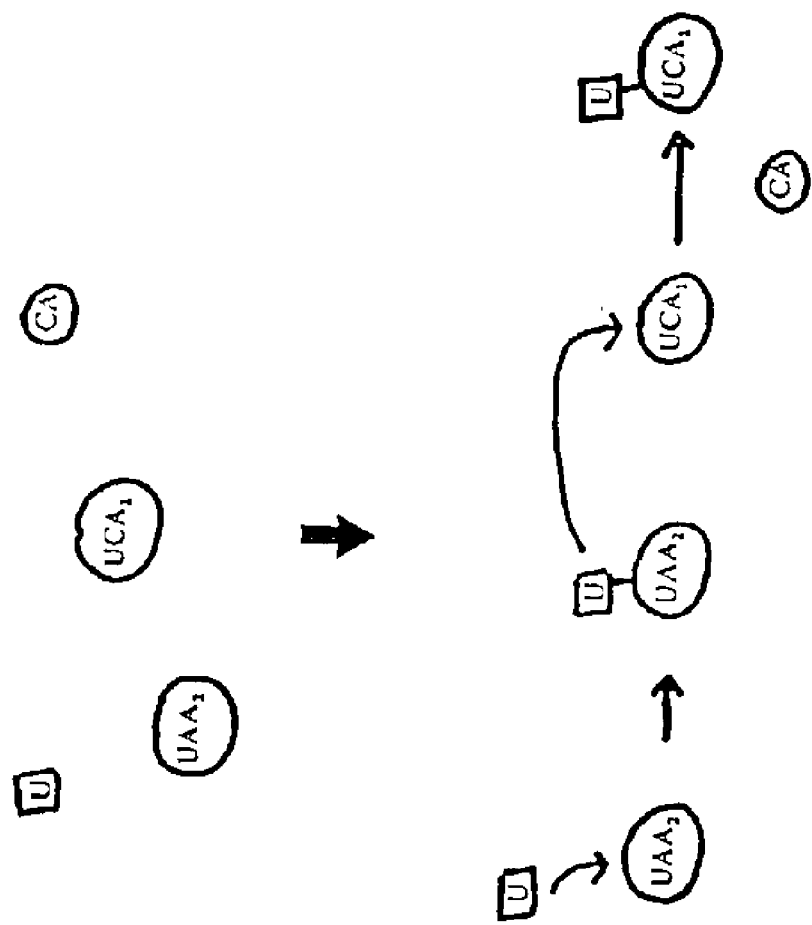
FIG. 25 schematically depicts a preferred embodiment for assaying for the attachment of ubiquitin moiety to a first ubiquitin agent that is a ubiquitin conjugating agent UCA$_1$ where the assay comprises:
1) combining a second ubiquitin agent that is UAA$_2$+UCA$_1$+CA+U; and
2) assaying for the attachment of the ubiquitin moiety to UCA$_1$.

FIG. 25 schematically depicts a preferred embodiment for assaying for the attachment of ubiquitin moiety to a first ubiquitin agent that is a ubiquitin conjugating agent UCA$_1$ where the assay comprises:

1) combining a second ubiquitin agent that is UAA$_2$+ UCA$_1$+CA+U; and
2) assaying for the attachment of the ubiquitin moiety to UCA$_1$.

Figure 26:
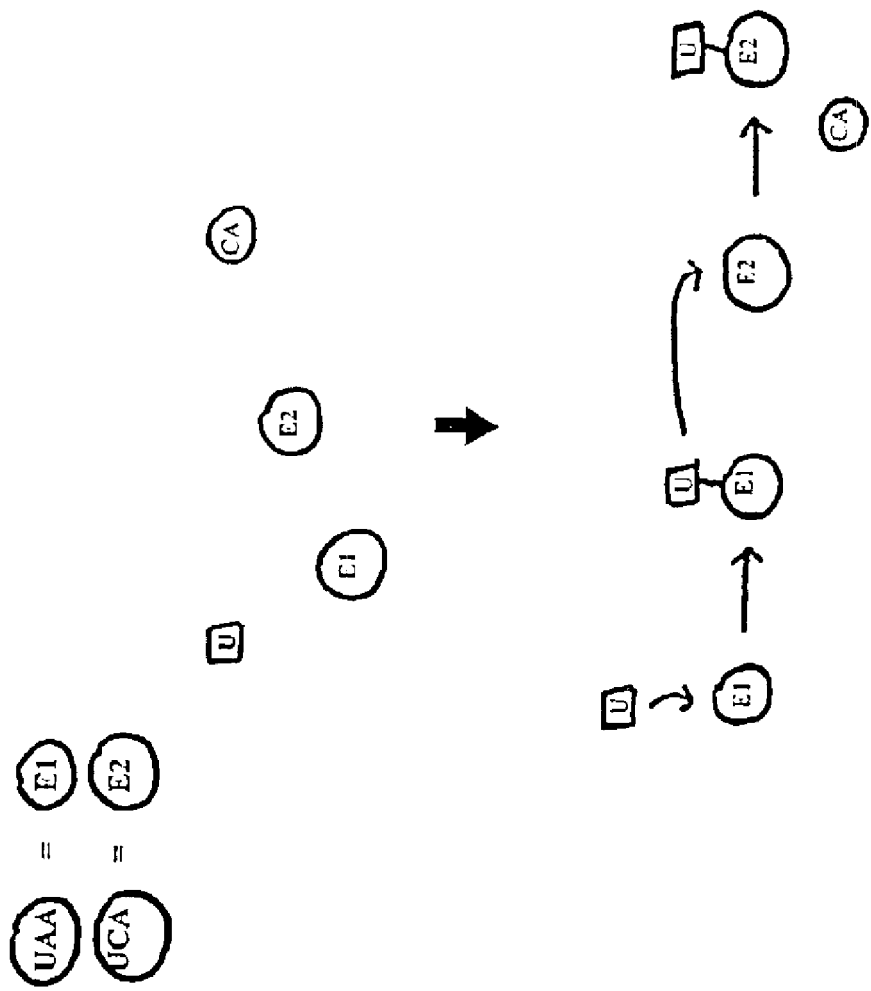
FIG. 26 schematically depicts a preferred embodiment for assaying for the attachment of ubiquitin moiety to ubiquitin conjugating agent that is an E2 where the assay comprises:
1) combining a ubiquitin activating agent that is an E1+E2+CA+U; and
2) assaying for the attachment of the ubiquitin moiety to E2.

FIG. 26 schematically depicts a preferred embodiment for assaying for the attachment of ubiquitin moiety to ubiquitin conjugating agent that is an E2 where the assay comprises:

1) combining a ubiquitin activating agent that is an E1+E2+ CA+U; and
2) assaying for the attachment of the ubiquitin moiety to E2.

FIG. 27 schematically depicts a preferred embodiment for assaying for the attachment of ubiquitin moiety to a first ubiquitin agent that is a ubiquitin ligating agent (ULA$_1$) where the assay comprises:

1) combining a second ubiquitin agent that is a ubiquitin conjugating agent and comprising a ubiquitin moiety UCA$_2$-U+ULA$_1$+CA; and
2) assaying for the attachment of the ubiquitin moiety to ULA$_1$. In another preferred embodiment, the ubiquitin moiety comprises a label. In yet another preferred embodiment, ULA$_1$ comprises a label. In a preferred embodiment the ubiquitin ligating agent comprises an Mdm2 protein.

FIG. 28 schematically depicts a preferred embodiment for assaying for the attachment of ubiquitin moiety to a a ubiquitin ligating agent that is an E3 where the assay comprises:

1) combining a ubiquitin conjugating agent that is an E2 and comprising a ubiquitin moiety+E3+CA; and
2) assaying for the attachment of the ubiquitin moiety to E3. In a preferred embodiment, the E3 is an Mdm2 protein.

FIG. 29 schematically depicts a preferred embodiment for assaying for the attachment of ubiquitin moiety to a ubiquitin conjugating agent that is an E2 where the assay comprises:

1) combining a ubiquitin activating agent that is an E1 and comprising a ubiquitin moiety+E2+CA; and
2) assaying for the attachment of the ubiquitin moiety to E2.

FIG. 30 schematically depicts a preferred embodiment for assaying for the attachment of ubiquitin moiety to a third ubiquitin agent (UA-3) where the assay comprises:

1) combining a ubiquitin activating agent that is an E1 and comprising a ubiquitin moiety+a ubiquitin conjugating agent that is an E2+UA-3+CA; and
2) assaying for the attachment of the ubiquitin moiety to UA-3. In a preferred embodiment, UA-3 comprises an Mdm2 protein.

FIG. 31 schematically depicts a preferred embodiment for assaying for the attachment of ubiquitin moiety to a third ubiquitin agent that is a ubiquitin ligating agent (ULA$_3$) where the assay comprises:

1) combining a ubiquitin activating agent that is an E1 and comprising a ubiquitin moiety+a ubiquitin conjugating agent that is an E2+ULA$_3$+CA; and
2) assaying for the attachment of the ubiquitin moiety to ULA$_3$. In a preferred embodiment the ubiquitin ligating agent comprises an Mdm2 protein.

FIG. 32 schematically depicts a preferred embodiment for assaying for the attachment of ubiquitin moiety to a ubiquitin ligating agent that is an E3 where the assay comprises:

1) combining an E1 comprising a ubiquitin moiety+an E2+an E3+CA; and
2) assaying for the attachment of the ubiquitin moiety to E3. In a preferred embodiment, the E3 is Mdm2.

FIG. 33 schematically depicts a preferred embodiment for assaying for the attachment of ubiquitin moiety to a first ubiquitin agent (UA-1) that is attached to a solid support where the assay comprises:

1) combining a UA-1 (that is attached to a solid support)+CA+U; and
2) assaying for the attachment of the ubiquitin moiety to UA-1. In another preferred embodiment UA-1 is a UAA. In another preferred embodiment, UAA is an E1. In another preferred embodiment, the solid support is a microtiter plate. In another preferred embodiment, the solid support is a bead.

FIG. 34 schematically depicts a preferred embodiment for assaying for the attachment of ubiquitin moiety to a second ubiquitin agent (UA-2) that is attached to a solid suport) where the assay comprises:

1) combining a first ubiquitin agent that is $UAA_1$+UA-2 (attached to a solid support)+CA+U; and
2) assaying for the attachment of the ubiquitin moiety to UA-2. In another preferred embodiment, the solid support is a microtiter plate. In another preferred embodiment, the solid support is a bead. In a preferred embodiment, UA-2 comprises an Mdm 2 protein.

FIG. 35 schematically depicts a preferred embodiment for assaying for the attachment of ubiquitin moiety to a first ubiquitin agent that is a ubiquitin ligating agent ($ULA_1$) that is attached to a solid support where the assay comprises:

1) combining a second ubiquitin agent that is a ubiquitin conjugating agent $UCA_2$ comprising a ubiquitin moiety+$ULA_1$ (attached to a solid support)+CA; and
2) assaying for the attachment of the ubiquitin moiety to $ULA_1$. In a preferred embodiment the ubiquitin ligating agent comprises an Mdm2.

FIG. 36 schematically depicts a preferred embodiment for assaying for the attachment of ubiquitin moiety to a first ubiquitin agent (UA-1) that comprises a label where the assay comprises:

1) combining a UA-1 (plus label)+CA+U; and
2) assaying for the attachment of the ubiquitin moiety to UA-1.

FIG. 37 schematically depicts a preferred embodiment for assaying for the attachment of ubiquitin moiety to a first ubiquitin agent that is a ubiquitin ligating agent ($ULA_1$) that comprises a label where the assay comprises:

1) combining a second ubiquitin agent that is a ubiquitin conjugating agent $UCA_2$ comprising a ubiquitin moiety+$ULA_1$ (plus label)+CA; and
2) assaying for the attachment of the ubiquitin moiety to $ULA_1$. In a preferred embodiment the ubiquitin ligating agent comprises an Mdm2 protein.

FIG. 38 schematically depicts a preferred embodiment for assaying for the attachment of ubiquitin moiety that comprises a label, to a first ubiquitin agent (UA-1) where the assay comprises:

1) combining a UA-1+CA+U (plus label); and
2) assaying for the attachment of the ubiquitin moiety to UA-1.

FIG. 39 schematically depicts a preferred embodiment for assaying for the attachment of ubiquitin moiety that comprises a label, to a second ubiquitin agent (UA-2) where the assay comprises:

1) combining a first ubiquitin agent that is UAA+UA-2+CA+U (plus label); and
2) assaying for the attachment of the ubiquitin moiety to UA-2.

FIG. 40 schematically depicts a preferred embodiment for assaying for the attachment of ubiquitin moiety that com prises a label, to a first ubiquitin agent that is a ubiquitin ligating agent ($ULA_1$) where the assay comprises:

1) combining a second ubiquitin agent that is a ubiquitin conjugating agent $UCA_2$ comprising a ubiquitin moiety (plus label)+$ULA_1$+CA; and
2) assaying for the attachment of the ubiquitin moiety to $ULA_1$. In a preferred embodiment the ubiquitin ligating agent comprises an Mdm2 protein.

FIG. 41 schematically depicts a preferred embodiment for assaying for the attachment of ubiquitin moiety to a first ubiquitin agent that is a ubiquitin ligating agent ($ULA_1$) which comprises a label where the assay comprises:

1) combining a second ubiquitin agent that is a ubiquitin conjugating agent $UCA_2$ comprising a ubiquitin moiety +$ULA_1$ (plus label)+CA; and
2) assaying for the attachment of the ubiquitin moiety to $ULA_1$. In a preferred embodiment the ubiquitin ligating agent comprises an Mdm2 protein.

FIG. 42 schematically depicts a preferred embodiment for assaying for the attachment of ubiquitin moiety to a second ubiquitin agent (UA-2) that comprises a label where the assay comprises:

1) combining a first ubiquitin agent that is $UAA_1$+UA-2 (plus label)+CA+U; and
2) assaying for the attachment of the ubiquitin moiety to UA-2. In a preferred embodiment, UA-2 comprises an Mdm2 protein.

FIG. 43 schematically depicts a preferred embodiment for assaying for the attachment of ubiquitin moiety to a first ubiquitin agent (UA-1) that comprises an attachment tag (or attachment moiety) where the assay comprises:

1) combining a UA-1 (plus attachment tag)+CA+U; and
2) assaying for the attachment of the ubiquitin moiety to UA-1.

FIG. 44 schematically depicts a preferred embodiment for assaying for the attachment of ubiquitin moiety to a first ubiquitin agent that is a ubiquitin ligating agent ($ULA_1$) that comprises an attachment tag (or attachment moiety) where the assay comprises:

1) combining a second ubiquitin agent that is a ubiquitin conjugating agent $UCA_2$ comprising a ubiquitin moiety+$ULA_1$ (plus attachment tag)+CA; and
2) assaying for the attachment of the ubiquitin moiety to $ULA_1$. In a preferred embodiment the ubiquitin ligating agent comprises an Mdm2 protein.

FIG. 45 schematically depicts a preferred embodiment for assaying for the attachment of ubiquitin moiety to a second ubiquitin agent (UA-2) that comprises an attachment tag (or attachment moiety) where the assay comprises:

1) combining a first ubiquitin agent that is $UAA_1$+UA-2 (plus attachment tag)+CA+U; and
2) assaying for the attachment of the ubiquitin moiety to UA-2.

FIG. 46 schematically depicts a preferred embodiment for assaying for the attachment of ubiquitin moiety to a first ubiquitin agent (UA-1) that comprises an epitope tag (or epitope label) where the assay comprises:

1) combining a UA-1 (plus epitope tag)+CA+U; and
2) assaying for the attachment of the ubiquitin moiety to UA-1.

FIG. 47 schematically depicts a preferred embodiment for assaying for the attachment of ubiquitin moiety to a second ubiquitin agent (UA-2) that comprises an epitope tag (or epitope label) where the assay comprises:

1) combining a first ubiquitin agent that is $UAA_1$+UA-2 (plus epitope tag)+CA+U; and
2) assaying for the attachment of the ubiquitin moiety to UA-2.

FIG. 48 schematically depicts a preferred embodiment for assaying for the attachment of ubiquitin moiety to a substrate molecule (s) where the assay comprises:
1) combining a first ubiquitin agent that is a ubiquitin ligating agent ULA$_1$+a second ubiquitin agent+substrate molecule+CA+U; and
2) assaying for the attachment of the ubiquitin moiety to the substrate molecule. In a preferred embodiment the ubiquitin ligating agent comprises an Mdm2 protein and the substrate molecule comprises p53.

FIG. 49 schematically depicts a preferred embodiment for assaying for the attachment of ubiquitin moiety to a substrate molecule (s) where the assay comprises:
1) combining a first ubiquitin agent that is a ubiquitin ligating agent ULA$_1$+a second ubiquitin agent that is a ubiquitin conjugating agent and comprising a ubiquitin moiety+substrate molecule+CA; and
2) assaying for the attachment of the ubiquitin moiety to the substrate molecule. In a preferred embodiment the ubiquitin ligating agent comprises an Mdm2 protein and the substrate molecule comprises p53.

FIG. 50 schematically depicts a preferred embodiment for assaying for the attachment of ubiquitin moiety to a substrate molecule (s) where the assay comprises:
1) combining a first ubiquitin agent that is a ubiquitin ligating agent ULA$_1$+a second ubiquitin agent+a third ubiquitin agent that is a ubiquitin activating agent+a ubiquitin moiety comprising a first FRET tag+substrate molecule comprising a second FRET tag+CA; and
2) assaying for the attachment of the ubiquitin moiety to the substrate molecule. In a preferred embodiment the ubiquitin ligating agent comprises an Mdm2 protein and the substrate molecule comprises p53.

As depicted in FIG. 51, in a preferred embodiment, the E2 has the amino acid sequence (FIG. 51A) and the nucleic acid sequence (FIG. 51B).

Figure 1:
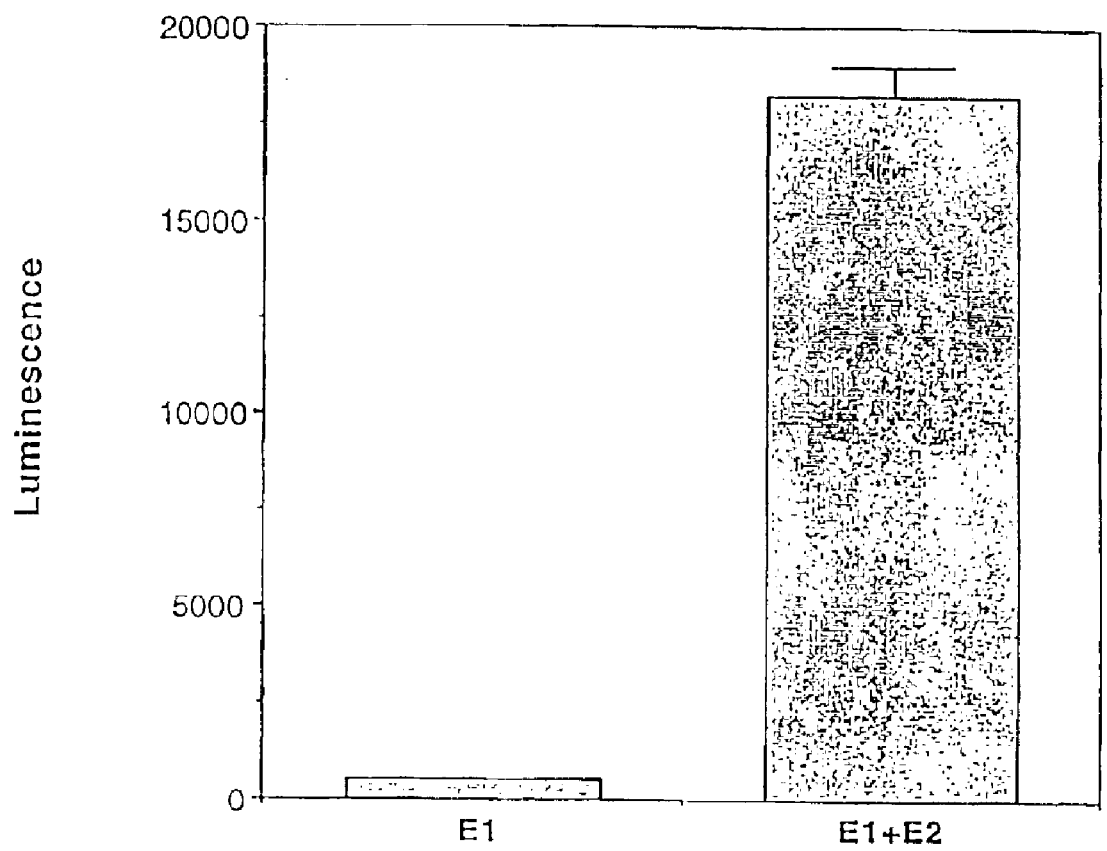
FIG. 1 shows the relative amounts of attachment of fluorescently labeled ubiquitin moiety to an E2 resulting from combining a ubiquitin activating agent, ubiquitin conjugating agent, and ubiquitin moiety. In these experiments, E2 is His-Ubch5c.

As depicted in FIG. 52, in a preferred embodiment, the E2 has the amino acid sequence (FIG. 52A) and the nucleic acid sequence (FIG. 52B1 and FIG. 52B2).

As depicted in FIG. 53, in a preferred embodiment, the E2 has the amino acid sequence (FIG. 53A) and the nucleic acid sequence (FIG. 53B1 and FIG. 53B2).

As depicted in FIG. 54, in a preferred embodiment, the E2 has the amino acid sequence (FIG. 54A) and the nucleic acid sequence (FIG. 54B).

As depicted in FIG. 55, in a preferred embodiment, the E2 has the amino acid sequence (FIG. 55A) and the nucleic acid sequence (FIG. 55B).

We claim:

1. A method of assaying for an agent that modulates the attachment of a ubiquitin moiety to at least one ubiquitin agent, said method comprising:
   a) combining:
      i) a first ubiquitin agent, wherein said first ubiquitin agent is an ubiquitin activating agent;
      ii) a candidate agent; and
      iii) a ubiquitin moiety; and
   b) assaying for the attachment of said ubiquitin moiety to said first agent thereby identifying the candidate agent is the agent that modulates the attachment of said ubiquitin moiety to said first agent.

2. The method according to claim 1, wherein said ubiquitin activating agent is an E1.

3. The method according to claim 1, further comprising including a second ubiquitin agent in said combining step.

4. The method according to claim 3, wherein second agent is a ubiquitin conjugating agent.

5. The method according to claim 4, wherein said ubiquitin conjugating agent is an E2 and said ubiquitin activating agent is an E1.

6. The method according to claim 4, wherein said ubiquitin conjugating agent is an E2 and said ubiquitin activating agent is an E1 comprising said ubiquitin moiety.

7. The method according to claim 3, further comprising a third ubiquitin agent, wherein said third agent is a ubiquitin ligating agent and said second agent is a ubiquitin conjugating agent comprising said ubiquitin moiety.

8. The method according to claim 7, wherein said ubiquitin ligating agent is an E3 and said ubiquitin conjugating agent is an E2 comprising said ubiquitin moiety.

9. The method according to claim 7, wherein said third ubiquitin agent is attached to a solid support.

10. The method according to claim 7, wherein said third agent comprises a tag.

11. The method according to claim 7, wherein said third agent comprises an attachment tag.

12. The method according to claim 7, wherein said third agent comprises a label.

13. The method according to claim 7, wherein said third agent comprises an epitope tag.

14. The method according to claims 3, wherein said second ubiquitin agent is attached to a solid support.

15. The method according to claim 3, wherein said second agent comprises a tag.

16. The method according to claim 3, wherein said second agent comprises an attachment tag.

17. The method according to claim 3, wherein said second agent comprises a label.

18. The method according to claim 3, wherein said second agent comprises an epitope tag.

19. The method according to claim 1, wherein said first ubiquitin agent is attached to a solid support.

20. The method according to any of claims 19, 14, and 9, wherein said solid support is a microtiter plate.

21. The method according to any of claims 19, 14, and 9, wherein said solid support is a bead.

22. The method according to claim 1, wherein said first agent comprises a tag.

23. The method according to any of claims 1, 3, and 7, wherein said ubiquitin moiety comprises a tag.

24. The method according to claim 1, wherein said first agent comprises an attachment tag.

25. The method according to claim 1, wherein said first agent comprises a label.

26. The method according to claim 1, wherein said first agent comprises an epitope tag.

27. The method according to any of claims 1, 3, and 7, wherein at least a first and a second ubiquitin moiety is used, wherein said first and second ubiquitin moiety moieties comprise different fluorescent labels, and wherein said labels form a fluorescence resonance energy transfer (FRET) pair.

28. A method of assaying for an agent that modulates the attachment of a ubiquitin moiety to at least one ubiquitin agent, said method comprising:
   a) combining:
      i) a first ubiquitin agent comprising a ubiquitin ligating agent;
      ii) a second ubiquitin agent;
      iii) a candidate agent;
      iv) a ubiquitin moiety;
      v) a target protein; and
      vi) a third ubiquitin agent, comprising a ubiquitin activating agent; and
   b) assaying for the attachment of said ubiquitin moiety to said first agent thereby identifying the candidate agent is the agent that modulates the attachment of said ubiquitin moiety to said first agent.

29. The method according to claim 28, wherein said second agent is a ubiquitin conjugating agent comprising said ubiquitin moiety.

30. The method according to claim 28, wherein said target protein and said ubiquitin moiety comprise different fluorescent labels, and wherein said labels form a fluorescence resonance energy transfer (FRET) pair.

31. The method according to claim 1 or 28, wherein said ubiquitin moiety is a mammalian ubiquitin moiety.

32. The method according to claim 28, wherein said ubiquitin moiety comprises a label.

33. The method according to claim 28, wherein said label comprises an epitope tag.

* * * * *

SEQUENCE LISTING

```
<160> NUMBER OF SEQ ID NOS: 27

<210> SEQ ID NO 1
<211> LENGTH: 3177
<212> TYPE: DNA
<213> ORGANISM: Oryctolagus cuniculus

<400> SEQUENCE: 1
atgtccagct cgccgctgtc caagaaacgt cgcgtgtccg ggcctgatcc aaagccgggt      60
tctaactgct cccctgccca gtccgtgttg ccccaagtgc cctcggcgcc aaccaacgga     120
atggcgaaga acggcagtga agcagacatc gatgagggcc tttactcccg gcagctgtat     180
gtgttgggcc atgaggcgat gaagcggctc cagacatcca gcgttctggt gtcaggcctg     240
cggggcctgg gggtagagat cgcgaagaac atcatccttg gcggggtcaa ggccgtgacc     300
ctccatgacc agggcacggc ccagtgggct gacctctcct cccagttcta cctgcgagag     360
gaggacatag ggaaaaaccg cgctgaggtg tcacagcccc gccttgctga actcaatagc     420
tacgtgcctg tcaccgccta cactgggccg ctggttgagg acttcctcag tggcttccag     480
gtggtggtcc tcactaacag cccccctggag gaccagctgc gcgtgggcga gttctgtcat     540
agccgtggca tcaagctggt agtggcagac acgagaggct tgtttgggca actcttctgc     600
gactttggag aggaaatgat cctcacagat tccaacgggg agcagcccct cagcaccatg     660
gtttctatgg tcaccaagga caaccctggt gtggttacct gcctggatga ggcccgacat     720
gggtttgaga gtggcgattt tgtttccttc tccgaagtac agggcatgac tgagctcaat     780
ggaaaccagc ccatagagat caaagtcctg ggtccttaca cctttagcat ctgtgacacc     840
tccaacttct ccgattacat ccgtggaggc attgtcagcc aggtcaaagt acctaagaag     900
ataagcttta aatccttgtc agcctcgctg gcagagcctg actttgtgat gacggacttc     960
gccaagtttt ctcgccccgc tcagcttcac attggcttcc aggccttgca caagtctgt    1020 gcacagcaca gccggccacc tagaccccgg aacgaggagg atgcagcaga gctggtgacc    1080
ctagcacgcg ctgtgaactc taaagcctcg tcggcagtgc agcaagatag cctggatgag    1140
```

-continued

```
gacctcatcc ggaacctggc ctttgtggca gccggggacc tggcgcccat caatgccttc      1200
attgggggcc tggctgccca ggaagtcatg aaggcctgct ctgggaagtt tatgcccatc      1260
atgcagtggc tgtactttga tgcccttgag tgtctcccgg aggacaaaga atccctcaca      1320
gaggacaagt gcctcccgcg ccagaaccgt tatgatgggc aggtggctgt gtttggctca      1380
gacctgcaag agaagctggg caggcagaag tacttcctgg tgggtgcagg ggctattggc      1440
tgtgagctgc tcaagaactt tgccatgatt gggctgggct gtggtgagaa cggagaaata      1500
attgtcacag acatggacac cattgagaaa tctaatctga accgacagtt tctattccgg      1560
ccctgggatg tcacgaagtt aaaatctgac acagctgctg cagctgtgca ccagatgaat      1620
ccacatatcc gggtgacaag ccaccagaac cgtgtgggtc ctgacactga acgtatctac      1680
gacgacgatt tcttccaaac tctggatggc gtggccaacg ccttagacaa cgtggatgcc      1740
cgcatgtaca tggaccgccg ctgcgtgtac taccggaagc cgctgctcga atcaggcacc      1800
ctgggcacca agggcaacgt ccaggtggtg atccccttcc tgacagagtc ctacagctcc      1860
agccaagacc cacctgagaa gtccatcccc atctgtaccc tgaagaactt ccccaacgcc      1920
atcgaacaca ctcttcagtg ggctcgggat gaatttgaag gcctcttcaa gcagccagcg      1980
gaaaatgtca accagtacct cacagaccct aagtttgtgg agcggacatt gcggctggcg      2040
ggtacccagc cactggaggt gctggaggct gtgcagcgca gcctggtgct gcagctaccg      2100
cagagctggg cagactgtgt gacctgggcc tgccaccact ggcacaccca gtattctaac      2160
aatatccggc agctgttgca caacttccct cccgaccagc tcacaagctc gggagctccc      2220
ttctggtctg ggcccaaacg ttgtcctcac ccactcacct ttgatgttag caaccctctg      2280
catctggact atgtgatggc tgctgccaac ctgtttgccc agacctacgg gctggcaggc      2340
tctcaggacc gagctgctgt ggccacactc ctgcagtctg tacaggtccc cgagtttacc      2400
cccaagtctg gcgtcaaaat ccacgtttct gaccaggagc tgcagagcgc caatgcttct      2460
gttgacgaca gccgtttaga ggagctcaag gctacgctgc ctagccccga caagctccct      2520
ggattcaaga tgtaccccat tgactttgag aaggatgatg atagtaactt tcacatggac      2580
ttcattgtgg ccgcatccaa cctccgggcc gaaaactatg acattccccc tgcagaccgg      2640
cacaagagca agctgattgc agggaagatc atcccagcca ttgccacgac acagcagct       2700 gtcgttggcc ttgtgtgtct ggagctgtac aaggtagtgc agggacaccg cacctcgac       2760 tcctacaaga atggtttcct caacctggcc ctgccgtttt tcggtttctc tgaacctctg      2820
gctgcaccac gtcaccagta ctataaccaa gagtggacat tgtgggatcg ctttgaggtt      2880
cagggactgc agcccaacgg tgaggagatg accctcaaac aattcctcga ctactttaag      2940
acagagcaca aattggagat taccatgctg tcccagggtg tgtccatgct ctattccttc      3000
tttatgccag ctgcgaagct caaggaacgg ttggaccagc cgatgacaga gattgtaagc      3060
cgtgtgtcga agcgaaagct gggccgccac gtgcgggcgc tggtgcttga gctgtgctgc      3120
aacgacgaga gcggcgagga cgtcgaagtc ccctacgtcc gatataccat ccgttaa         3177
```

<210> SEQ ID NO 2
<211> LENGTH: 1059
<212> TYPE: PRT
<213> ORGANISM: Oryctolagus cuniculus

<400> SEQUENCE: 2

Met Ser Ser Ser Pro Leu Ser Lys Lys Arg Arg Val Ser Gly Pro Asp

-continued

```
1               5                   10                  15
Pro Lys Pro Gly Ser Asn Cys Ser Pro Ala Gln Ser Val Leu Pro Gln
                20                  25                  30
Val Pro Ser Ala Pro Thr Asn Gly Met Ala Lys Asn Gly Ser Glu Ala
                35                  40              45
Asp Ile Asp Glu Gly Leu Tyr Ser Arg Gln Leu Tyr Val Leu Gly His
    50                  55                  60
Glu Ala Met Lys Arg Leu Gln Thr Ser Ser Val Leu Val Ser Gly Leu
65                  70                  75                  80
Arg Gly Leu Gly Val Glu Ile Ala Lys Asn Ile Ile Leu Gly Gly Val
                85                  90                  95
Lys Ala Val Thr Leu His Asp Gln Gly Thr Ala Gln Trp Ala Asp Leu
            100                 105                 110
Ser Ser Gln Phe Tyr Leu Arg Glu Glu Asp Ile Gly Lys Asn Arg Ala
            115                 120             125
Glu Val Ser Gln Pro Arg Leu Ala Glu Leu Asn Ser Tyr Val Pro Val
        130                 135                 140
Thr Ala Tyr Thr Gly Pro Leu Val Glu Asp Phe Leu Ser Gly Phe Gln
145                 150                 155                 160
Val Val Val Leu Thr Asn Ser Pro Leu Glu Asp Gln Leu Arg Val Gly
            165                 170                 175
Glu Phe Cys His Ser Arg Gly Ile Lys Leu Val Val Ala Asp Thr Arg
            180                 185                 190
Gly Leu Phe Gly Gln Leu Phe Cys Asp Phe Gly Glu Glu Met Ile Leu
            195                 200                 205
Thr Asp Ser Asn Gly Glu Gln Pro Leu Ser Thr Met Val Ser Met Val
210                 215                 220
Thr Lys Asp Asn Pro Gly Val Val Thr Cys Leu Asp Glu Ala Arg His
225                 230                 235                 240
Gly Phe Glu Ser Gly Asp Phe Val Ser Phe Ser Glu Val Gln Gly Met
                245                 250                 255
Thr Glu Leu Asn Gly Asn Gln Pro Ile Glu Ile Lys Val Leu Gly Pro
            260                 265                 270
Tyr Thr Phe Ser Ile Cys Asp Thr Ser Asn Phe Ser Asp Tyr Ile Arg
            275                 280                 285
Gly Gly Ile Val Ser Gln Val Lys Val Pro Lys Lys Ile Ser Phe Lys
            290                 295             300
Ser Leu Ser Ala Ser Leu Ala Glu Pro Asp Phe Val Met Thr Asp Phe
305                 310                 315                 320
Ala Lys Phe Ser Arg Pro Ala Gln Leu His Ile Gly Phe Gln Ala Leu
                325                 330                 335
His Lys Phe Cys Ala Gln His Ser Arg Pro Pro Arg Pro Arg Asn Glu
            340                 345                 350
Glu Asp Ala Ala Glu Leu Val Thr Leu Ala Arg Ala Val Asn Ser Lys
            355                 360                 365
Ala Ser Ser Ala Val Gln Asp Ser Leu Asp Glu Asp Leu Ile Arg
        370                 375                 380
Asn Leu Ala Phe Val Ala Ala Gly Asp Leu Ala Pro Ile Asn Ala Phe
385                 390                 395                 400
Ile Gly Gly Leu Ala Ala Gln Glu Val Met Lys Ala Cys Ser Gly Lys
                405                 410                 415
Phe Met Pro Ile Met Gln Trp Leu Tyr Phe Asp Ala Leu Glu Cys Leu
            420                 425                 430
```

```
Pro Glu Asp Lys Glu Ser Leu Thr Glu Asp Lys Cys Leu Pro Arg Gln
            435                 440                 445

Asn Arg Tyr Asp Gly Gln Val Ala Val Phe Gly Ser Asp Leu Gln Glu
            450                 455                 460

Lys Leu Gly Arg Gln Lys Tyr Phe Leu Val Gly Ala Gly Ala Ile Gly
465                 470                 475                 480

Cys Glu Leu Leu Lys Asn Phe Ala Met Ile Gly Leu Gly Cys Gly Glu
            485                 490                 495

Asn Gly Glu Ile Ile Val Thr Asp Met Asp Thr Ile Glu Lys Ser Asn
            500                 505                 510

Leu Asn Arg Gln Phe Leu Phe Arg Pro Trp Asp Val Thr Lys Leu Lys
            515                 520                 525

Ser Asp Thr Ala Ala Ala Val His Gln Met Asn Pro His Ile Arg
            530                 535                 540

Val Thr Ser His Gln Asn Arg Val Gly Pro Asp Thr Glu Arg Ile Tyr
545                 550                 555                 560

Asp Asp Asp Phe Phe Gln Thr Leu Asp Gly Val Ala Asn Ala Leu Asp
            565                 570                 575

Asn Val Asp Ala Arg Met Tyr Met Asp Arg Arg Cys Val Tyr Tyr Arg
            580                 585                 590

Lys Pro Leu Leu Glu Ser Gly Thr Leu Gly Thr Lys Gly Asn Val Gln
            595                 600                 605

Val Val Ile Pro Phe Leu Thr Glu Ser Tyr Ser Ser Ser Gln Asp Pro
            610                 615                 620

Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
            645                 650                 655

Lys Gln Pro Ala Glu Asn Val Asn Gln Tyr Leu Thr Asp Pro Lys Phe
            660                 665                 670

Val Glu Arg Thr Leu Arg Leu Ala Gly Thr Gln Pro Leu Glu Val Leu
            675                 680                 685

Glu Ala Val Gln Arg Ser Leu Val Leu Gln Leu Pro Gln Ser Trp Ala
690                 695                 700

Asp Cys Val Thr Trp Ala Cys His His Trp Thr Gln Tyr Ser Asn
705                 710                 715                 720

Asn Ile Arg Gln Leu Leu His Asn Phe Pro Pro Asp Gln Leu Thr Ser
            725                 730                 735

Ser Gly Ala Pro Phe Trp Ser Gly Pro Lys Arg Cys Pro His Pro Leu
            740                 745                 750

Thr Phe Asp Val Ser Asn Pro Leu His Leu Asp Tyr Val Met Ala Ala
            755                 760                 765

Ala Asn Leu Phe Ala Gln Thr Tyr Gly Leu Ala Gly Ser Gln Asp Arg
            770                 775                 780

Ala Ala Val Ala Thr Leu Leu Gln Ser Val Gln Val Pro Glu Phe Thr
785                 790                 795                 800

Pro Lys Ser Gly Val Lys Ile His Val Ser Asp Gln Glu Leu Gln Ser
            805                 810                 815

Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
            835                 840                 845
```

```
Phe Glu Lys Asp Asp Asp Ser Asn Phe His Met Asp Phe Ile Val Ala
        850                 855                 860

Ala Ser Asn Leu Arg Ala Glu Asn Tyr Asp Ile Pro Pro Ala Asp Arg
865                 870                 875                 880

His Lys Ser Lys Leu Ile Ala Gly Lys Ile Ile Pro Ala Ile Ala Thr
                885                 890                 895

Thr Thr Ala Ala Val Val Gly Leu Val Cys Leu Glu Leu Tyr Lys Val
            900                 905                 910

Val Gln Gly His Arg His Leu Asp Ser Tyr Lys Asn Gly Phe Leu Asn
        915                 920                 925

Leu Ala Leu Pro Phe Phe Gly Phe Ser Glu Pro Leu Ala Ala Pro Arg
    930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
                965                 970                 975

Asp Tyr Phe Lys Thr Glu His Lys Leu Glu Ile Thr Met Leu Ser Gln
            980                 985                 990

Gly Val Ser Met Leu Tyr Ser Phe  Phe Met Pro Ala Ala  Lys Leu Lys
            995                 1000                1005

Glu Arg Leu Asp Gln Pro Met  Thr Glu Ile Val Ser  Arg Val Ser
    1010                1015                1020

Lys Arg Lys Leu Gly Arg His  Val Arg Ala Leu Val  Leu Glu Leu
    1025                1030                1035

Cys Cys  Asn Asp Glu Ser Gly  Glu Asp Val Glu Val  Pro Tyr Val
    1040                1045                1050

Arg Tyr  Thr Ile Arg Glx
    1055

<210> SEQ ID NO 3
<211> LENGTH: 444
<212> TYPE: DNA
<213> ORGANISM: Homo sapiens

<400> SEQUENCE: 3
atggcgctga aacggattaa taaggaactt agtgatttgg cccgtgaccc tccagcacaa    60
tgttctgcag gtccagttgg ggatgatatg tttcattggc aagccacaat tatgggacct   120
aatgacagcc catatcaagg cggtgtattc tttttgacaa ttcatttttcc tacagactac   180 cccttcaaac cacctaaggt tgcatttaca acaagaattt atcatccaaa tattaacagt   240
aatggcagca tttgtctcga tattctaaga tcacagtggt cgcctgcttt aacaatttct   300
aaagttcttt tatccatttg ttcactgcta tgtgatccaa acccagatga ccccctagtg   360
ccagagattg cacggatcta taaaacagac agagataagt acaacagaat atctcgggaa   420
tggactcaga agtatgccat gtga                                          444

<210> SEQ ID NO 4
<211> LENGTH: 148
<212> TYPE: PRT
<213> ORGANISM: Homo sapiens

<400> SEQUENCE: 4

Met Ala Leu Lys Arg Ile Asn Lys Glu Leu Ser Asp Leu Ala Arg Asp
1               5                   10                  15

Pro Pro Ala Gln Cys Ser Ala Gly Pro Val Gly Asp Asp Met Phe His
            20                  25                  30
```

```
Trp Gln Ala Thr Ile Met Gly Pro Asn Asp Ser Pro Tyr Gln Gly Gly
            35                  40                  45

Val Phe Phe Leu Thr Ile His Phe Pro Thr Asp Tyr Pro Phe Lys Pro
    50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Lys
            115                 120                 125

Thr Asp Arg Asp Lys Tyr Asn Arg Ile Ser Arg Glu Trp Thr Gln Lys
            130                 135                 140

Tyr Ala Met Glx
145

<210> SEQ ID NO 5
<211> LENGTH: 84
<212> TYPE: PRT
<213> ORGANISM: Homo sapiens

<400> SEQUENCE: 5

Met Lys Val Lys Ile Lys Cys Trp Asn Gly Val Ala Thr Trp Leu Trp
1               5                   10                  15

Val Ala Asn Asp Glu Asn Cys Gly Ile Cys Arg Met Ala Phe Asn Gly
            20                  25                  30

Cys Cys Pro Asp Cys Lys Val Pro Gly Asp Asp Cys Pro Leu Val Trp
            35                  40                  45

Gly Gln Cys Ser His Cys Phe His Met His Cys Ile Leu Lys Trp Leu
            50                  55                  60

His Ala Gln Gln Val Gln Gln His Cys Pro Met Cys Arg Gln Thr Trp
65                  70                  75                  80

Lys Phe Lys Glu

<210> SEQ ID NO 6
<211> LENGTH: 108
<212> TYPE: PRT
<213> ORGANISM: Homo sapiens

<400> SEQUENCE: 6

Met Ala Ala Met Asp Val Asp Thr Pro Ser Gly Thr Asn Ser Gly
1               5                   10                  15

Ala Gly Lys Lys Arg Phe Glu Val Lys Lys Trp Asn Ala Val Ala Leu
            20                  25                  30

Trp Ala Trp Asp Ile Val Val Asp Asn Cys Ala Ile Cys Arg Asn His
            35                  40                  45

Ile Met Asp Leu Cys Ile Glu Cys Gln Ala Asn Gln Ala Ser Ala Thr
            50                  55                  60

Ser Glu Glu Cys Thr Val Ala Trp Gly Val Cys Asn His Ala Phe His
65                  70                  75                  80

Phe His Cys Ile Ser Arg Trp Leu Lys Thr Arg Gln Val Cys Pro Leu
                85                  90                  95

Asp Asn Arg Glu Trp Glu Phe Gln Lys Tyr Gly His
            100                 105
```

<210> SEQ ID NO 7
<211> LENGTH: 342
<212> TYPE: DNA
<213> ORGANISM: Homo sapiens

<400> SEQUENCE: 7

| | | | | | |
|---|---|---|---|---|---|
| atggccgacg | tggaagacgg | agaggaaacc | tgcgccctgg | cctctcactc | cgggagctca | 60 |
| ggctcaacgt | cgggaggcga | caagatgttc | tccctcaaga | agtggaaccc | ggtggccatg | 120 |
| tggagctggg | acgtggagtg | cgatacgtgc | gccatctgca | gggtccaggt | gatggatgcc | 180 |
| tgtcttagat | gtcaagctga | aaacaaacaa | gaggactgtg | ttgtggtctg | gggagaatgt | 240 |
| aatcattcct | tccacaactg | ctgcatgtcc | ctgtgggtga | aacagaacaa | tcgctgccct | 300 |
| ctctgccagc | aggactgggt | ggtccaaaga | atcggcaaat | ga | | 342 |

<210> SEQ ID NO 8
<211> LENGTH: 113
<212> TYPE: PRT
<213> ORGANISM: Homo sapiens

<400> SEQUENCE: 8

Met Ala Asp Val Glu Asp Gly Glu Glu Thr Cys Ala Leu Ala Ser His
1               5                   10                  15

Ser Gly Ser Ser Gly Ser Thr Ser Gly Gly Asp Lys Met Phe Ser Leu
            20                  25                  30

Lys Lys Trp Asn Pro Val Ala Met Trp Ser Trp Asp Val Glu Cys Asp
        35                  40                  45

Thr Cys Ala Ile Cys Arg Val Gln Val Met Asp Ala Cys Leu Arg Cys
    50                  55                  60

Gln Ala Glu Asn Lys Gln Glu Asp Cys Val Val Val Trp Gly Glu Cys
65                  70                  75                  80

Asn His Ser Phe His Asn Cys Cys Met Ser Leu Trp Val Lys Gln Asn
                85                  90                  95

Asn Arg Cys Pro Leu Cys Gln Gln Asp Trp Val Val Gln Arg Ile Gly
            100                 105                 110

Lys

<210> SEQ ID NO 9
<211> LENGTH: 2343
<212> TYPE: DNA
<213> ORGANISM: Homo sapiens

<400> SEQUENCE: 9

| | | | | | |
|---|---|---|---|---|---|
| atggcgacgt | ctaatctgtt | aaagaataaa | ggttctcttc | agtttgaaga | caaatgggat | 60 |
| tttatgcgcc | cgattgtttt | gaagctttta | cgccaggaat | ctgttacaaa | acagcagtgg | 120 |
| tttgatctgt | tttcggatgt | gcatgcagtc | tgtctttggg | atgataaagg | cccagcaaaa | 180 |
| attcatcagg | ctttaaaaga | agatattctt | gagtttatta | agcaggcaca | ggcacgagta | 240 |
| ctgagccatc | aagatgatac | ggctttgcta | aaagcatata | ttgttgaatg | gcgaaagttc | 300 |
| tttacacaat | gtgatatttt | accaaaacct | ttttgtcaac | tagagattac | tttaatgggt | 360 |
| aaacagggca | gcaataaaaa | atcaaatgtg | gaagacagta | ttgttcgaaa | gcttatgctt | 420 |
| gatacatgga | atgagtcaat | cttttcaaac | ataaaaaaca | gactccaaga | tagtgcaatg | 480 |
| aagctggtac | atgctgagag | attgggagaa | gcttttgatt | tcagctggt | tattggagta | 540 |
| agagaatcct | atgttaacct | tgttctaat | cctgaggata | aacttcaaat | ttatagggac | 600 |

```
aattttgaga aggcatactt ggattcaaca gagagatttt atagaacaca agcaccctcg      660
tatttacaac caaatggtgt acagaattat atgaaatatg cagatgctaa attaaaagaa      720
gaagaaaaac gagcactacg ttatttagaa acaagacgag aatgtaactc cgttgaagca      780
ctcatggaat gctgtgtaaa tgccctggtg acatcattta aagagactat cttagctgag      840
tgccaaggca tgatcaagag aaatgaaact gaaaaattac atttaatgtt ttcattgatg      900
gacaaagttc ctaatggtat agagccaatg ttgaaagact ggaggaaca tatcattagt       960 gctggcctgg cagatatggt agcagctgct gaaactatta ctactgactc tgagaaatac     1020
gttgagcagt tacttacact atttaataga tttagtaaac tcgtcaaaga agcttttcaa     1080
gatgatccac gatttcttac tgcaagagat aaggcgtata agcagttgt taatgatgct      1140 accatattta aacttgaatt acctttgaag cagaaggggg tgggattaaa aactcagcct     1200
gaatcaaaat gccctgagct gcttgccaat tactgtgaca tgttgctaag aaaaacacca     1260
ttaagcaaaa aactaacctc tgaagagatt gaagcaaagc ttaaagaagt gctcttggta     1320
cttaagtatg tacagaacaa agatgttttt atgaggtatc ataaagctca tttgacacga     1380
cgtcttatat tagacatctc tgccgatagt gaaattgaag aaaacatggt agagtggcta     1440
agagaagttg gtatgccagc ggattatgta aacaagcttg ctagaatgtt tcaggacata     1500
aaagtatctg aagatttgaa ccaagctttt aaggaaatgc acaaaaataa taaattggca     1560
ttaccagctg attcagttaa tataaaaatt ctgaatgctg gcgcctggtc aagaagttct     1620
gagaaagtct ttgtctcact tcctactgaa ctggaggact tgataccgga gtagaagaa      1680 ttctacaaaa aaaatcatag tggtagaaaa ttacattggc atcatctcat gtcaaatgga     1740
attataacat ttaagaatga agttggtcaa tatgatttgg aggtaaccac gtttcagctc     1800
gctgtattgt ttgcatggaa ccaaagaccc agagagaaaa tcagctttga aaatcttaag     1860
cttgcaactg aactccctga tgctgaactt aggaggactt tatggtcttt agtagctttc     1920
ccaaaactca acggcaagt tttttttgtat gaccctcaag tcaactcacc caaagacttt     1980
acagaaggta ccctcttctc agtgaaccag gagttcagtt taataaaaaa tgcaaaggtt     2040
cagaaaaggg gtaaaatcaa cttgattgga cgtttgcagc tcactacaga aaggatgaga     2100
gaagaagaga atgaaggaat agttcaacta cgaatactaa gaacccagga agctatcata     2160
caaataatga aaatgagaaa gaaaattagt aatgctcagc tgcagactga attagtagaa     2220
attttgaaaa acatgttctt gccacaaaag aaaatgataa agagcaaat agagtggcta     2280 atagagcaca atacatcag aagagatgaa tctgatatca cactttcat atatatggca     2340 taa                                                                 2343
```

<210> SEQ ID NO 10
<211> LENGTH: 861
<212> TYPE: PRT
<213> ORGANISM: Homo sapiens

<400> SEQUENCE: 10

Met Arg Ser Phe Ala Trp Gly Ser Ser Gly Asp His Val Gly Asp Lys
1               5                   10                  15

Ser Glu Glu Ala Pro Gly Ala Trp Asp Glu Val Ser Ala Val Gly Ala
            20                  25                  30

Leu Leu Gln Arg Pro Pro His Pro Gly Ala Gly Pro Thr Gly Pro Gly
        35                  40                  45

Pro Trp Trp Glu Leu Arg Pro Pro Val Lys Ala Trp Pro Gly Arg Glu
    50                  55                  60

-continued

```
Arg His Glu Phe Ser Arg Arg Leu Val Ser Arg Glu Ser Lys Leu Lys
 65                  70                  75                  80

Asn Met Ala Thr Ser Asn Leu Leu Lys Asn Lys Gly Ser Leu Gln Phe
                 85                  90                  95

Glu Asp Lys Trp Asp Phe Met Arg Pro Ile Val Leu Lys Leu Leu Arg
            100                 105                 110

Gln Glu Ser Val Thr Lys Gln Gln Trp Phe Asp Leu Phe Ser Asp Val
        115                 120                 125

His Ala Val Cys Leu Trp Asp Asp Lys Gly Pro Ala Lys Ile His Gln
    130                 135                 140

Ala Leu Lys Glu Asp Ile Leu Glu Phe Ile Lys Gln Ala Gln Ala Arg
145                 150                 155                 160

Val Leu Ser His Gln Asp Asp Thr Ala Leu Leu Lys Ala Tyr Ile Val
                165                 170                 175

Glu Trp Arg Lys Phe Phe Thr Gln Cys Asp Ile Leu Pro Lys Pro Phe
            180                 185                 190

Cys Gln Leu Glu Ile Thr Leu Met Gly Lys Gln Gly Ser Asn Lys Lys
        195                 200                 205

Ser Asn Val Glu Asp Ser Ile Val Arg Lys Leu Met Leu Asp Thr Trp
    210                 215                 220

Asn Glu Ser Ile Phe Ser Asn Ile Lys Asn Arg Leu Gln Asp Ser Ala
225                 230                 235                 240

Met Lys Leu Val His Ala Glu Arg Leu Gly Glu Ala Phe Asp Ser Gln
                245                 250                 255

Leu Val Ile Gly Val Arg Glu Ser Tyr Val Asn Leu Cys Ser Asn Pro
            260                 265                 270

Glu Asp Lys Leu Gln Ile Tyr Arg Asp Asn Phe Glu Lys Ala Tyr Leu
        275                 280                 285

Asp Ser Thr Glu Arg Phe Tyr Arg Thr Gln Ala Pro Ser Tyr Leu Gln
    290                 295                 300

Pro Asn Gly Val Gln Asn Tyr Met Lys Tyr Ala Asp Ala Lys Leu Lys
305                 310                 315                 320

Glu Glu Glu Lys Arg Ala Leu Arg Tyr Leu Glu Thr Arg Arg Glu Cys
                325                 330                 335

Asn Ser Val Glu Ala Leu Met Glu Cys Cys Val Asn Ala Leu Val Thr
            340                 345                 350

Ser Phe Lys Glu Thr Ile Leu Ala Glu Cys Gln Gly Met Ile Lys Arg
        355                 360                 365

Asn Glu Thr Glu Lys Leu His Leu Met Phe Ser Leu Met Asp Lys Val
    370                 375                 380

Pro Asn Gly Ile Glu Pro Met Leu Lys Asp Leu Glu Glu His Ile Ile
385                 390                 395                 400

Ser Ala Gly Leu Ala Asp Met Val Ala Ala Glu Thr Ile Thr Thr
                405                 410                 415

Asp Ser Glu Lys Tyr Val Glu Gln Leu Leu Thr Leu Phe Asn Arg Phe
        420                 425                 430

Ser Lys Leu Val Lys Glu Ala Phe Gln Asp Asp Pro Arg Phe Leu Thr
    435                 440                 445

Ala Arg Asp Lys Ala Tyr Lys Ala Val Val Asn Asp Ala Thr Ile Phe
450                 455                 460

Lys Leu Glu Leu Pro Leu Lys Gln Lys Gly Val Gly Leu Lys Thr Gln
465                 470                 475                 480
```

-continued

```
Pro Glu Ser Lys Cys Pro Glu Leu Leu Ala Asn Tyr Cys Asp Met Leu
            485                 490                 495

Leu Arg Lys Thr Pro Leu Ser Lys Lys Leu Thr Ser Glu Glu Ile Glu
            500                 505                 510

Ala Lys Leu Lys Glu Val Leu Leu Val Leu Lys Tyr Val Gln Asn Lys
            515                 520                 525

Asp Val Phe Met Arg Tyr His Lys Ala His Leu Thr Arg Arg Leu Ile
            530                 535                 540

Leu Asp Ile Ser Ala Asp Ser Glu Ile Glu Glu Asn Met Val Glu Trp
545                 550                 555                 560

Leu Arg Glu Val Gly Met Pro Ala Asp Tyr Val Asn Lys Leu Ala Arg
                565                 570                 575

Met Phe Gln Asp Ile Lys Val Ser Glu Asp Leu Asn Gln Ala Phe Lys
            580                 585                 590

Glu Met His Lys Asn Asn Lys Leu Ala Leu Pro Ala Asp Ser Val Asn
            595                 600                 605

Ile Lys Ile Leu Asn Ala Gly Ala Trp Ser Arg Ser Ser Glu Lys Val
            610                 615                 620

Phe Val Ser Leu Pro Thr Glu Leu Glu Asp Leu Ile Pro Glu Val Glu
625                 630                 635                 640

Glu Phe Tyr Lys Lys Asn His Ser Gly Arg Lys Leu His Trp His His
            645                 650                 655

Leu Met Ser Asn Gly Ile Ile Thr Phe Lys Asn Glu Val Gly Gln Tyr
            660                 665                 670

Asp Leu Glu Val Thr Thr Phe Gln Leu Ala Val Leu Phe Ala Trp Asn
            675                 680                 685

Gln Arg Pro Arg Glu Lys Ile Ser Phe Glu Asn Leu Lys Leu Ala Thr
            690                 695                 700

Glu Leu Pro Asp Ala Glu Leu Arg Arg Thr Leu Trp Ser Leu Val Ala
705                 710                 715                 720

Phe Pro Lys Leu Lys Arg Gln Val Phe Leu Tyr Asp Pro Gln Val Asn
            725                 730                 735

Ser Pro Lys Asp Phe Thr Glu Gly Thr Leu Phe Ser Val Asn Gln Glu
            740                 745                 750

Phe Ser Leu Ile Lys Asn Ala Lys Val Gln Lys Arg Gly Lys Ile Asn
            755                 760                 765

Leu Ile Gly Arg Leu Gln Leu Thr Thr Glu Arg Met Arg Glu Glu Glu
            770                 775                 780

Asn Glu Gly Ile Val Gln Leu Arg Ile Leu Arg Thr Gln Glu Ala Ile
785                 790                 795                 800

Ile Gln Ile Met Lys Met Arg Lys Lys Ile Ser Asn Ala Gln Leu Gln
            805                 810                 815

Thr Glu Leu Val Glu Ile Leu Lys Asn Met Phe Leu Pro Gln Lys Lys
            820                 825                 830

Met Ile Lys Glu Gln Ile Glu Trp Leu Ile Glu His Lys Tyr Ile Arg
            835                 840                 845

Arg Asp Glu Ser Asp Ile Asn Thr Phe Ile Tyr Met Ala
            850                 855                 860
```

<210> SEQ ID NO 11
<211> LENGTH: 2469
<212> TYPE: DNA
<213> ORGANISM: Homo sapiens

<400> SEQUENCE: 11

-continued

| | |
|---|---:|
| atggcggcgg cagttgtggt ggcggagggg gacagcgact cccggcccgg acaggagttg | 60 |
| ttagtggcct ggaacaccgt gagcaccggc ctggtgccgc cggctgcgct ggggctggtg | 120 |
| tcttcccgga ccagcggtgc agtcccgcca aggaagagg agctccgggc ggcggtggag | 180 |
| gttctgaggg gccacgggct acactcggtc ctggaggagt ggttcgtgga ggtgctgcag | 240 |
| aacgatctgc aggccaacat ctcccctgag ttctggaatg ccatctccca atgcgagaac | 300 |
| tctgcggatg agccccagtg cctttttgcta ctccttgacg cttttggcct gctggagagc | 360 |
| cgcctggatc cctacctgcg tagcctagag ctgctggaga atggactcg cctgggcttg | 420 |
| ctgatgggca ctggtgctca ggggctgcga agaagtcc acactatgtt gcgcggagtc | 480 |
| ttgttcttta gcaccccag aaccttccaa gagatgatcc agcgtctgta tgggtgcttc | 540 |
| ttgagagtct atatgcagag taagaggaag ggggaagggg gcacagaccc ggaactggaa | 600 |
| ggggagctgg acagccggta tgcccgtcgc cggtactacc ggctcctgca gagcccgctg | 660 |
| tgtgcagggt gcagcagtga caagcaacag tgctggtgtc gccaggctct ggagcagttc | 720 |
| catcagctca gccaggtctt acacaggctc agtctgctgg agcgggtcag tgccgaggct | 780 |
| gtgaccacca ccctgcacca ggtgacccgg gagaggatga aggaccgttg ccggggcgag | 840 |
| tacgagcgct cttcctgcg tgagttccac aagtggatcg agcgggtggt cggctggctc | 900 |
| ggcaaggtgt tcctgcagga cggccccgcc aggcccgcat ctcccgaggc cggcaacacc | 960 |
| ctgcgccgct ggcgctgcca cgtgcaaagg ttcttctacc gcatctacgc cagcctgcgc | 1020 |
| atcgaggagc tcttcagcat cgtccgagac ttcccagact cccggccagc catcgaggac | 1080 |
| ctcaagtact gcctggagag gacgaccag aggcagcagc tgctcgtgtc cctcaaggct | 1140 |
| gccctggaga ctcggctcct gcatccaggc gtcaacacgt gtgacatcat caccctctat | 1200 |
| atctctgcca tcaaggcgct gcgcgtgctg gaccccttca tggtcatcct ggaggtggcc | 1260 |
| tgtgagccta tccgccgcta cctgaggacg cgggaggaca cagtgcggca gattgtggct | 1320 |
| gggctgacgg gggactcgga cgggacaggg gacctggctg ttgagctgtc caagaccgac | 1380 |
| ccggcgagcc tggagacagg ccaggacagt gaggatgact caggcgagcc agaggactgg | 1440 |
| gtccccggacc ctgtggatgc cgatccaggg aagtcgagct ccaagcggcg ttcatcggac | 1500 |
| atcatcagcc tgctggtcag catctacggc agcaaggacc tcttcatcaa tgagtaccgc | 1560 |
| tcgctgctgg ccgaccgcct gctgcaccag ttcagcttca gccccgagcg ggagatccgc | 1620 |
| aacgtggagc tgctgaagct gcgctttggc gaggccccaa tgcacttctg tgaagtcatg | 1680 |
| ctgaaggaca tggcggactc ccgccgcatc aatgccaaca tccgggagga ggatgagaag | 1740 |
| cggccagcag aggagcagcc accgttcggg gtctacgctg tcatcctgtc cagtgagttc | 1800 |
| tggccgccct tcaaggacga gaagctggag gtccccgagg atatcagggc agccctggag | 1860 |
| gcttactgca agaagtatga gcagctcaag gccatgcgga ccctcagttg aagcacacc | 1920 |
| ctgggcctgg tgaccatgga cgtggagctg gccgaccgca cgctgtctgt ggcggtcacc | 1980 |
| ccagtacagg cggtgatctt gctgtatttt caggaccaag ccagctggac cctgaggaa | 2040 |
| ctgagcaagg cggtgaaaat gccgtggcg ctgctgcggc ggcggatgtc cgtgtggctg | 2100 |
| cagcagggtg tgctgcgtga ggagccccc ggcaccttct ctgtcattga ggaggagcgg | 2160 |
| cctcaggacc gggacaacat ggtgctcatt gacagtgacg acgagagcga ctccggcatg | 2220 |
| gcctcccagg ccgaccagaa ggaggaggag ctgctgctct ctggacgta catccaggcc | 2280 |
| atgctgacca acctggagag cctctcactg gatcgtatct acaacatgct ccgcatgttt | 2340 |

-continued

```
gtggtgactg ggcctgcact ggccgagatt gacctgcagg agctgcaggg ctacctgcag    2400
aagaaggtgc gggaccagca gctcgtctac tcggccggcg tctaccgcct gcccaagaac    2460
tgcagctga                                                            2469
```

<210> SEQ ID NO 12
<211> LENGTH: 822
<212> TYPE: PRT
<213> ORGANISM: Homo sapiens

<400> SEQUENCE: 12

```
Met Ala Ala Val Val Ala Glu Gly Asp Ser Asp Ser Arg Pro
1               5                   10                  15

Gly Gln Glu Leu Leu Val Ala Trp Asn Thr Val Ser Thr Gly Leu Val
                20                  25                  30

Pro Pro Ala Ala Leu Gly Leu Val Ser Ser Arg Thr Ser Gly Ala Val
            35                  40                  45

Pro Pro Lys Glu Glu Leu Arg Ala Ala Val Glu Val Leu Arg Gly
        50                  55                  60

His Gly Leu His Ser Val Leu Glu Glu Trp Phe Val Glu Val Leu Gln
65                  70                  75                  80

Asn Asp Leu Gln Ala Asn Ile Ser Pro Glu Phe Trp Asn Ala Ile Ser
                85                  90                  95

Gln Cys Glu Asn Ser Ala Asp Glu Pro Gln Cys Leu Leu Leu Leu
            100                 105                 110

Asp Ala Phe Gly Leu Leu Glu Ser Arg Leu Asp Pro Tyr Leu Arg Ser
        115                 120                 125

Leu Glu Leu Leu Glu Lys Trp Thr Arg Leu Gly Leu Leu Met Gly Thr
    130                 135                 140

Gly Ala Gln Gly Leu Arg Glu Glu Val His Thr Met Leu Arg Gly Val
145                 150                 155                 160

Leu Phe Phe Ser Thr Pro Arg Thr Phe Gln Glu Met Ile Gln Arg Leu
                165                 170                 175

Tyr Gly Cys Phe Leu Arg Val Tyr Met Gln Ser Lys Arg Lys Gly Glu
            180                 185                 190

Gly Gly Thr Asp Pro Glu Leu Glu Gly Glu Leu Asp Ser Arg Tyr Ala
        195                 200                 205

Arg Arg Arg Tyr Tyr Arg Leu Leu Gln Ser Pro Leu Cys Ala Gly Cys
    210                 215                 220

Ser Ser Asp Lys Gln Gln Cys Trp Cys Arg Gln Ala Leu Glu Gln Phe
225                 230                 235                 240

His Gln Leu Ser Gln Val Leu His Arg Leu Ser Leu Glu Arg Val
                245                 250                 255

Ser Ala Glu Ala Val Thr Thr Thr Leu His Gln Val Thr Arg Glu Arg
            260                 265                 270

Met Glu Asp Arg Cys Arg Gly Glu Tyr Glu Arg Ser Phe Leu Arg Glu
        275                 280                 285

Phe His Lys Trp Ile Glu Arg Val Val Gly Trp Leu Gly Lys Val Phe
    290                 295                 300

Leu Gln Asp Gly Pro Ala Arg Pro Ala Ser Pro Glu Ala Gly Asn Thr
305                 310                 315                 320

Leu Arg Arg Trp Arg Cys His Val Gln Arg Phe Phe Tyr Arg Ile Tyr
                325                 330                 335

Ala Ser Leu Arg Ile Glu Glu Leu Phe Ser Ile Val Arg Asp Phe Pro
            340                 345                 350
```

-continued

```
Asp Ser Arg Pro Ala Ile Glu Asp Leu Lys Tyr Cys Leu Glu Arg Thr
            355                 360                 365

Asp Gln Arg Gln Gln Leu Leu Val Ser Leu Lys Ala Ala Leu Glu Thr
            370                 375                 380

Arg Leu Leu His Pro Gly Val Asn Thr Cys Asp Ile Ile Thr Leu Tyr
385                 390                 395                 400

Ile Ser Ala Ile Lys Ala Leu Arg Val Leu Asp Pro Ser Met Val Ile
                405                 410                 415

Leu Glu Val Ala Cys Glu Pro Ile Arg Arg Tyr Leu Arg Thr Arg Glu
            420                 425                 430

Asp Thr Val Arg Gln Ile Val Ala Gly Leu Thr Gly Asp Ser Asp Gly
            435                 440                 445

Thr Gly Asp Leu Ala Val Glu Leu Ser Lys Thr Asp Pro Ala Ser Leu
450                 455                 460

Glu Thr Gly Gln Asp Ser Glu Asp Asp Ser Gly Glu Pro Glu Asp Trp
465                 470                 475                 480

Val Pro Asp Pro Val Asp Ala Asp Pro Gly Lys Ser Ser Ser Lys Arg
            485                 490                 495

Arg Ser Ser Asp Ile Ile Ser Leu Leu Val Ser Ile Tyr Gly Ser Lys
            500                 505                 510

Asp Leu Phe Ile Asn Glu Tyr Arg Ser Leu Leu Ala Asp Arg Leu Leu
            515                 520                 525

His Gln Phe Ser Phe Ser Pro Glu Arg Glu Ile Arg Asn Val Glu Leu
            530                 535                 540

Leu Lys Leu Arg Phe Gly Glu Ala Pro Met His Phe Cys Glu Val Met
545                 550                 555                 560

Leu Lys Asp Met Ala Asp Ser Arg Arg Ile Asn Ala Asn Ile Arg Glu
                565                 570                 575

Glu Asp Glu Lys Arg Pro Ala Glu Glu Gln Pro Pro Phe Gly Val Tyr
            580                 585                 590

Ala Val Ile Leu Ser Ser Glu Phe Trp Pro Pro Phe Lys Asp Glu Lys
            595                 600                 605

Leu Glu Val Pro Glu Asp Ile Arg Ala Ala Leu Glu Ala Tyr Cys Lys
            610                 615                 620

Lys Tyr Glu Gln Leu Lys Ala Met Arg Thr Leu Ser Trp Lys His Thr
625                 630                 635                 640

Leu Gly Leu Val Thr Met Asp Val Glu Leu Ala Asp Arg Thr Leu Ser
                645                 650                 655

Val Ala Val Thr Pro Val Gln Ala Val Ile Leu Leu Tyr Phe Gln Asp
            660                 665                 670

Gln Ala Ser Trp Thr Leu Glu Glu Leu Ser Lys Ala Val Lys Met Pro
            675                 680                 685

Val Ala Leu Leu Arg Arg Arg Met Ser Val Trp Leu Gln Gln Gly Val
            690                 695                 700

Leu Arg Glu Glu Pro Pro Gly Thr Phe Ser Val Ile Glu Glu Arg
705                 710                 715                 720

Pro Gln Asp Arg Asp Asn Met Val Leu Ile Asp Ser Asp Asp Glu Ser
            725                 730                 735

Asp Ser Gly Met Ala Ser Gln Ala Asp Lys Glu Glu Glu Leu Leu
            740                 745                 750

Leu Phe Trp Thr Tyr Ile Gln Ala Met Leu Thr Asn Leu Glu Ser Leu
            755                 760                 765
```

```
Ser Leu Asp Arg Ile Tyr Asn Met Leu Arg Met Phe Val Thr Gly
    770                 775                 780
Pro Ala Leu Ala Glu Ile Asp Leu Gln Glu Leu Gln Gly Tyr Leu Gln
785                 790                 795                 800
Lys Lys Val Arg Asp Gln Gln Leu Val Tyr Ser Ala Gly Val Tyr Arg
                805                 810                 815
Leu Pro Lys Asn Cys Ser
            820

<210> SEQ ID NO 13
<211> LENGTH: 76
<212> TYPE: PRT
<213> ORGANISM: Homo sapiens

<400> SEQUENCE: 13

Met Gln Ile Phe Val Lys Thr Leu Thr Gly Lys Thr Ile Thr Leu Glu
1               5                   10                  15
Val Glu Pro Ser Asp Thr Ile Glu Asn Val Lys Ala Lys Ile Gln Asp
                20                  25                  30
Lys Glu Gly Ile Pro Pro Asp Gln Gln Arg Leu Ile Phe Ala Gly Lys
            35                  40                  45
Gln Leu Glu Asp Gly Arg Thr Leu Ser Asp Tyr Asn Ile Gln Lys Glu
    50                  55                  60
Ser Thr Leu His Leu Val Leu Arg Leu Arg Gly Gly
65                  70                  75

<210> SEQ ID NO 14
<211> LENGTH: 84
<212> TYPE: PRT
<213> ORGANISM: Artificial sequence
<220> FEATURE:
<223> OTHER INFORMATION: Flag-ubiquitin

<400> SEQUENCE: 14

Met Asp Tyr Lys Asp Asp Asp Lys Gln Ile Phe Val Lys Thr Leu
1               5                   10                  15
Thr Gly Lys Thr Ile Thr Leu Glu Val Glu Pro Ser Asp Thr Ile Glu
                20                  25                  30
Asn Val Lys Ala Lys Ile Gln Asp Lys Glu Gly Ile Pro Pro Asp Gln
            35                  40                  45
Gln Arg Leu Ile Phe Ala Gly Lys Gln Leu Glu Asp Gly Arg Thr Leu
    50                  55                  60
Ser Asp Tyr Asn Ile Gln Lys Glu Ser Thr Leu His Leu Val Leu Arg
65                  70                  75                  80
Leu Arg Gly Gly

<210> SEQ ID NO 15
<211> LENGTH: 85
<212> TYPE: PRT
<213> ORGANISM: Artificial sequence
<220> FEATURE:
<223> OTHER INFORMATION: Flag-Cys-ubiquitin

<400> SEQUENCE: 15

Met Asp Tyr Lys Asp Asp Asp Lys Cys Gln Ile Phe Val Lys Thr
1               5                   10                  15
Leu Thr Gly Lys Thr Ile Thr Leu Glu Val Glu Pro Ser Asp Thr Ile
                20                  25                  30
Glu Asn Val Lys Ala Lys Ile Gln Asp Lys Glu Gly Ile Pro Pro Asp
```

```
                35                    40                   45
Gln Gln Arg Leu Ile Phe Ala Gly Lys Gln Leu Glu Asp Gly Arg Thr
    50                   55                   60

Leu Ser Asp Tyr Asn Ile Gln Lys Glu Ser Thr Leu His Leu Val Leu
65                   70                   75                   80

Arg Leu Arg Gly Gly
                85

<210> SEQ ID NO 16
<211> LENGTH: 170
<212> TYPE: PRT
<213> ORGANISM: Homo sapiens

<400> SEQUENCE: 16

Met Thr Glu Leu Gln Ser Ala Leu Leu Leu Arg Arg Gln Leu Ala Glu
1               5                   10                  15

Leu Asn Lys Asn Pro Val Glu Gly Phe Ser Ala Gly Leu Ile Asp Asp
                20                  25                  30

Asn Asp Leu Tyr Arg Trp Glu Val Leu Ile Ile Gly Pro Pro Asp Thr
            35                  40                  45

Leu Tyr Glu Gly Gly Val Phe Lys Ala His Leu Thr Phe Pro Lys Asp
    50                  55                  60

Tyr Pro Leu Arg Pro Pro Lys Met Lys Phe Ile Thr Glu Ile Trp His
65                  70                  75                  80

Pro Asn Val Asp Lys Asn Gly Asp Val Cys Ile Ser Ile Leu His Glu
                85                  90                  95

Pro Gly Glu Asp Lys Tyr Gly Tyr Glu Lys Pro Glu Glu Arg Trp Leu
            100                 105                 110

Pro Ile His Thr Val Glu Thr Ile Met Ile Ser Val Ile Ser Met Leu
    115                 120                 125

Ala Asp Pro Asn Gly Asp Ser Pro Ala Asn Val Asp Ala Ala Lys Glu
    130                 135                 140

Trp Arg Glu Asp Arg Asn Gly Glu Phe Lys Arg Lys Val Ala Arg Cys
145                 150                 155                 160

Val Arg Lys Ser Gln Glu Thr Ala Phe Glu
                165                 170

<210> SEQ ID NO 17
<211> LENGTH: 513
<212> TYPE: DNA
<213> ORGANISM: Homo sapiens

<400> SEQUENCE: 17
atgacggagc tgcagtcggc actgctactg cgaagacagc tggcagaact caacaaaaat    60
ccagtggaag ctttttctgc aggtttaata gatgacaatg atctctaccg atgggaagtc   120
cttattattg gccctccaga tacactttat gaaggtggtg tttttaaggc tcatcttact   180
ttcccaaaag attatcccct ccgacctcct aaaatgaaat tcattacaga aatctggcac   240
ccaaatgttg ataaaaatgg tgatgtgtgc atttctattc ttcatgagcc tggggaagat   300
aagtatggtt atgaaaagcc agaggaacgc tggctcccta tccacactgt ggaaaccatc   360
atgattagtg tcatttctat gctggcagac cctaatggag actcacctgc taatgttgat   420
gctgcgaaag aatggaggga agatagaaat ggagaattta aagaaaagt tgcccgctgt   480 gtaagaaaaa gccaagagac tgcttttgag tga                                513
```

<210> SEQ ID NO 18
<211> LENGTH: 165
<212> TYPE: PRT
<213> ORGANISM: Homo sapiens

<400> SEQUENCE: 18

```
Met Ala Gly Thr Ala Leu Lys Arg Leu Met Ala Glu Tyr Lys Gln Leu
1               5                   10                  15

Thr Leu Asn Pro Pro Glu Gly Ile Val Ala Gly Pro Met Asn Glu Glu
            20                  25                  30

Asn Phe Phe Glu Trp Glu Ala Leu Ile Met Gly Pro Glu Asp Thr Cys
        35                  40                  45

Phe Glu Phe Gly Val Phe Pro Ala Ile Leu Ser Phe Pro Leu Asp Tyr
    50                  55                  60

Pro Leu Ser Pro Pro Lys Met Arg Phe Thr Cys Glu Met Phe His Pro
65                  70                  75                  80

Asn Ile Tyr Pro Asp Gly Arg Val Cys Ile Ser Ile Leu His Ala Pro
                85                  90                  95

Gly Asp Asp Pro Met Gly Tyr Glu Ser Ser Ala Glu Arg Trp Ser Pro
            100                 105                 110

Val Gln Ser Val Glu Lys Ile Leu Leu Ser Val Val Ser Met Leu Ala
        115                 120                 125

Glu Pro Asn Asp Glu Ser Gly Ala Asn Val Asp Ala Ser Lys Met Trp
    130                 135                 140

Arg Asp Asp Arg Glu Gln Phe Tyr Lys Ile Ala Lys Gln Ile Val Gln
145                 150                 155                 160

Lys Ser Leu Gly Leu
                165
```

<210> SEQ ID NO 19
<211> LENGTH: 2878
<212> TYPE: DNA
<213> ORGANISM: Homo sapiens

<400> SEQUENCE: 19

| | | | | | |
|---|---|---|---|---|---|
| cgcgcggctg | aggcgaggtc | gctcggcgca | gctgttgcgg | ggccatggcg | gggaccgcgc | 60 |
| tcaagaggct | gatggccgag | tacaaacaat | taacactgaa | tcctccggaa | ggaattgtag | 120 |
| caggccccat | gaatgaagag | aacttttttg | aatgggaggc | attgatcatg | ggcccagaag | 180 |
| acacctgctt | tgagtttggt | gttttttcctg | ccatcctgag | tttcccactt | gattaccccgt | 240 |
| taagtccccc | aaagatgaga | tttacctgtg | agatgtttca | tcccaacatc | taccctgatg | 300 |
| ggagagtctg | catttccatc | ctccacgcgc | caggcgatga | ccccatgggc | tacgagagca | 360 |
| gcgcggagcg | gtggagtcct | gtgcagagtg | tggagaagat | cctgctgtcg | gtggtgagca | 420 |
| tgctggcaga | gcccaatgac | gaaagtggag | ctaacgtgga | tgcgtccaaa | atgtggcgcg | 480 |
| atgaccggga | gcagttctat | aagattgcca | agcagatcgt | ccagaagtct | ctgggactgt | 540 |
| gagacctggc | ctcgcacagg | cgcgcacaca | ccgccaagca | gctcagcatt | ctcccccggc | 600 |
| acacttagtg | acagtgatgc | tctgtgctgg | taccaaacaa | ggcagacttg | caagaaccat | 660 |
| ggcatctttt | ttttttttca | aacctttcct | acttcaaaca | ggcttctctt | ctgaaatgat | 720 |
| gacttaatgt | cgaatattga | cagcttactg | cagtttttaca | gtattcctca | caagggcttt | 780 |
| caggtagatt | atcagagctg | tcagcactac | ctctccccgc | tgaaaccagc | agttcatggc | 840 |
| ttcctgtgga | ttccctcccct | ccctggagtg | ttgaggggggt | tgtacctgcc | agacttccag | 900 |
| gggacgatgg | aatacccaga | acgctccttc | tgaagaaatg | gggccctgta | gctgcagcac | 960 |

```
agggggaaggg cccggcaccc tttctgggtc cttcctggtt ccctgtgggc cccatgagga   1020
gtccattact tcctttcttc cttcatattt tacaggcaga tgcttttctt ataatctaat   1080
tacatctttt catttgttat atattacaaa ccatcacact tagaaatact tccaggaaat   1140 gctttttttga agtgtgaatt aataagaaat ggggtaaata gaaagaaat ttattgctga   1200 ttggccaggt gcggtggttc gtgcctgtaa tcccagctct tgggaggcc aaggcaggta   1260 gatcacaagg tcaggaaatt gagaccatcc tggctaatac agtgaaaccc catgtctgct   1320
aaaattacaa aaaattagct gggcgtggtg gtgcacgcct gtagtctcag ctactcagga   1380
ggctgaggca ggagaatcgc ttgaacccgg gaggcagagg tagcagtgag ctgaagtccc   1440
gccactgcac tccagcctgg gcaacagagc gagactcagt ctcaaaaaga aaaagaaat   1500 ttattgctga tcacaaggac agacagtttt ttcccgacca tactcatcaa agatttacgt   1560
ttgtatatta gtaactagtg cattactaga gcaggtgcag gtgaggtctt taaagtttca   1620
atgaaagttt cttctggatc tacagaaaaa attttttttt ttcaatctaa aaactggaaa   1680
ttctagggtt tttgtacatt ttggatgcac tgggaattta ttagcacaaa atcattcttt   1740
gcaactcaaa attcagaagg gactctacca tatcttagct cagagcacag aggagtgcct   1800
tatccccaca cttgactggg ctgtggaggt gggcatgtgg gcccctgggc ccaggctggg   1860
gacagagccc ttgttttgtg acttaggatt ttgatgtggt tcccatgttc tctaacaggg   1920
ccagctgagc agcacaggcc aggaggccac agtgtaagca ataacagatc tgccacatgc   1980
agaagcaaat atcaggcctg tcgcacacgg gcggcattta aataggaatt tctattttg   2040 aaataaggga tggtctatga ggcatacagt agatttgatg tgatccttt ctccctccct   2100 tccataatgg atcgtggtct gtgtgactga acccacacag agtgtcatgg gtgacagttt   2160
ctggttgaag tagctccacg cctggcttct gtggacagca gattcttttc cttctcacaa   2220
ggggctcatt taaaatttgg aggctgggtg ctgtggctca cgcctgcaat cccagcactt   2280
tgggagactg aggcgggcgg atcatgaggt caggagatcg cgaccatcct ggctaacagt   2340
gaaaccctgt ctccactaaa aatacaaaaa attagccggg cgtggtggcg ggcgcctgta   2400
gtcccagcta ctctgaagac tgaggcagga gaatggcgtg aacccaggag gcggagcttg   2460
cagtgagctg agatcacgcc actgcactcc agcctgggca acagagtgag actctgtctc   2520
aaaaaaaaaa aaaaaaaaaa tggaacgcag ggcaagaact cgtatttgga aggagatggg   2580
ggaaaggagc ggtattatac ctatgttgta tttgcaggca aatgagatgg agccctctct   2640
gtaaagaaga gtcatttgtg caagtagacg gggtctgtgg gtgcaggccc tggagggca   2700 cacaattgcc tggaggcttc tgtgagatcg ggagagggag gagaggcagt ctcttgacaa   2760
aataaagtat tttattcat ttgtatttat taaatgaaaa aacaatccca tggtgtccct   2820
gttgtgtggt ggaacctaat gactgttgaa ataaagttct gtgttttccc tgccctgc    2878
```

<210> SEQ ID NO 20
<211> LENGTH: 158
<212> TYPE: PRT
<213> ORGANISM: Homo sapiens

<400> SEQUENCE: 20

```
Met Ser Gly Ile Ala Leu Ser Arg Leu Ala Gln Glu Arg Lys Ala Trp
1               5                   10                  15

Arg Lys Asp His Pro Phe Gly Phe Val Ala Val Pro Thr Lys Asn Pro
            20                  25                  30
```

```
Asp Gly Thr Met Asn Leu Met Asn Trp Glu Cys Ala Ile Pro Gly Lys
        35                  40                  45
Lys Gly Thr Pro Trp Glu Gly Gly Leu Phe Lys Leu Arg Met Leu Phe
 50                  55                  60
Lys Asp Asp Tyr Pro Ser Ser Pro Pro Lys Cys Lys Phe Glu Pro Pro
 65                  70                  75                  80
Leu Phe His Pro Asn Val Tyr Pro Ser Gly Thr Val Cys Leu Ser Ile
                 85                  90                  95
Leu Glu Glu Asp Lys Asp Trp Arg Pro Ala Ile Thr Ile Lys Gln Ile
                100                 105                 110
Leu Leu Gly Ile Gln Glu Leu Leu Asn Glu Pro Asn Ile Gln Asp Pro
            115                 120                 125
Ala Gln Ala Glu Ala Tyr Thr Ile Tyr Cys Gln Asn Arg Val Glu Tyr
        130                 135                 140
Glu Lys Arg Val Arg Ala Gln Ala Lys Lys Phe Ala Pro Ser
145                 150                 155

<210> SEQ ID NO 21
<211> LENGTH: 1856
<212> TYPE: DNA
<213> ORGANISM: Homo sapiens

<400> SEQUENCE: 21
ggatgggaag cgagcatggt gagtcctcaa gtcgcagctg ggcctgccac gtgggagtgg       60
agggtggagg aacgtgtgga gtttcggagt ccagcccagt gcgagacagc cttgaaaccg      120
tggttggcgg gcgctccact ccgctctggg ctcgaaccct gcctgaccct agctgtgccc      180
cccactttct ccctgtctgg ccctgctcc cgccccctc acttagagga gggcacgggg       240
aagggcaaac ggtccagagg gcgggcggct gcgggctcct ctgcatcatg tgaggagggc      300
gtggggaagg acatcctggt gggggcccgat ctgggctgcc tccagcccgg gcctgtgtct      360
tggacttagt cgtggacctg gaggccagtg cccggctggc cctgtcaccc tctcgctgtg      420
acgccagcgc ctgctgactg gaggacccag gttccttcgc ctgcttttc tcaggctgcc       480 ctgaggatct gtgtttggtg aaaaggagcc aaattcacct gcaggcagg cggctctagc       540 agcttcagaa gcctggtgcc ctggcgacac tggacctgcc ttggcttctt tgatcccaac      600 cccaccccg atttctgctc tgctgactgg ggaagtcatc gtgccaccca gaacctgagt       660
gcgggcctct cagagctcct tcgtccgtgg gtctgccggg gactgggcct tgtctccctg      720
gcgagtgcca ggtgaggctg cggcggctcc gacgcaggtg gagctgctga cctggcccct      780
ttctgcggct gcgagggact ttgaacatgt cggggatcgc cctcagcaga ctcgcccagg      840
agaggaaagc atggaggaaa gaccacccat ttggtttcgt ggctgtccca acaaaaaatc      900
ccgatggcac gatgaacctc atgaactggg agtgcgccat tccaggaaag aaagggactc      960
cgtgggaagg aggcttgttt aaactacgga tgcttttcaa agatgattat ccatcttcgc     1020
caccaaaatg taaattcgaa ccaccattat ttcacccgaa tgtgtaccct tcggggacag     1080
tgtgcctgtc catcttagag gaggacaagg actggaggcc agccatcaca atcaaacaga     1140
tcctattagg aatacaggaa cttctaaatg aaccaaatat ccaagaccca gctcaagcag     1200
aggcctacac gatttactgc caaaacagag tggagtacga gaaaagggtc cgagcacaag     1260
ccaagaagtt tgcgccctca taagcagcga ccttgtggca tcgtcagaag gaagggattg     1320
gtttggcaag aacttgttta caacattttt gcaaatctaa agttgctcca tacaatgact     1380
agtcacctgg gggggttggg cgggcgccat cttccattgc cgccgcgggt gtgcggtctc     1440
```

```
gattcgctga attgcccgtt tccatacagg gtctcttcct tcggtctttt gtattttga      1500 ttgttatgta aaactcgctt ttattttaat attgatgtca gtatttcaac tgctgtaaaa      1560
ttataaactt ttatacttgg gtaagtcccc caggcgagtt cctcgctctg ggatgcaggc      1620
atgcttctca ccgtgcagag ctgcacttgg cctcagctgg ctgtatggaa atgcaccctc      1680
cctcctgcgc tcctctctag aacctgggct gtgctgcttt tgagcctcag accccagggc      1740
agcatctcgg ttctgcgcca cttcctttgt gtttatatgg cgttttgtct gtgttgctgt      1800
ttaggtaaat aaactgttta tataaaaaaa aaaaaaaaaa aaaaaaaaaa aaaaaa          1856
```

<210> SEQ ID NO 22
<211> LENGTH: 179
<212> TYPE: PRT
<213> ORGANISM: Homo sapiens

<400> SEQUENCE: 22

```
Met Ala Ser Gln Asn Arg Asp Pro Ala Ala Thr Ser Val Ala Ala Ala
1               5                   10                  15

Arg Lys Gly Ala Glu Pro Ser Gly Gly Ala Ala Arg Gly Pro Val Gly
            20                  25                  30

Lys Arg Leu Gln Gln Glu Leu Met Thr Leu Met Met Ser Gly Asp Lys
        35                  40                  45

Gly Ile Ser Ala Phe Pro Glu Ser Asp Asn Leu Phe Lys Trp Val Gly
    50                  55                  60

Thr Ile His Gly Ala Ala Gly Thr Val Tyr Glu Asp Leu Arg Tyr Lys
65                  70                  75                  80

Leu Ser Leu Glu Phe Pro Ser Gly Tyr Pro Tyr Asn Ala Pro Thr Val
                85                  90                  95

Lys Phe Leu Thr Pro Cys Tyr His Pro Asn Val Asp Thr Gln Gly Asn
            100                 105                 110

Ile Cys Leu Asp Ile Leu Lys Glu Lys Trp Ser Ala Leu Tyr Asp Val
        115                 120                 125

Arg Thr Ile Leu Leu Ser Ile Gln Ser Leu Leu Gly Glu Pro Asn Ile
    130                 135                 140

Asp Ser Pro Leu Asn Thr His Ala Ala Glu Leu Trp Lys Asn Pro Thr
145                 150                 155                 160

Ala Phe Lys Lys Tyr Leu Gln Glu Thr Tyr Ser Lys Gln Val Thr Ser
                165                 170                 175

Gln Glu Pro
```

<210> SEQ ID NO 23
<211> LENGTH: 783
<212> TYPE: DNA
<213> ORGANISM: Homo sapiens

<400> SEQUENCE: 23

```
ggcacgagcg agttcctgtc tctctgccaa cgccgcccgg atggcttccc aaaaccgcga       60
cccagccgcc actagcgtcg ccgccgcccg taaggagct gagccgagcg ggggcgccgc       120
ccggggtccg gtgggcaaaa ggctacagca ggagctgatg accctcatga tgtctggcga      180
taaagggatt tctgccttcc ctgaatcaga caaccttttc aaatgggtag gaccatcca       240 tggagcagct ggaacagtat atgaagacct gaggtataag ctctcgctag agttccccag      300
tggctaccct tacaatgcgc ccacagtgaa gttcctcacg ccctgctatc accccaacgt      360
ggacacccag ggtaacatat gcctggacat cctgaaggaa aagtggtctg ccctgtatga      420
```

-continued

```
tgtcaggacc attctgctct ccatccagag ccttctagga gaacccaaca ttgatagtcc    480
cttgaacaca catgctgccg agctctggaa aaaccccaca gcttttaaga agtacctgca    540
agaaacctac tcaaagcagg tcaccagcca ggagccctga cccaggctgc ccagcctgtc    600
cttgtgtcgt cttttttaatt tttccttaga tggtctgtcc tttttgtgat ttctgtatag   660
gactctttat cttgagctgt ggtattttttg ttttgttttt gtcttttaaa ttaagcctcg   720
gttgagccct tgtatattaa ataaatgcat ttttgtcctt ttttaaaaaa aaaaaaaaaa   780
aaa                                                                  783
```

<210> SEQ ID NO 24
<211> LENGTH: 152
<212> TYPE: PRT
<213> ORGANISM: Homo sapiens

<400> SEQUENCE: 24

```
Met Ala Gly Leu Pro Arg Arg Ile Ile Lys Glu Thr Gln Arg Leu Leu
1               5                   10                  15

Ala Glu Pro Val Pro Gly Ile Lys Ala Glu Pro Asp Glu Ser Asn Ala
            20                  25                  30

Arg Tyr Phe His Val Val Ile Ala Gly Pro Gln Asp Ser Pro Phe Glu
        35                  40                  45

Gly Gly Thr Phe Lys Leu Glu Leu Phe Leu Pro Glu Glu Tyr Pro Met
    50                  55                  60

Ala Ala Pro Lys Val Arg Phe Met Thr Lys Ile Tyr His Pro Asn Val
65                  70                  75                  80

Asp Lys Leu Gly Arg Ile Cys Leu Asp Ile Leu Lys Asp Lys Trp Ser
                85                  90                  95

Pro Ala Leu Gln Ile Arg Thr Val Leu Leu Ser Ile Gln Ala Leu Leu
            100                 105                 110

Ser Ala Pro Asn Pro Asp Asp Pro Leu Ala Asn Asp Val Ala Glu Gln
        115                 120                 125

Trp Lys Thr Asn Glu Ala Gln Ala Ile Glu Thr Ala Arg Ala Trp Thr
    130                 135                 140

Arg Leu Tyr Ala Met Asn Asn Ile
145                 150
```

<210> SEQ ID NO 25
<211> LENGTH: 1203
<212> TYPE: DNA
<213> ORGANISM: Homo sapiens

<400> SEQUENCE: 25

```
actcgtgcgt gaggcgagag gagccggaga cgagaccaga ggccgaactc gggttctgac    60
aagatggccg ggctgccccg caggatcatc aaggaaaccc agcgtttgct ggcagaacca   120
gttcctggca tcaaagccga accagatgag agcaacgccc gttattttca gtggtcatt    180 gctggccctc aggattcccc ctttgaggga gggacttttta aacttgaact attccttcca   240
gaagaatacc caatggcagc ccctaaagta cgtttcatga ccaaaattta tcatcctaat   300
gtagacaagt tgggaagaat atgtttagat attttgaaag ataagtggtc cccagcactg   360
cagatccgca cagttctgct atcgatccag gccttgttaa gtgctcccaa tccagatgat   420
ccattagcaa atgatgtagc ggagcagtgg aagaccaacg aagcccaagc catagaaaca   480
gctagagcat ggactaggct atatgccatg aataatattt aaattgatac gatcatcaag   540
```

```
-continued tgtgcatcac ttctcctgtt ctgccaagac ttcctcctct ttgtttgcat ttaatggaca      600
cagtcttaga aacattacag aataaaaaag cccagacatc ttcagtcctt tggtgattaa      660
atgcacatta gcaaatctat gtcttgtcct gattcactgt cataaagcat gagcagaggc      720
tagaagtatc atctggattg ttgtgaaacg tttaaaagca gtggccctc cctgctttta       780 ttcatttccc ccatcctggt ttaagtataa agcactgtga atgaaggtag ttgtcaggtt      840
agctgcaggg gtgtgggtgt ttttatttta ttttatttta ttttattttt gagggggggag    900 gtagtttaat tttatgggct cctttccccc ttttttggtg atctaattgc attggttaaa     960
agcagctaac caggtcttta gaatatgctc tagccaagtc taactttatt tagacgctgt    1020
agatggacaa gcttgattgt tggaaccaaa atgggaacat taaacaaaca tcacagccct   1080
cactaataac attgctgtca agtgtagatt cccccttca aaaaagctt gtgaccattt      1140 tgtatggctt gtctggaaac ttctgtaaat cttatgtttt agtaaaatat tttttgttat    1200
tct                                                                   1203

<210> SEQ ID NO 26
<211> LENGTH: 42
<212> TYPE: DNA
<213> ORGANISM: Artificial sequence
<220> FEATURE:
<223> OTHER INFORMATION: primer sequence

<400> SEQUENCE: 26 cccccaagc tttgcatgca gattttcgtg aagaccctga cc                         42

<210> SEQ ID NO 27
<211> LENGTH: 45
<212> TYPE: DNA
<213> ORGANISM: Artificial sequence
<220> FEATURE:
<223> OTHER INFORMATION: primer sequence

<400> SEQUENCE: 27 cccccaagc ttgcgtgcat gcagattttc gtgaagaccc tgacc                      45
```